US012778388B2

(12) United States Patent
Rask et al.

(10) Patent No.: US 12,778,388 B2
(45) Date of Patent: Nov. 3, 2026

(54) MEDICAL DEVICE INCLUDING A TUBE

(71) Applicant: AMBU A/S, Ballerup (DK)

(72) Inventors: Jesper Domino Rask, Copenhagen S (DK); Morten Sørensen, Ballerup (DK); Martin Lund Størup, Brønshøj (DK); Lars Ulrik Nielsen, Virum (DK)

(73) Assignee: AMBU A/S, Ballerup (DK)

( * ) Notice: Subject to any disclaimer, the term of this patent is extended or adjusted under 35 U.S.C. 154(b) by 744 days.

(21) Appl. No.: 18/129,005

(22) Filed: Mar. 30, 2023

(65) Prior Publication Data

US 2023/0233064 A1 Jul. 27, 2023

Related U.S. Application Data

(63) Continuation-in-part of application No. 18/027,568, filed as application No. PCT/EP2021/073279 on Aug.

(Continued)

(30) Foreign Application Priority Data

Sep. 22, 2020 (DK) ........................... PA 2020 70621
Sep. 22, 2020 (DK) ........................... PA 2020 70622

(51) Int. Cl.
*A61B 1/00* (2006.01)
*A61B 1/015* (2006.01)

(Continued)

(52) U.S. Cl.
CPC ........ *A61B 1/0011* (2013.01); *A61B 1/00009* (2013.01); *A61B 1/0008* (2013.01);

(Continued)

(58) Field of Classification Search
CPC ....... A61B 1/267; A61B 1/2676; A61B 1/051; G02B 23/2476
See application file for complete search history.

(56) References Cited

U.S. PATENT DOCUMENTS 5,499,625 A 3/1996 Frass et al.
5,725,476 A 3/1998 Yasui et al.

(Continued)

FOREIGN PATENT DOCUMENTS

KR 10-2190218 B1 12/2020
WO 2017205357 A1 11/2017
WO 2019/044053 A1 3/2019

OTHER PUBLICATIONS

First technical report in Denmark Patent Application No. PA 2020 70621, dated Aug. 25, 2021, 9 pgs.

(Continued)

*Primary Examiner* — Alexandra L Newton
(74) *Attorney, Agent, or Firm* — Faegre Drinker Biddle & Reath LLP

(57) ABSTRACT

A medical device including a main tube having an outer wall, a first lumen, and a camera lumen; a tip housing separately manufactured from the main tube and including a tubular housing part extending from a proximal end to a distal end, a first lumen extension, a camera lumen extension, the tubular housing part enclosing the first lumen extension and the camera lumen extension, and the proximal end of the tip housing mounted at the distal end of the main tube; a camera module; a camera housing positioned in the camera lumen extension and affixing the camera module to the tip housing, the camera housing having a tubular housing part having an inner face; and a support structure including a tubular end part having an outer face adhesively bonded to the inner face of the tubular housing part to secure the camera module to the camera housing.

20 Claims, 33 Drawing Sheets

Related U.S. Application Data

23, 2021, application No. 18/129,005 is a continuation of application No. 18/044,491, filed as application No. PCT/EP2021/073278 on Aug. 23, 2021, now Pat. No. 12,616,361.

(51) Int. Cl.

| | |
|---|---|
| ***A61B 1/05*** | (2006.01) |
| ***A61B 1/12*** | (2006.01) |
| ***A61B 90/00*** | (2016.01) |
| ***A61M 16/04*** | (2006.01) |

(52) U.S. Cl.

CPC .......... *A61B 1/00128* (2013.01); *A61B 1/015* (2013.01); *A61B 1/05* (2013.01); *A61B 1/126* (2013.01); *A61M 16/0434* (2013.01); *A61M 16/0475* (2014.02); *A61B 2090/034* (2016.02)

(56) References Cited

U.S. PATENT DOCUMENTS 5,904,648 A 5/1999 Arndt et al.
6,079,409 A 6/2000 Brain
6,142,144 A 11/2000 Pacey
6,248,060 B1 6/2001 Buess et al.
6,533,722 B2 3/2003 Nakashima
6,543,447 B2 4/2003 Pacey
6,655,377 B2 12/2003 Pacey
6,923,176 B2 8/2005 Ranzinger
6,929,600 B2 8/2005 Hill
7,013,899 B2 3/2006 Alfery et al.
7,201,168 B2 4/2007 McGrail et al.
7,233,820 B2 6/2007 Gilboa
7,458,375 B2 12/2008 Schwartz et al.
7,530,946 B2 5/2009 Hartwick
7,658,708 B2 2/2010 Schwartz et al.
7,921,847 B2 4/2011 Totz
7,938,119 B2 5/2011 Chen et al.
7,998,062 B2 8/2011 Gilboa
8,038,606 B2 10/2011 Otawara
8,998,798 B2 4/2015 Hayman et al.
9,155,854 B2 10/2015 Hayman et al.
9,283,342 B1 3/2016 Gardner
9,332,891 B2 5/2016 Vazales et al.
9,357,905 B2 6/2016 Molnar et al.
9,415,179 B2 8/2016 Molnar
9,572,946 B2 2/2017 Chun
9,579,012 B2 2/2017 Vazales et al.
9,603,515 B2 3/2017 Zocca et al.
9,662,466 B2 5/2017 Gunday et al.
9,750,913 B2 9/2017 Schwartz et al.
9,788,755 B2 10/2017 Hayman et al.
9,801,535 B2 10/2017 Turnbull
9,820,642 B2 11/2017 Law et al.
9,854,962 B2 1/2018 McGrail et al.
9,855,111 B2 1/2018 Vazales et al.
9,888,832 B2 2/2018 Schwartz et al.
9,907,624 B2 3/2018 Vazales et al.
9,918,618 B2 3/2018 Molnar
9,949,629 B2 4/2018 Gardner
10,149,602 B2 12/2018 Daher et al.
10,245,402 B2 4/2019 Daher et al.
10,406,309 B2 9/2019 Daher
10,478,054 B2 11/2019 Nave et al.
10,888,679 B2 1/2021 Daher et al.
2001/0017135 A1 8/2001 Cook
2005/0129592 A1 6/2005 Kihara et al.
2005/0268917 A1 12/2005 Boedeker et al.
2006/0025650 A1 2/2006 Gavriely
2008/0188715 A1 8/2008 Fujimoto
2008/0200764 A1 8/2008 Okada
2009/0253964 A1 10/2009 Miyamoto
2011/0197888 A1 8/2011 Deutsch et al.
2011/0275894 A1 11/2011 Mackin
2011/0313347 A1 12/2011 Zocca et al.
2011/0315147 A1 12/2011 Wood et al.
2012/0065469 A1 3/2012 Allyn et al.
2012/0172664 A1 7/2012 Hayman et al.
2012/0172665 A1 7/2012 Allyn et al.
2012/0226100 A1 9/2012 Greenburg et al.
2012/0259173 A1 10/2012 Waldron et al.
2012/0298111 A1* 11/2012 Wood ................ A61M 16/0443 128/207.14
2012/0302833 A1 11/2012 Hayman et al.
2013/0158351 A1* 6/2013 Daher .................... A61B 1/313 600/109
2013/0269703 A1 10/2013 Wood et al.
2013/0303849 A1 11/2013 Allyn et al.
2013/0317339 A1 11/2013 Waldstreicher et al.
2013/0324798 A1 12/2013 Molnar et al.
2013/0338436 A1 12/2013 Dresher et al.
2014/0005480 A1 1/2014 Wagner et al.
2014/0024893 A1 1/2014 Dorsey et al.
2014/0024895 A1 1/2014 Allyn
2014/0031622 A1 1/2014 Daher
2014/0033455 A1 2/2014 Vazales et al.
2014/0073853 A1 3/2014 Swisher et al.
2014/0076326 A1 3/2014 Pol
2014/0094651 A1 4/2014 Allyn et al.
2014/0094652 A1 4/2014 Lewis et al.
2014/0094653 A1 4/2014 Lewis et al.
2014/0150782 A1 6/2014 Vazales et al.
2014/0221921 A1 8/2014 Gilboa
2014/0309494 A1 10/2014 Molnar
2015/0099927 A1 4/2015 Sadoughi
2015/0126808 A1 5/2015 Roze
2015/0133741 A1 5/2015 Gill
2015/0174352 A1 6/2015 Hayman et al.
2015/0190044 A1 7/2015 Livnat
2015/0223668 A1 8/2015 Gilboa et al.
2015/0305596 A1 10/2015 Oskin et al.
2015/0305650 A1 10/2015 Hunter et al.
2015/0378144 A1 12/2015 Handte et al.
2016/0000303 A1 1/2016 Klein et al.
2016/0030693 A1 2/2016 Nakatate et al.
2016/0038008 A1 2/2016 Molnar
2016/0038014 A1 2/2016 Molnar
2016/0051221 A1 2/2016 Dickhans et al.
2016/0081534 A1 3/2016 Lisogurski et al.
2016/0101253 A1 4/2016 Alahmadi
2016/0106308 A1 4/2016 Field
2016/0206189 A1 7/2016 Nearman et al.
2016/0227991 A1 8/2016 Hayut et al.
2016/0256646 A1 9/2016 Vazales
2016/0262603 A1 9/2016 Molnar
2017/0119494 A1 5/2017 Vazales et al.
2017/0232216 A1 8/2017 Nave et al.
2018/0084971 A1 3/2018 Truckai et al.
2019/0083728 A1 3/2019 Nawn et al.
2019/0246873 A1 8/2019 Lu et al.
2020/0060514 A1* 2/2020 Sakamoto .............. A61B 1/051
2020/0288953 A1 9/2020 Sørensen et al.
2020/0297193 A1 9/2020 Takahashi et al.
2020/0352650 A1 11/2020 Chu et al.
2021/0068625 A1 3/2021 Shin et al.
2023/0355085 A1 11/2023 Rask et al.
2023/0380676 A1 11/2023 Rask et al.

OTHER PUBLICATIONS

First technical report in Denmark Patent Application No. PA 2020 70622, dated Mar. 15, 2021, 8 pgs.
International Search Report and Written Opinion in International Application No. PCT/EP2021/073278, mailed 2021-11-30, 14 pgs.
International Search Report and Written Opinion in International Application No. PCT/EP2021/073279, mailed 2021-12-03, 14 pgs.

* cited by examiner

MEDICAL DEVICE INCLUDING A TUBE

CROSS-REFERENCE TO RELATED APPLICATIONS

This application is a continuation-in-part of U.S. patent application Ser. No. 18/044,491, filed Mar. 8, 2023, and U.S. patent application Ser. No. 18/027,568, filed Mar. 21, 2023. U.S. patent application Ser. No. 18/044,491 is a National Phase entry under 35 U.S.C. § 371 of International Application No. PCT/EP2021/073278, filed Aug. 23, 2021, which claims the benefit of and priority from Denmark Patent Application No. PA 2020 70622, filed Sep. 22, 2020. U.S. patent application Ser. No. 18/027,568 is a National Phase entry under 35 U.S.C. § 371 of International Application No. PCT/EP2021/073279, filed Aug. 23, 2021, which claims the benefit of and priority from Denmark Patent Application No. PA 2020 70621, filed Sep. 22, 2020. The aforementioned applications are incorporated by reference herein in their entirety.

TECHNICAL FIELD

The present disclosure relates to a medical device including a tube having a lumen, a camera lumen, and a camera module positioned in the camera lumen adjacent the distal end of the lumen.

BACKGROUND

Commonly owned U.S. Pat. No. 10,149,602 discloses an endobronchial tube which contains an integrated camera and light source and a cleaning nozzle arrangement disposed within a dedicated peripheral lumen within the tube's wall. The camera is arranged in the peripheral lumen of the tube at the distal end of the tracheal lumen in order to visualize the tracheal carina and the distal end of the bronchial lumen during its insertion into the left or right bronchus. The fitting of a camera module in the dedicated peripheral lumen may be cumbersome. In a manual procedure, firstly, the peripheral lumen may be dilated in order to fit the camera module, and, secondly, the camera module may be fixed in the lumen by means of glue. Following this procedure, correct positioning of the camera module in the peripheral lumen may be difficult. Furthermore, in a double lumen tube, it may be a disadvantage that the angle of view of the camera may be restricted in such a way that the captured image shows to a large degree the distal end of the bronchial lumen rather than the anatomy of the patient.

It is desirable to reduce the assembly and manufacturing costs of medical devices comprising tubes and camera modules, particularly in medical devices intended to be discarded after use.

SUMMARY

An object of the present disclosure is to provide a medical device that is easy to produce and assemble correctly and less expensively than currently known devices.

In view of this object, in a first aspect of the invention a medical device is provided with a separately manufactured tip housing mounted on a main tube of the medical device, and a camera module is positioned in the tip housing. The separately manufactured tip housing may be manufactured by manufacturing techniques different than those used to manufacture the main tube, providing design flexibility and resultant benefits, such as forming the tip housing precisely for fast, easy and correct positioning of the camera module, and perhaps forming other features, such as flushing channels, without manual adaptation during assembly. A more precise camera mounting in terms of translational and rotational positioning may lead to less variance in camera angle between different devices, and thereby less variance in the view of the patient's important landmarks in the airway, as seen from an operator perspective. In general, improved quality and consistency of the final product may be achieved as a result of less operator dependency during production of the device.

In view of this object, in a second aspect of the invention a medical device is provided with a camera housing provided to mount the camera module in a camera lumen. Thereby, precise mounting of a camera module in the camera lumen may be facilitated in that a tight fit between the camera housing and the camera lumen may ensure precise positioning of the camera module in the lumen without any adjustments being necessary. In particular, dilatation of the camera lumen of the tube in order to mount the camera module in the camera lumen may not be necessary.

In a third aspect of the invention, an assembly method is provided for mounting the camera module in the camera housing and the camera lumen.

In a fourth aspect of the invention, a visualization system is provided which comprises a medical device according to the first and second aspects, and variations and examples thereof, and a video processing apparatus.

Embodiments of the medical device according to the first aspect include the following:

In one embodiment, a proximal end of the tip housing is mounted on the main tube and the camera module is arranged at least partly in a camera lumen extension of the tip housing. The camera module may be fixed in the tip extension of the camera lumen by means of a camera housing. Any of the embodiments, variations, and examples of the camera housing described with reference to the second aspect of the invention may be used to secure the camera module in the tip housing.

The main tube is preferably manufactured by extrusion.

In a variation of the present embodiment, the main tube has a flush lumen enclosed by the outer wall, the flush lumen has a proximal end and a distal end, the tip housing forms a tip extension of the flush lumen, and the tip extension of the flush lumen communicates with at least one flush outlet directed at a lens end of the camera module or a window of the camera housing positioned distally of the lens. Thereby, by forming the tip extension of the flush lumen in the tip housing, nozzles may be more precisely configured as compared to manually cut nozzles in existing solutions, thereby resulting in better performance when cleaning the camera front. For instance, if a patient has a lot of secretion in the airway, this can get in front of the camera. In this case, the flush outlet may be used to wash and/or blow away the secretion to regain a clear picture.

The camera module may be fixed in the tip extension of the camera lumen by means of a camera housing, and the at least one flush outlet forms part of the camera housing. Thereby, by arranging the flush outlet or outlets as an integrated part of the camera housing, an even more efficient cleaning of the camera or camera housing front may be obtained as a result of close and precise positioning of the flush outlet in relation to a front lens of the camera or a transparent wall behind which a camera lens stack is arranged. The camera module may be fixed in the tip extension of the camera lumen without a camera housing, by means of a camera module support.

In an example of the present variation, the tip extension of the flush lumen is provided with a protruding pipe engaging the flush lumen of the main tube. Thereby, a continuous lumen without blockage in the junction may be ensured. The protruding pipe may be manufactured as an integrated part of the tip housing or may be a separate pipe component inserted into the tip housing.

In a variation of the present embodiment, the main tube is provided with a first inflatable cuff, the main tube has a first cuff lumen enclosed by the outer wall and communicating with the first inflatable cuff, the first cuff lumen has a proximal end and a distal end, and the distal end of the first cuff lumen is closed by means of a sealing plug arranged on the tip housing. Thereby, a first inflatable cuff may be arranged on the main tube without having to manually close the distal end of the first cuff lumen during production. The sealing plug may be a separate part arranged on the tip housing or it may be an integral part of the tip housing.

In a variation of the present embodiment, the main tube has an anesthetic lumen enclosed by the outer wall, the anesthetic lumen has a proximal end and a distal end, the tip housing forms a tip extension of the anesthetic lumen, and the tip extension of the anesthetic lumen communicates with at least one anesthetic outlet port. Thereby, the at least one anesthetic outlet port may be precisely formed during manufacturing of the tip housing without manual adaptation during production of the device.

In a variation of the present embodiment, the tip extension of the anesthetic lumen is provided with a protruding pipe engaging the anesthetic lumen of the main tube. Thereby, a continuous lumen without blockage in the junction may be ensured. The protruding pipe may be manufactured as an integrated part of the tip housing or may be a separate pipe component inserted into the tip housing.

In a variation of the present embodiment, the main tube has a second lumen having a proximal end and a distal end, the second lumen is enclosed by the outer wall, and the tip housing forms a tip extension of the second lumen.

In a variation of the present embodiment, a distal tube is mounted on the distal end of the tip housing, thereby forming a further extension of the second lumen. Thereby, the distal tube may have different properties, such as hardness, stiffness, etc., than the main tube and/or the tip housing whereby more design freedom may be achieved. The distal tube may preferably be an extruded tube. For instance, the distal tube may be more flexible than the main tube and may at least be more flexible than the tip housing. However, alternatively, the distal tube could be replaced by an integrated part of the tip housing. Such integrated part of the tip housing and the tip housing itself could be produced together from two different materials, respectively, by a co-injection molding technique, whereby the materials have different properties, such as different flexibilities.

In a variation of the present embodiment, the distal tube is provided with a second inflatable cuff, the main tube has a second cuff lumen enclosed by the outer wall, the tip housing forms a tip extension of the second cuff lumen, the distal tube forms a distal second cuff lumen enclosed by an outer wall of the distal tube, and the distal second cuff lumen of the distal tube connects the tip extension of the second cuff lumen and the second inflatable cuff.

In a variation of the present embodiment, the tip extension of the second cuff lumen is provided with a first protruding pipe arranged at the proximal end of the tip housing and engaging the second cuff lumen of the main tube, and the tip extension of the second cuff lumen is provided with a second protruding pipe arranged at the distal end of the tip housing and engaging the distal second cuff lumen of the distal tube. Thereby, a continuous lumen without blockage in the junctions may be ensured. The protruding pipes may be manufactured as integrated parts of the tip housing or may be separate pipe components inserted into the tip housing.

In an example of the present variation, the camera module is fixed in the tip extension of the camera lumen by means of a camera housing extending in a longitudinal direction and having a proximal end and a distal end, the camera housing includes a tubular housing part at least partly surrounding the camera module and a distal end wall, the tubular housing part and the distal end wall are integrally molded and form one single housing element, and the tubular housing part fits tightly into the tip extension of the camera lumen of the tube. Thereby, precise mounting of a camera module in the tip extension of the camera lumen may be facilitated in that a tight fit between the tubular housing part and the camera lumen may ensure precise positioning of the camera module in the lumen without any adjustments being necessary.

In a variation of the present embodiment, the tip housing may be made by molding, such as injection molding, or 3D printing. Thereby it may be ensured that the tip extension of the camera lumen may be formed precisely for fast, easy and correct positioning of the camera module, and thereby forming other necessary details, such as flushing channels, without manual adaptation during assembly.

In a variation of the present embodiment, the proximal end of the tip housing has a proximal junction interface fitting an abutment surface of the main tube, said abutment surface includes at least an end face of the outer wall of the main tube, the proximal junction interface forms a groove with said abutment surface of the main tube, and said groove contains hardened glue. Thereby, a secure connection between the proximal end of the tip housing and the main tube may be ensured.

In a variation of the present embodiment, the tip extension of the at least first lumen, at the proximal end of the tip housing, is provided with a protruding pipe engaging the at least first lumen of the main tube. Thereby, a continuous lumen without blockage in the junction may be ensured. The protruding pipe may be manufactured as an integrated part of the tip housing or may be a separate pipe component inserted into the tip housing.

In a variation of the present embodiment, the distal end of the tip housing has a distal junction interface fitting an abutment surface of the distal tube, said abutment surface includes at least an end face of the outer wall of the distal tube, the distal junction interface forms a groove with said abutment surface of the distal tube, and said groove contains hardened glue. Thereby, a secure connection between the distal end of the tip housing and the distal tube may be ensured.

In a variation of the present embodiment, the tip extension of the second lumen, at the distal end of the tip housing, is provided with a protruding pipe engaging the further extension of the second lumen formed in the distal tube. Thereby, a continuous lumen without blockage in the junction may be ensured. The protruding pipe may be manufactured as an integrated part of the tip housing or may be a separate pipe component inserted into the tip housing.

The medical device may be a catheter, an endotracheal tube, or an airway device.

Embodiments of the medical device according to the second aspect include the following:

In a first embodiment according to the second aspect, the camera housing includes a tubular housing part at least partly surrounding the camera module and a distal end wall integrally molded in one piece with the tubular housing part.

In some variations of the present embodiment, a separately manufactured tip housing is provided. The tip housing includes a camera lumen extension. The proximal end of the tip housing is mounted on the main tube and the camera module is arranged at least partly in the camera lumen extension of the tip housing. In other variations, the tubular housing part fits tightly into the camera lumen. Any of the embodiments, variations, and examples of the medical device and tip housing described with reference to the first aspect of the invention may be used in conjunction with the camera housing described with reference to the second aspect of the invention.

In a variation of the present embodiment, the camera housing includes a support structure for the camera module, the support structure has a proximal end and a distal end, the proximal end of the support structure has a tubular end part arranged inside the tubular housing part of the camera housing, the image transmission cable extends through the tubular end part of the support structure, and the distal end of the support structure is engaged with the camera module. Thereby, the arrangement of the camera module in the camera housing may be facilitated in that the tubular end part of the support structure may fit inside the tubular housing part and thereby ensure correct positioning of the support structure with the camera module inside the camera housing. Thereby, precise mounting of the camera module in the camera lumen may be further facilitated. Furthermore, the tubular end part of the support structure may seal against the tubular housing part, and the image transmission cable may seal against an inside of the tubular end part. Thereby, the camera module may be protected against the environment.

In a variation of the present embodiment, the tubular end part of the support structure has an outer face being glued to an inner face of the tubular part of the camera housing. Thereby, the tubular end part of the support structure may seal even better against the tubular housing part.

In a variation of the present embodiment, the outer face of the tubular end part of the support structure and/or the inner face of the tubular housing part of the camera housing are/is tapered or conical so that a gap for glue is formed, a cross-section of said gap generally decreasing in the direction from the proximal end to the distal end of the support structure. Thereby, correct application of glue may be ensured. Capillary effects may ensure that glue enters the gap and the decreasing cross-section of the gap may serve to avoid that glue enters too far inside of the camera housing.

In a variation of the present embodiment, the outer face of the tubular end part of the support structure and/or the inner face of the tubular part of the camera housing are/is provided with a number of ribs distributed in the circumferential direction of the outer face and/or the inner face. The ribs may ensure that the support structure is centered inside the camera housing such that the two parts can be glued together by utilizing capillary effects.

In a variation of the present embodiment, the ribs only extend at a distal end of the tubular end part of the support structure. Thereby, entrance of glue into the gap may be facilitated.

In a variation of the present embodiment, said ribs include two pivot forming ribs arranged diametrically opposite of the tubular end part of the support structure and/or of the tubular part of the camera housing and together providing a relatively tight fit with the corresponding outer face or inner face, and said ribs further include at least two distance ribs distributed peripherally about the tubular end part of the support structure and/or of the tubular part of the camera housing and together providing a relatively loose fit with the corresponding outer face or inner face. The two pivot forming ribs arranged diametrically opposite of the tubular end part of the support structure and/or of the tubular part of the camera housing may ensure that the support structure may pivot about an axis generally extending through said pivot forming ribs during the insertion of the support structure into the tubular part of the camera housing. Thereby, the distal end of the support structure may better engage the camera module in a flexible way so that the camera module may be guided into its correct position in the camera housing.

In a variation of the present embodiment, the distal end of the support structure is provided with two spaced tabs arranged generally symmetrically about a plane extending through said two pivot forming ribs, and the two spaced tabs are adapted to abut the camera module. Thereby, both spaced tabs may tend to engage the camera module during its insertion into the camera housing, thereby even better ensuring that the camera module may be guided into its correct position in the camera housing.

In a variation of the present embodiment, the support structure includes an elongated part having generally semi-circular cross-section, and the elongated part connects the proximal end of the support structure with the two spaced tabs. Thereby, the semi-circular support wall may mate with the interior structure of the camera housing.

In a variation of the present embodiment, the elongated part is provided with a peripherally extending recess facing the inner face of the tubular part of the camera housing next to the tubular end part of the support structure. The peripherally extending recess may stop the glue from moving further into the camera housing. This way it may be possible to control the amount of glue needed to ensure a good sealing effect.

In a variation of the present embodiment, the tubular end part of the support structure has an inner face being glued to an outer face of the image transmission cable. Thereby, a good sealing effect may be achieved.

In a variation of the present embodiment, the inner face of the tubular end part of the support structure is tapered or conical so that a gap for glue is formed, a cross-section of said gap generally decreasing in the direction from the proximal end to the distal end of the support structure. Thereby, correct application of glue may be ensured. Capillary effects may ensure that glue enters the gap and the decreasing cross-section of the gap may serve to avoid that glue enters too far inside of the camera housing.

In a variation of the present embodiment, the inner face of the tubular end part of the support structure is provided with a number of ribs distributed in the circumferential direction of the inner face. The ribs may ensure that image transmission cable is centered inside the tubular end part of the support structure such that the two parts can be glued together by utilizing capillary effects.

In a variation of the present embodiment, the support structure or the inner face of the tubular part of the camera housing has a guide rib extending in the longitudinal direction of the camera housing, the corresponding one of the support structure and the inner face of the tubular part of the camera housing has a groove extending in the longitudinal direction of the camera housing, and the guide rib is adapted to slide in the groove. Thereby, the tubular part of the camera housing may be configured to receive and guide the camera module support structure. In this way, it may be ensured that the camera module is guided to the correct rotational orientation inside the camera housing.

In a variation of the present embodiment, the camera module is arranged extending from the distal end of the support structure, the inner face of the tubular part of the camera housing is provided with the guide rib, and the guide rib is wedge-formed at the distal end of the camera housing in order to guide the camera module. Thereby, it may even better be ensured that the camera module is guided into its correct position during the last part of the insertion procedure of the support structure.

In a variation of the present embodiment, the inner face of the tubular part of the camera housing is provided with the guide rib, the elongated part is provided with the groove extending in the longitudinal direction of the camera housing, the groove is arranged symmetrically about the plane extending through said two pivot forming ribs, and the guide rib has a loose fit in the groove. The loose fit of the guide rib in the groove and the symmetric arrangement of the groove about said plane may even better ensure that the support structure may pivot about an axis generally extending through said pivot forming ribs during the insertion of the support structure into the tubular part of the camera housing. Thereby, the distal end of the support structure may better engage the camera module in a flexible way so that the camera module may be guided into its correct position in the camera housing.

In a variation of the present embodiment, a number of guide tabs are distributed in the circumferential direction of the inner face of the tubular part of the camera housing at the distal end wall of the camera housing, the guide tabs are provided on the inner face of the tubular part and/or on the distal end wall, and the guide tabs are arranged to guide the camera module during its insertion into the camera housing. Thereby, it may even better be ensured that the camera module may be guided into its correct position in the camera housing during its final displacement into the tubular housing part of the camera housing.

In a variation of the present embodiment, the distal end wall of the camera housing has a recess in which at least a portion of a lens barrel of the camera module is inserted. Thereby, correct positioning of the lens barrel of the camera module may be ensured, but also the optical properties of the image captured by the camera module may be improved. As an alternative to the recess, the distal end wall may be provided with a through-hole the lens barrel of the camera module is positioned. The camera module would then need to be glued and sealed towards the edge of the through-hole.

In a variation of the present embodiment, the camera housing includes a proximal portion arranged at a proximal end of the tubular housing part, the proximal portion has a proximal end and a distal end and a tapering part arranged between the proximal end and the distal end, and an outer diameter of the proximal end is smaller than an outer diameter of the distal end. Thereby, the camera housing may be mounted in the dedicated camera lumen of the tube by first threading the image transmission cable into the camera lumen from the distal end to the proximal end. The tapered part of the proximal portion of the camera housing may make it much easier to push the camera housing into the camera lumen of the tube which may be made of a soft/flexible polymer material. Thereby, dilatation of the camera lumen of the tube in order to mount the camera module in the camera lumen may be even less necessary.

In a variation of the present embodiment, the tubular housing part has an outer cylindrical surface, and the outer diameter of the distal end of the proximal portion corresponds to an outer diameter of the outer cylindrical surface. Thereby, insertion of the camera housing into the camera lumen of the tube may be even further facilitated.

In a variation of the present embodiment, the proximal portion is a separate element attached to the tubular housing part. Thereby, assembly of the camera housing may be facilitated.

In a variation of the present embodiment, the distal end of the proximal portion has a number of protrusions distributed in its circumferential direction and abutting the proximal end of the tubular part, and the tubular part and the proximal portion are connected by means of glue. The number of protrusions may ensure an appropriate gap for glue between the remaining part of the distal end of the proximal portion and the proximal end of the tubular part.

In a variation of the present embodiment, the proximal end of the tubular part has a number of protrusions distributed in its circumferential direction and abutting the distal end of the proximal portion, and the tubular part and the proximal portion are connected by means of glue. The number of protrusions may ensure an appropriate gap for glue between the remaining part of the proximal end of the tubular part and the distal end of the proximal portion.

In a variation of the present embodiment, the image transmission cable is retained inside of the proximal portion. Thereby, a strain relief for the image transmission cable may be ensured. Thereby, a pull relief may be provided for the image transmission cable so that the user does not inadvertently pull the cable apart from the camera module.

In a variation of the present embodiment, a crimp is fixed on the image transmission cable inside the proximal portion. Thereby, in a simple manner, a pull relief may be provided for the image transmission cable so that the user does not inadvertently pull the cable apart from the camera module.

In a variation of the present embodiment, the tubular housing part of the camera housing has a cylindrical outer surface having a central axis of symmetry, and a lens barrel of the camera module is eccentrically arranged in relation to the cylindrical outer surface of the tubular housing part. Thereby, the transverse position of the camera in the dedicated camera lumen of the tube may be adapted according to requirements by adapting the rotational position of the camera housing in the dedicated camera lumen of the tube. Thereby, the image captured by the camera may be influenced.

In a variation of the present embodiment, a central axis of the lens barrel of the camera module is displaced in relation to the central axis of symmetry of the cylindrical outer surface of the tubular housing part of the camera housing in a direction so that the lens barrel is closer to the first lumen than to the second lumen. Thereby, in the case that the second lumen extends further distally than the first lumen, it may be ensured that the viewing angle of the camera covers relatively more of the surroundings of the tube than it covers of the part of the tube enclosing the second lumen distally of the first lumen. Thereby, in particular in the case of the medical device being a double lumen endotracheal tube having a first lumen in the form of a tracheal lumen and a second lumen in the form of a bronchial lumen, it may be ensured that the image captured by the camera module shows more of the anatomy and less of a tubing of a bronchial lumen with inflatable cuff inserted into the bronchus.

The medical device may be a catheter, an airway device, or an endotracheal tube.

In a variation of the present embodiment, the medical device is a double lumen endotracheal tube having a first lumen in the form of a tracheal lumen and a second lumen in the form of a bronchial lumen, the first lumen and the second lumen extend together from the proximal end of the first lumen to the distal end of the first lumen, and the second lumen extends beyond the distal end of the first lumen to a distal end of the second lumen.

In an example according to the present variation, the double lumen endotracheal tube has a first inflatable cuff arranged proximally the open distal end of the first lumen and a second inflatable cuff arranged proximally the open distal end of the second lumen.

In an example according to the present variation, the first lumen and the camera lumen, and an optional second lumen, are co-extruded to form the tube.

In an example according to the present variation, the outer wall of the tube is generally ring-formed and surrounds at least the first lumen, and the camera lumen is formed in the material of the outer wall between an inner surface and an outer surface of the outer wall.

In an example according to the present variation, the outer wall of the tube further surrounds at least part of a second lumen having a proximal end and an open distal end, and the first lumen and the second lumen are separated by means of a partition wall.

In an example according to the present variation, the camera lumen is formed in the material of the outer wall at a position where the partition wall is connected to the outer wall.

In an example according to the present variation, the outer wall of the tube surrounds the first lumen and a second lumen, the first lumen and the second lumen are separated by means of a partition wall, and the camera lumen is formed at the outer wall at a position where the partition wall is connected to the outer wall.

In an example according to the present variation, the first lumen and the second lumen are symmetrically arranged about the partition wall and in relation to the camera lumen.

In an embodiment according to the fourth aspect of the invention, a visualization system is provided which comprises a medical device according to the first and second aspects, and variations and examples thereof, and a video processing apparatus with a medical device interface configured to interface with the camera module of the medical device. Customized interfacing between the medical device and the video processing apparatus optimizes generation of the video pipeline and adaptive configuration of the camera module responsive to lighting and other conditions inside the patient.

BRIEF DESCRIPTION OF THE DRAWINGS

The above-mentioned embodiments, variations, examples, features and advantages thereof will be further elucidated by the following illustrative and nonlimiting detailed description of embodiments of the invention disclosed herein with reference to the appended drawings, wherein.

In the drawings, corresponding reference characters indicate corresponding parts, functions, and features throughout the several views. The drawings are not necessarily to scale and certain features may be exaggerated in order to better illustrate and explain the disclosed embodiments.

DETAILED DESCRIPTION

Figure 1:
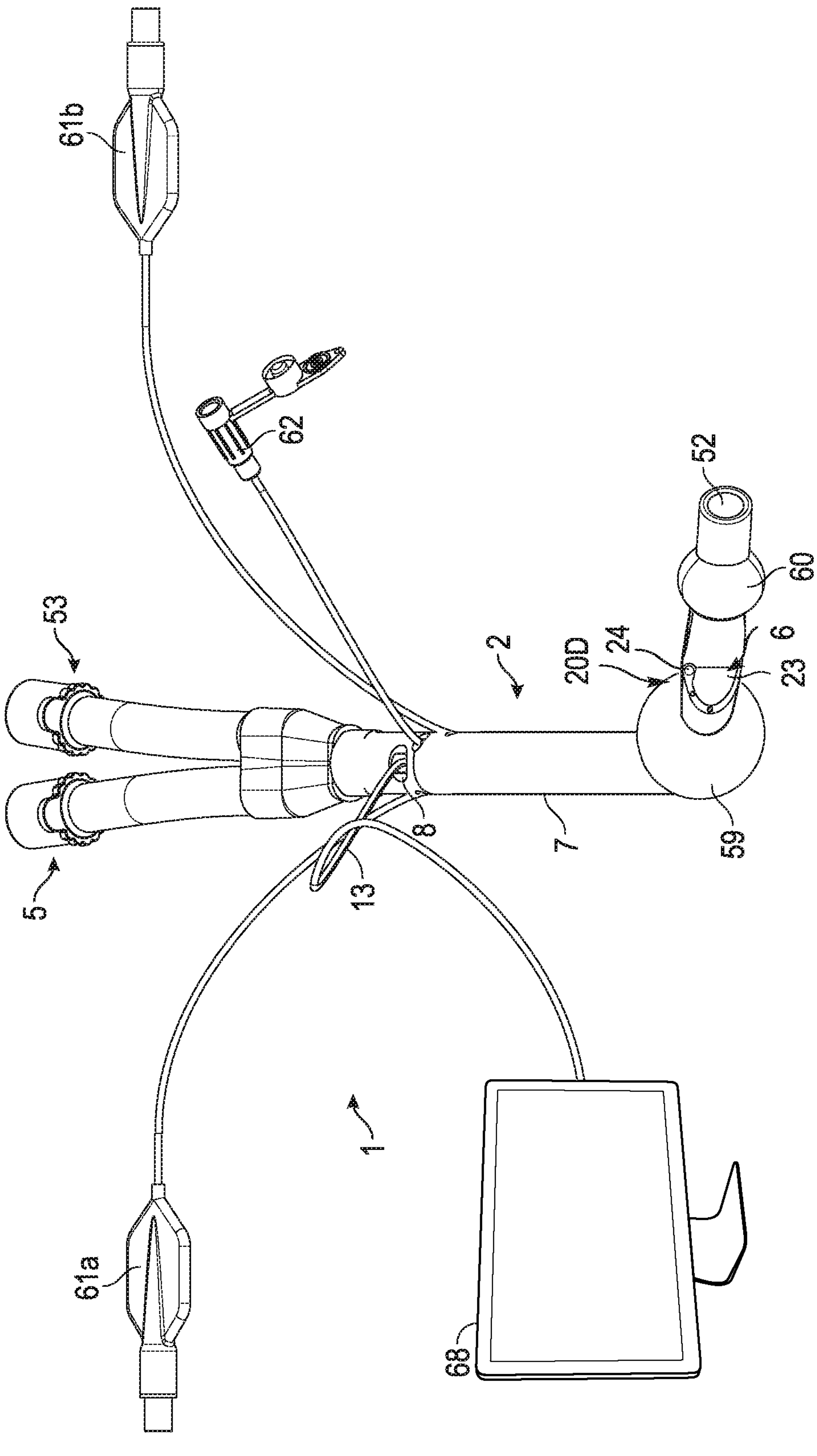
FIG. 1 is a perspective view of a double lumen endotracheal tube.
Figure 2:
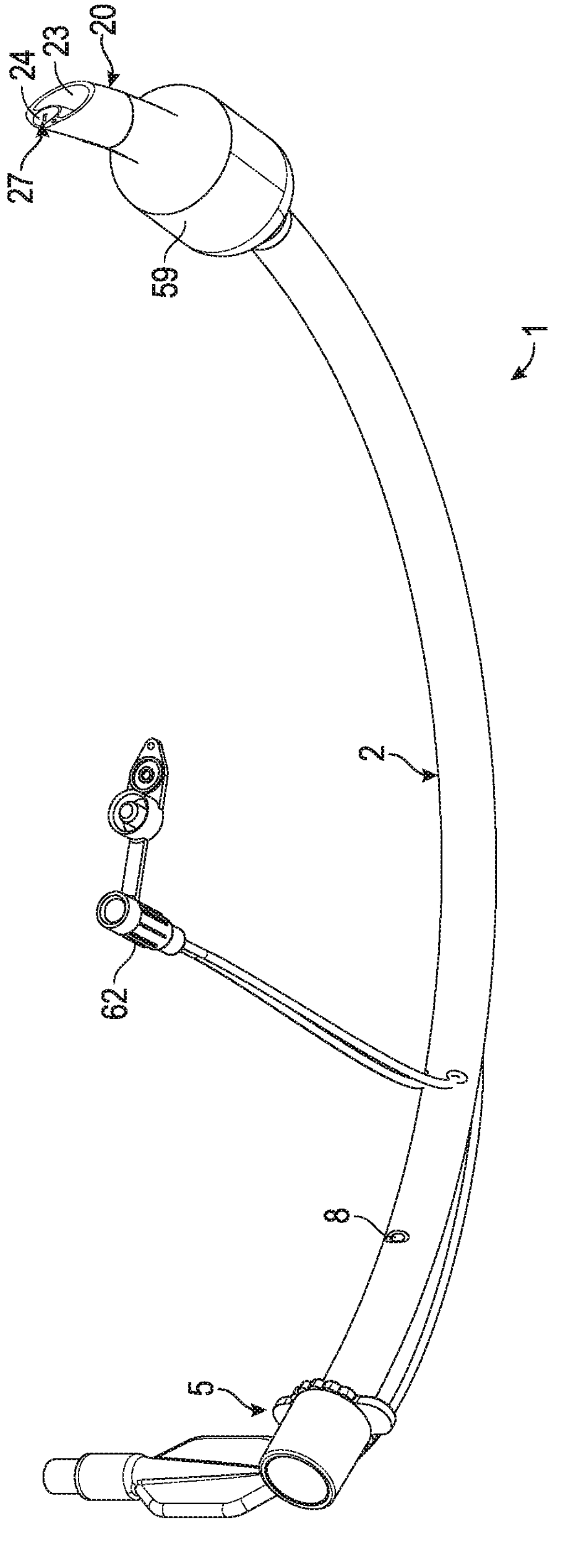
FIG. 2 is a perspective view of an embodiment of a single lumen endotracheal tube.

FIGS. 1 and 2 illustrate two variations of a medical device 1 comprising a main tube 2 having an outer wall 7, a tip housing 20, 20D extending from the main tube 2, a first lumen 3 and a camera lumen 4 (not shown in FIG. 1). The first lumen 3 comprises a main tube first lumen 3A (not shown in FIG. 1) and a first lumen extension 23 and extends from a proximal end 5 to a distal end 6. The camera lumen 4 comprises a main tube camera lumen 4A (not shown in FIG. 1) and a camera lumen extension 23. The camera lumen 4 has a proximal end 8. The outer wall 7 encloses the main tube first lumen 3A and the main tube camera lumen 4A. In FIG. 1 the medical device 1 is in the form of a double lumen endotracheal tube including the tip housing 20D. In FIG. 2 the medical device 1 is in the form of a single lumen endotracheal tube including the tip housing 20. The medical device can also be a catheter, for example. The tip housing 20, 20D is separately manufactured from the main tube 2 and is described in detail below. Generally, the tip housing 20, 20D comprises lumen extensions aligned with the lumens of the main tube 2, sometimes axially aligned. The tip housing 20, 20D may also comprise a flush outlet configured to discharge fluid to clean a lens or window distal of a camera module positioned in the camera lumen 4. A flush connection 62 supplies fluid to the flush outlet, described below. A camera module, described below, is arranged in the camera lumen 4. As used herein, a lumen extension refers to a lumen in the tip housing that is aligned with a corresponding lumen in the main tube, and may also be described as a tip extension of said main tube lumen.

Referring to FIG. 1, the first lumen 3 extends from the proximal end 5. A second lumen 52 extends from a proximal end 53 further than the distal end 6 of the first lumen 3. The double lumen endotracheal tube has a first inflatable cuff 59 arranged proximally the open distal end 6 of the first lumen 3 and a second inflatable cuff 60 arranged proximally the open distal end 54 of the second lumen 52. Each of the first and second inflatable cuffs 59, 60 may be inflated in a well-known manner via a pilot balloon 61*a*, 61*b* provided with a one-way valve. An image transmission cable 13 is attached to the camera module and extends through part of the camera lumen 4A to, during use, connect to an video processing apparatus (VPA) 68, directly or by means of a wireless connection. As shown, the image transmission cable 13 forms a wired connection that extends to the VPA 68. The image transmission cable 13 transmits the image data from an image sensor of the camera module and and power from the VPA 68 to the camera module 10 and the light sources 88. Furthermore, the image transmission cable 13 may include one or more fiber optic cables transmitting light from outside to the camera module. Example VPAs are described with reference to FIGS. 42 and 43.

Referring to FIG. 2, the single lumen endotracheal tube has the first inflatable cuff 59 arranged proximally the open distal end 6 of the first lumen 3 and the image transmission cable 13 (not shown in FIG. 2). A flush outlet 27 is shown positioned in the tip housing 20. The flush outlet 27 can also be provided in the tip housing 20D in the same manner.

The endotracheal tubes may be single use products. Single-use medical devices optimize workflow and reduce cost while saving patient's lives and improving patient care. They optimize workflow and reduce cost because they are always ready when needed without the traditional large-scale capital and repair budgets. They save patient's lives and improve patient care because they are readily available and do not pose a cross-contamination risk. This also reduces hospital re-admissions.

Figure 3:
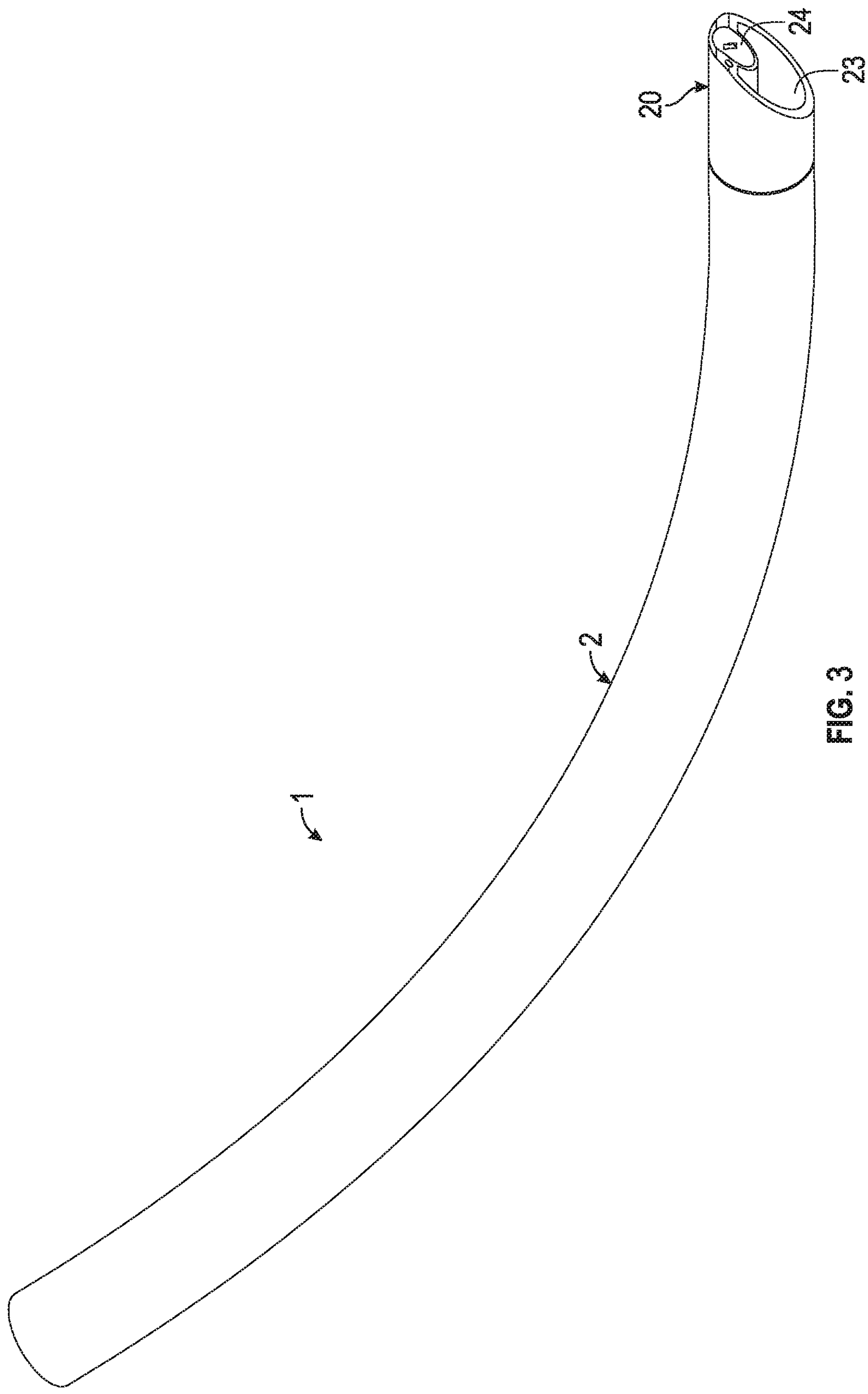
FIGS. 3 and 4 are perspective views of the endotracheal tube of FIG. 2.
Figure 4:
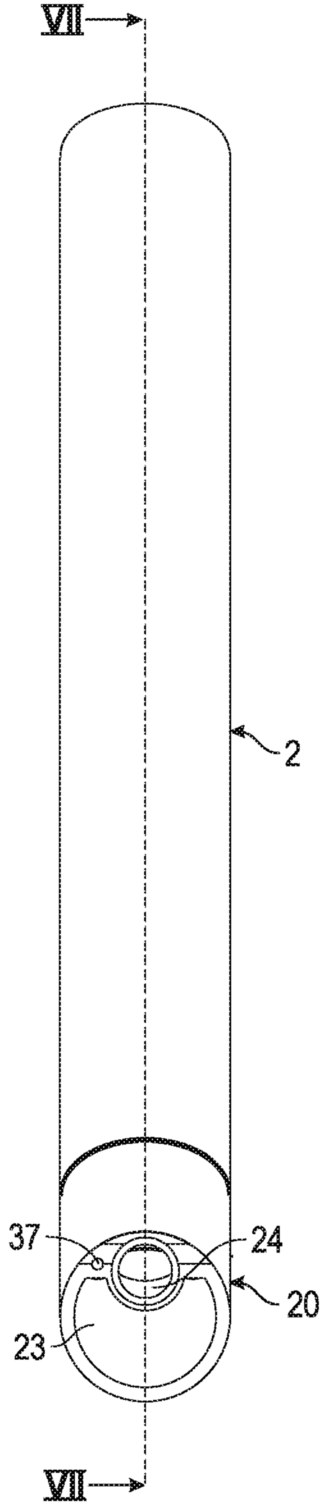
Figure 5:
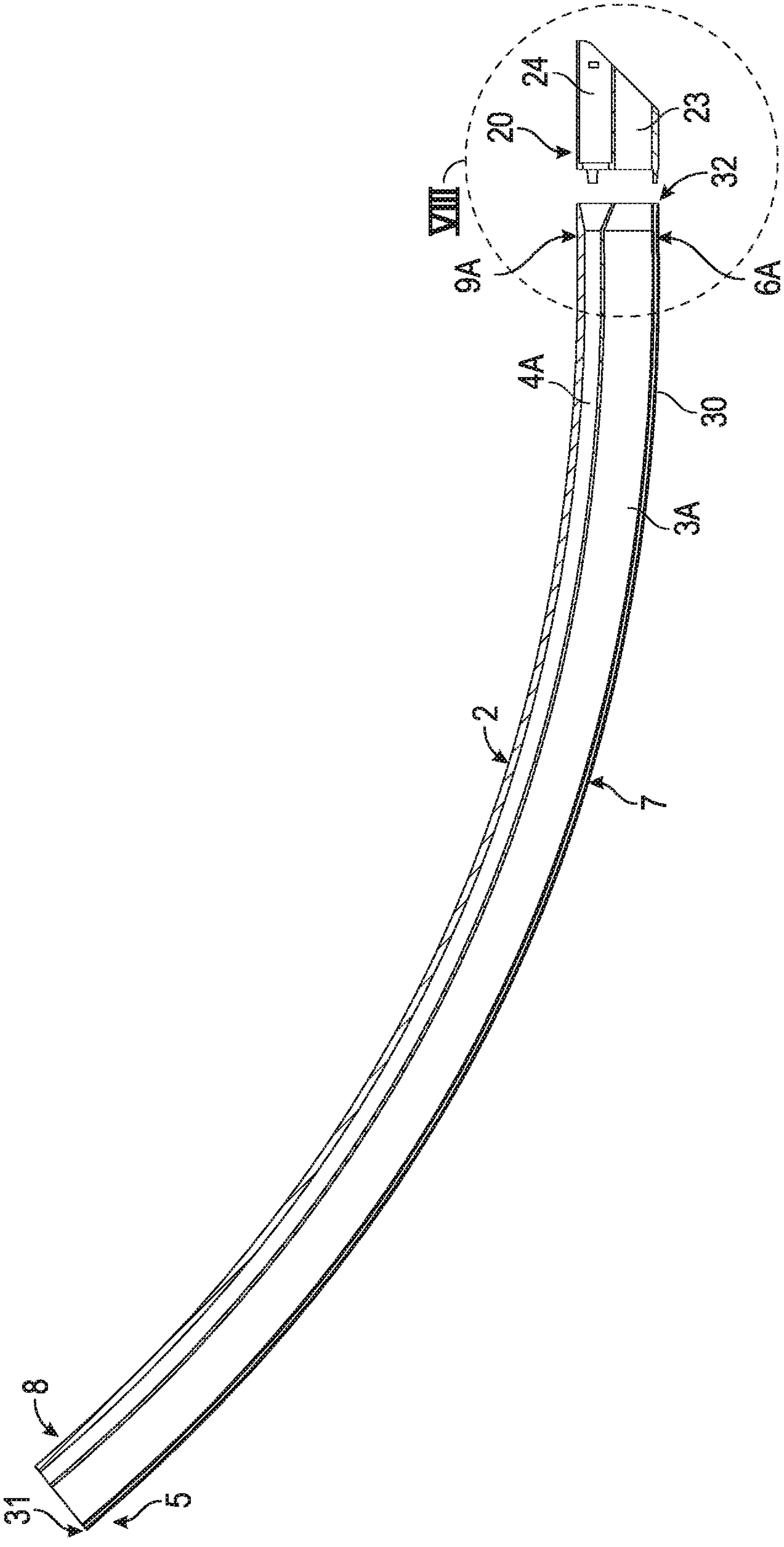
FIG. 5 is a sectional view, taken along the line VII-VII of FIG. 4, of the endotracheal tube of FIG. 1.

FIG. 3 shows the medical device 1 of FIG. 2 without the first inflatable cuff 59. FIG. 4 shows the medical device 1 of FIG. 3 including an anesthetic outlet port 37. An exploded sectional view of the medical device 1 as shown in FIG. 4, along a plane VII, is shown in FIG. 5. FIG. 5 also shows a first cuff lumen 30 being enclosed by the outer wall 7 and having a proximal end 31 and a distal end 32. The main tube first lumen 3A and the main tube camera lumen 4A are also shown. The first lumen extension 23 is aligned with the main tube first lumen 3A and a distal end 9 of the main tube camera lumen 4A is aligned with the camera lumen extension 24. The first cuff lumen 30 has a distal opening (not shown) covered by the first cuff 59 and operable to inflate the first cuff. Also shown is a distal end 9 of the main tube camera lumen 4A. A portion VIII of FIG. 5 is expanded and shown in FIG. 6.

Figure 6:
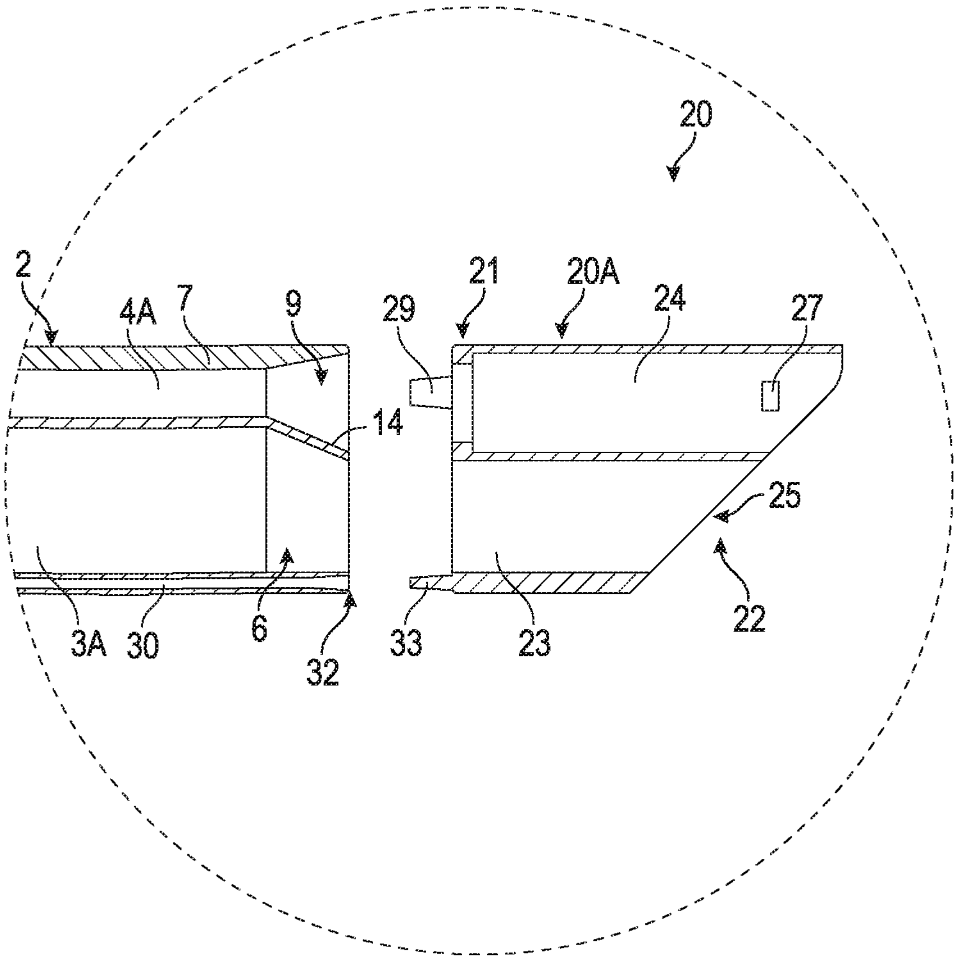
FIG. 6 shows, on a larger scale, the detail VIII of FIG. 5.

Referring to FIG. 6, the main tube first lumen 3A has a distal end 6. Optionally, the distal end 9 of the main tube camera lumen 4A has a tapered end 14. The tip housing 20, 20D comprises a tubular housing part 20A extending between a proximal end 21 and a distal end 22. The first lumen extension 23 has an open end 25. The tip housing 20, 20D, is provided with a protruding pipe 29, also referred to as a flush pipe. The tip housing 20, 20D comprises, on the proximal end 21, a sealing plug 33 provided to close the distal end 32 of the first cuff lumen 30. Thereby, the first inflatable cuff 59 may be arranged on the main tube 2 without having to separately close the distal end 32 of the first cuff lumen 30 during production. The sealing plug 33 may be a separate part arranged on the tip housing 20 or it may be an integral part of the tip housing 20.

Figure 7:
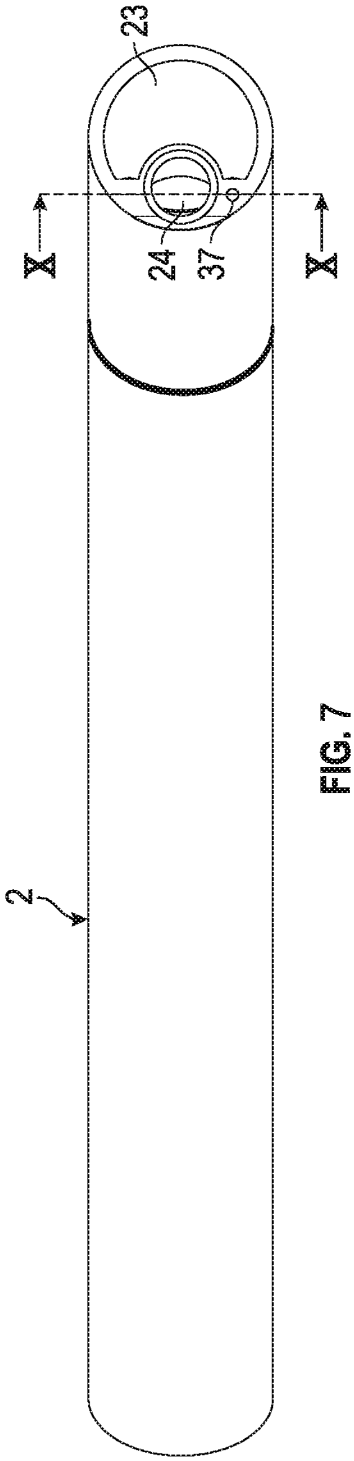
FIG. 7 is a top view of the single lumen endotracheal tube of FIG. 5.
Figure 8:
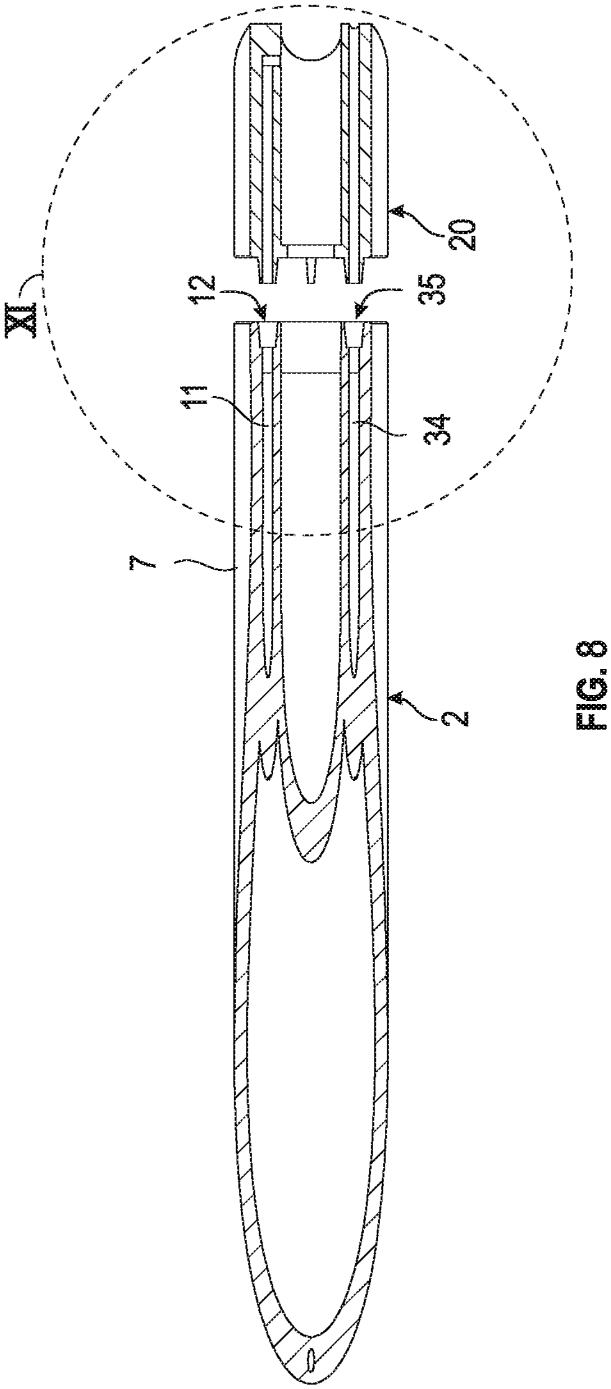
FIG. 8 is an exploded sectional view taken along the line X-X of FIG. 7.

FIG. 7 is a side view of the medical device 1 as shown in FIG. 3. An exploded sectional view of FIG. 7, along a plane X, is shown in FIG. 8. A portion XI of FIG. 8 is expanded and shown in FIG. 9. FIG. 10 is a perspective view of the tip housing 20. As illustrated in FIGS. 7 to 10, the proximal end 21 of the tip housing 20 is mounted onto the distal end of the main tube 2. FIG. 8 additionally shows a main tube flush lumen 11 having a distal end 12 and the main tube anesthetic lumen 34 having a distal end 35, both enclosed by the outer wall 7.

Figure 9:
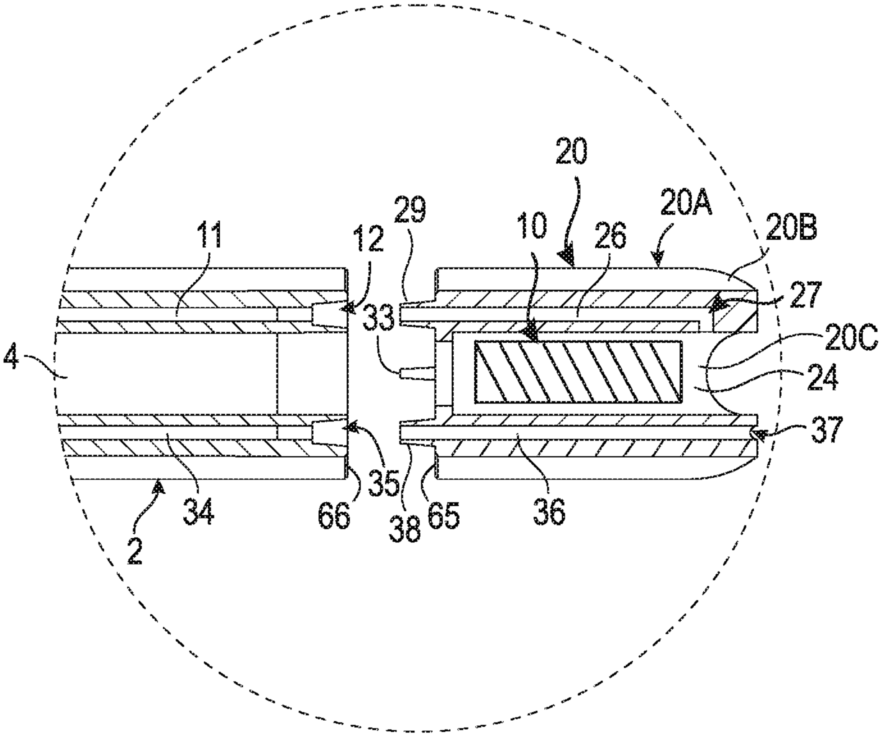
FIG. 9 shows, on a larger scale, the detail XI of FIG. 8.
Figure 10:
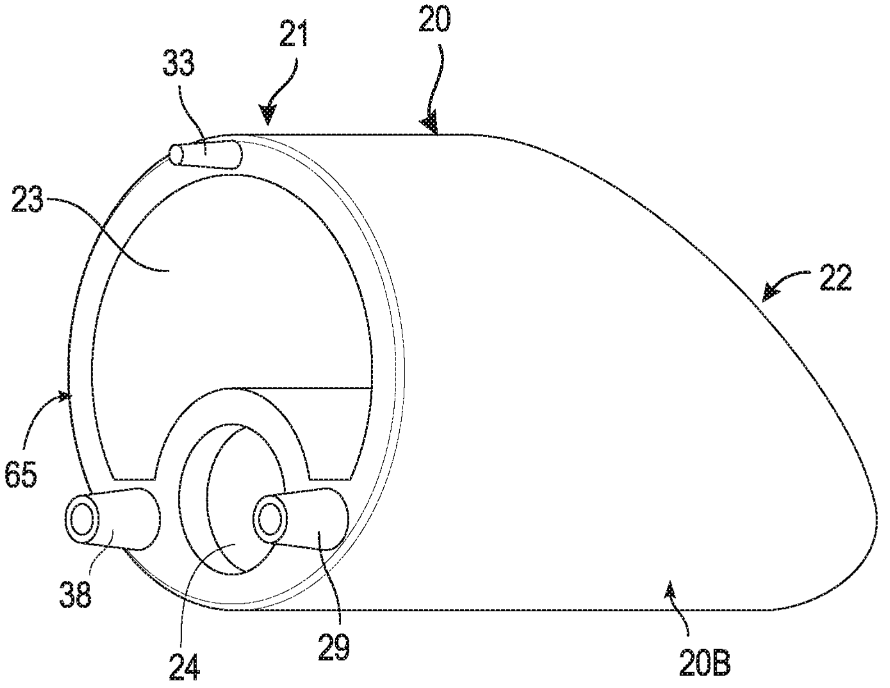
FIG. 10 is a perspective view of a tip housing of the single lumen endotracheal tube of FIG. 5.

As seen in FIG. 9, the tip housing 20 comprises an optional flush pipe 29 and an optional anesthetic pipe 38, both protruding proximally from the proximal end 21 of the tip housing 20 and configured to connect with the main tube flush lumen 11 and the main tube anesthetic lumen 34, thus fluidly coupling the main tube flush lumen 11 and the main tube anesthetic lumen 34 with the flush lumen extension 26 and the anesthetic lumen extension 36 of the tip housing 20. Thereby, continuous lumens without blockage in the junction may be ensured. The proximal end 21 of the tip housing 20 has a proximal junction interface 65 fitting an abutment surface 66 of the main tube 2.

The flush outlet 27 is also shown, extending to an inner surface 20C of the tubular housing part 20 of the tip housing 20, which inner surface defines, at least in part, the camera lumen extension 24. The tip housing 20 also has an outer surface 20B. Accordingly, a liquid supplied via the main tube flush lumen 11 can be delivered distally of the camera module 10 to wash or clear fluids and tissue and allow the camera module to obtain a clear view. The protruding pipe 29 may be manufactured as an integrated part of the tip housing 20 or may be a separate pipe component inserted into the tip housing 20. At least one anesthetic outlet port 37, at the distal end of the anesthetic extension lumen 36, may be precisely formed during manufacturing of the tip housing 20 without manual adaptation during production of the device. The anesthetic outlet port 37 may allow administration of a local anesthetic to prevent pharyngeal (gag) reflex, which may be advantageous during awake intubation.

Figure 11:
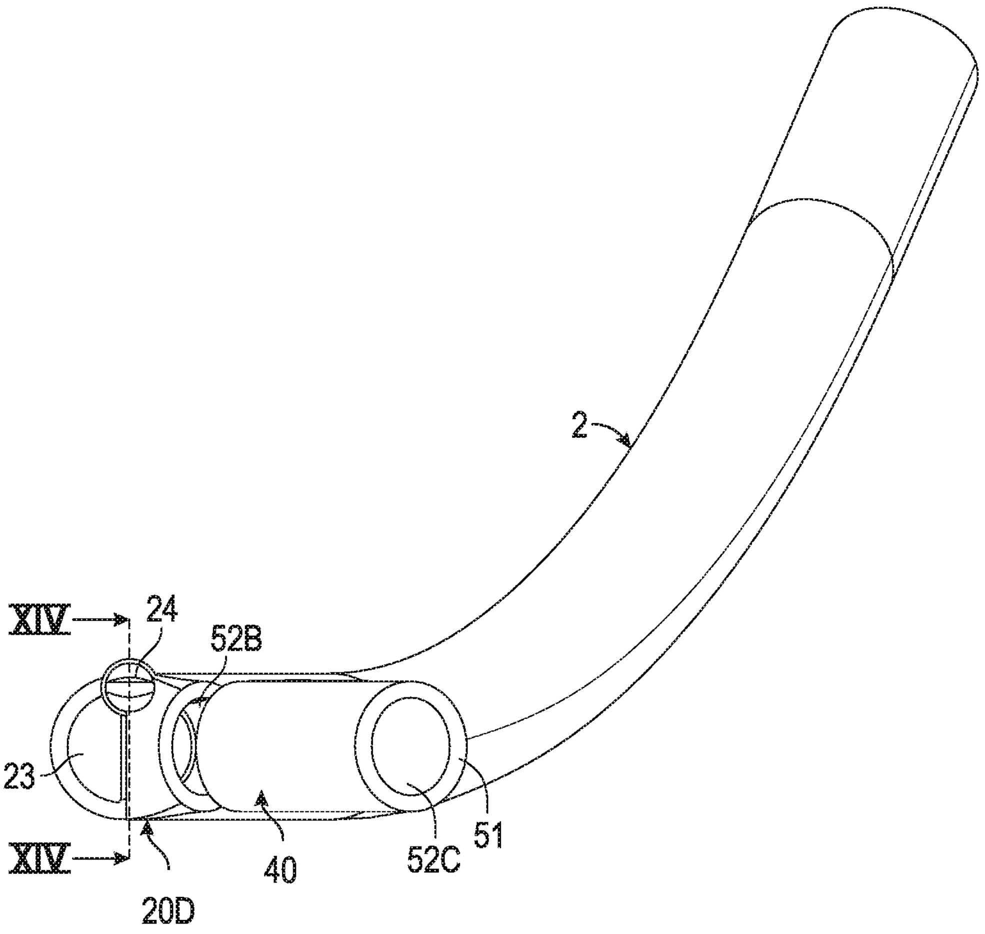
FIG. 11 is an exploded side view of an embodiment of the double lumen endotracheal tube of FIG. 1.
Figure 12:
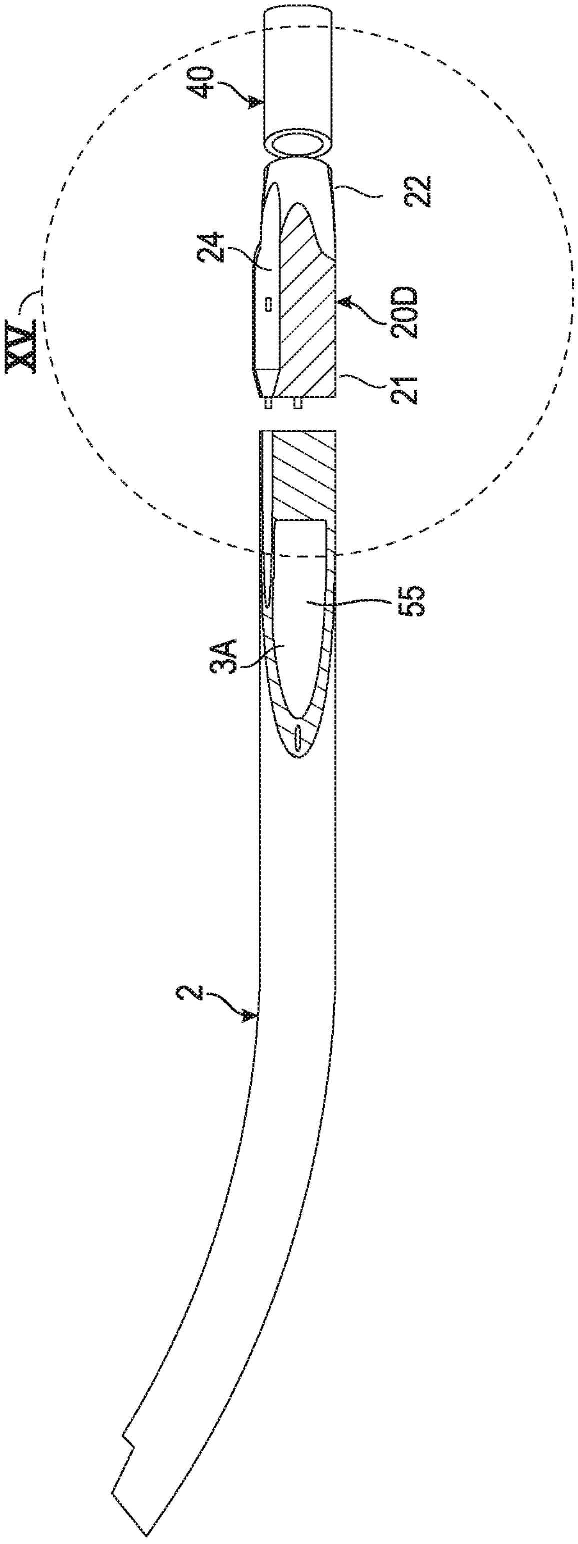
FIG. 12 is an exploded sectional view taken along the line XIV-XIV of FIG. 11.

FIGS. 11 to 20 illustrate an embodiment of the medical device 1 depicted in FIG. 1 with the cuffs removed for clarity. The distal tip 20D differs from the distal tip 20 in that it comprises a second lumen extension 52B and other features related thereto. As indicated with reference to FIG. 1, the medical device 1 includes a second lumen 52 comprised of a main tube second lumen 52A, the second lumen extension 52B, and a distal tube lumen 52C. The main tube second lumen 52A is enclosed by the outer wall 7, and the tip housing 20D forms the second lumen extension 52B. A distal tube 40 is mounted on the distal end 22 of the tip housing 20D, thereby forming a distal tube second lumen extension 52C enclosed by an outer wall 42 of the distal tube 40. The distal tube 40 may have different properties than the main tube 2 whereby more design freedom may be achieved. The distal tube 40 may preferably be an extruded tube. For instance, the distal tube 40 may be more flexible than the main tube 2 and may at least be more flexible than the tip housing 20D. However, alternatively, the distal tube 40 could be replaced by an integrated part of the tip housing 20D. Such integrated part of the tip housing 20D and the tip housing itself could be produced together from two different materials, respectively, by a co-injection molding technique, whereby the materials have different properties, such as different flexibilities. A sectional view along plane XIV is shown in FIG. 12.

Figure 13:
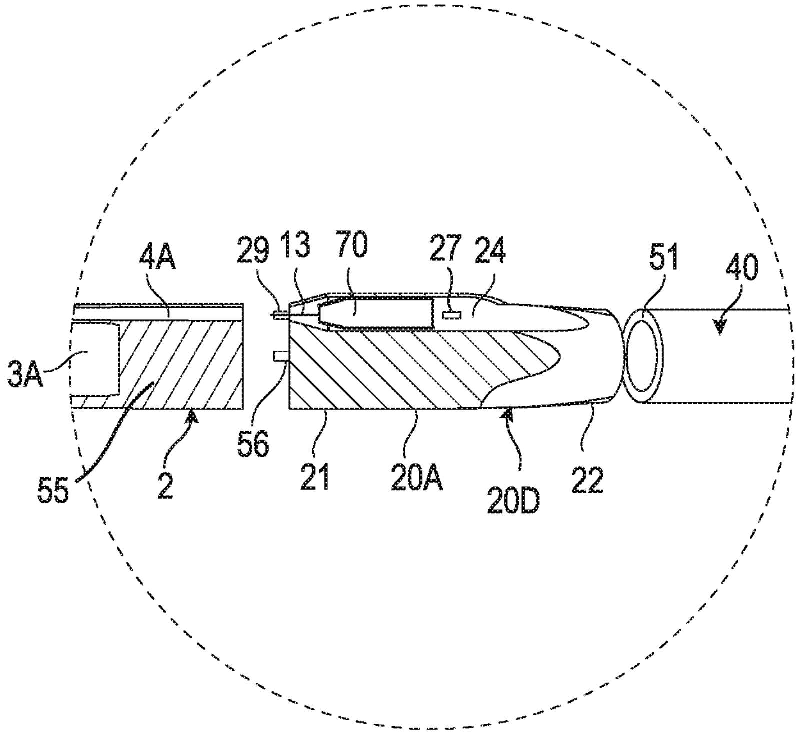
FIG. 13 shows, on a larger scale, the detail XV of FIG. 12.
Figure 14:
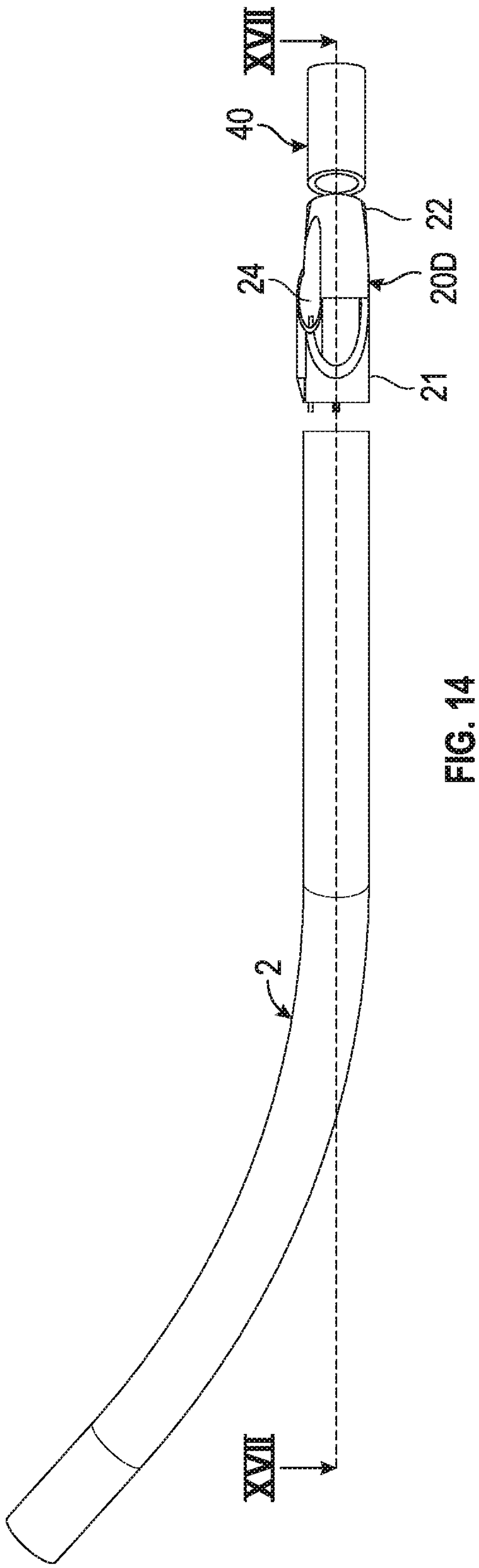
FIG. 14 is another side view of the double lumen endotracheal tube of FIG. 1, indicating a cross-section taken along the line XVII-XVII.
Figure 15:
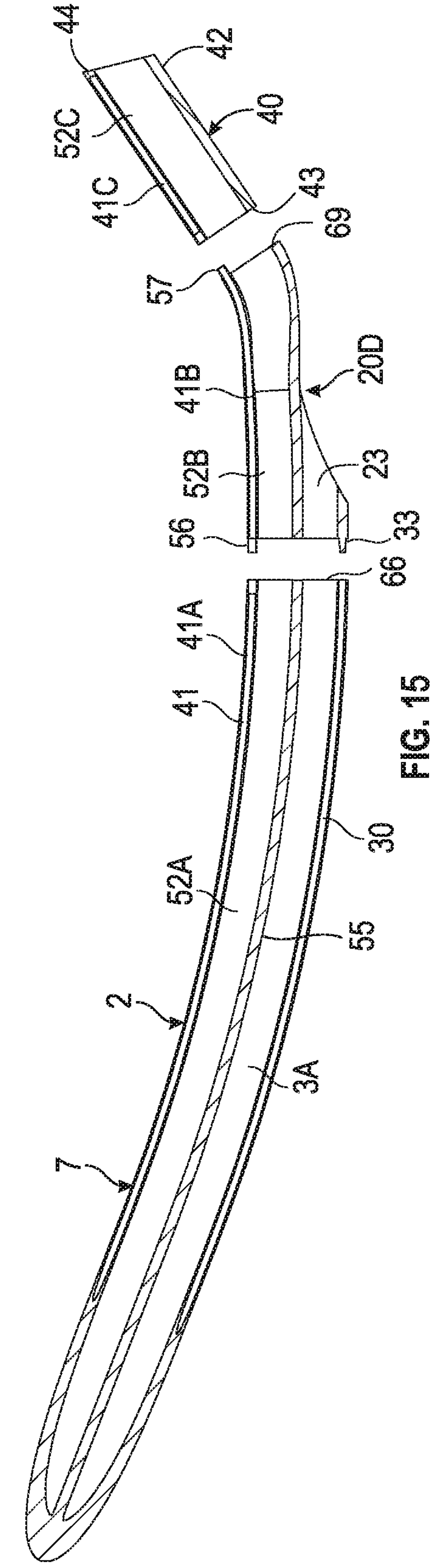
FIG. 15 is an exploded sectional view taken along the line XVII-XVII of FIG. 14.
Figure 16:
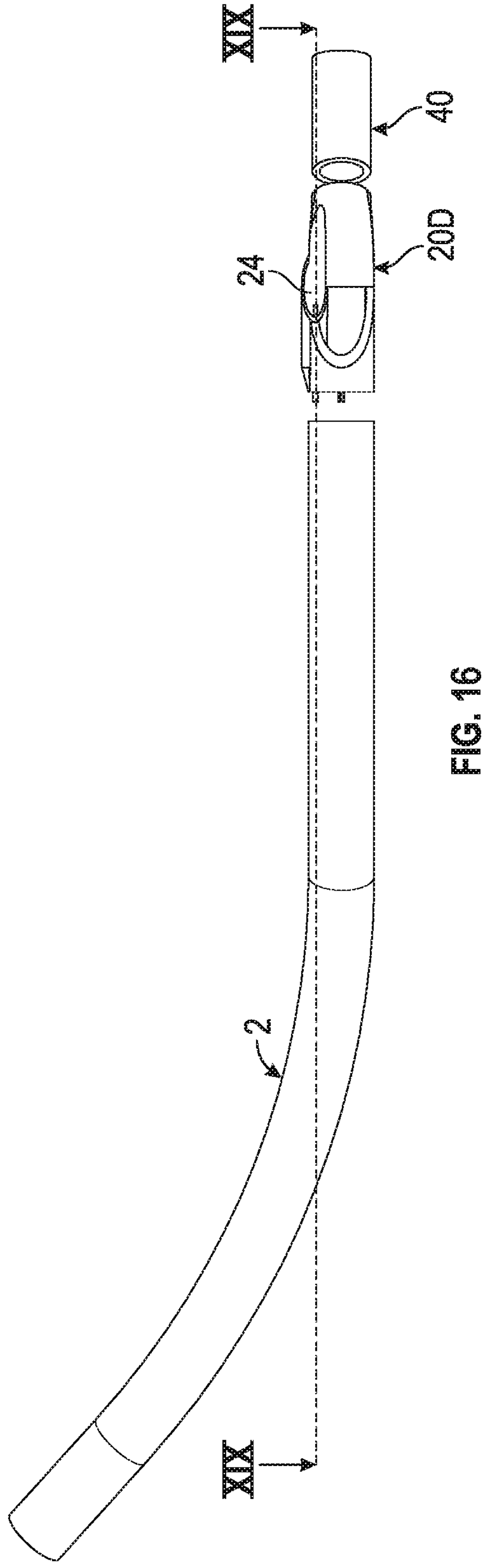
FIG. 16 is an exploded side view corresponding to that of FIG. 14 of the double lumen endotracheal tube of FIG. 1, indicating a cross-section taken along the line XIX-XIX.
Figure 17:
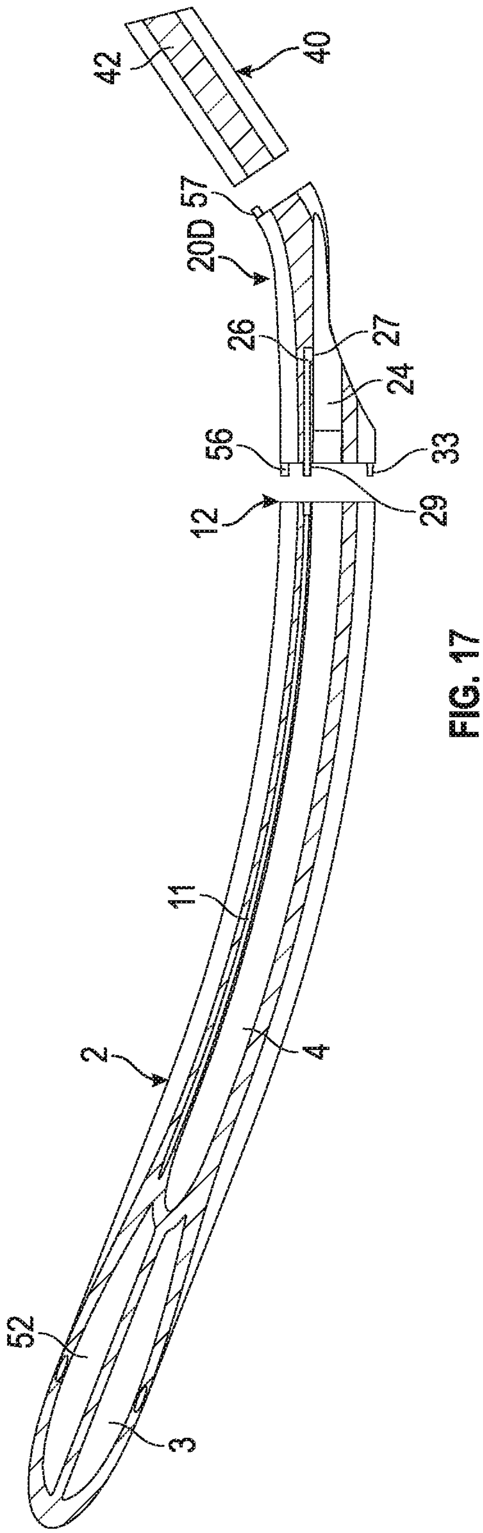
FIG. 17 is an exploded sectional view taken along the line XIX-XIX of FIG. 16.
Figure 18:
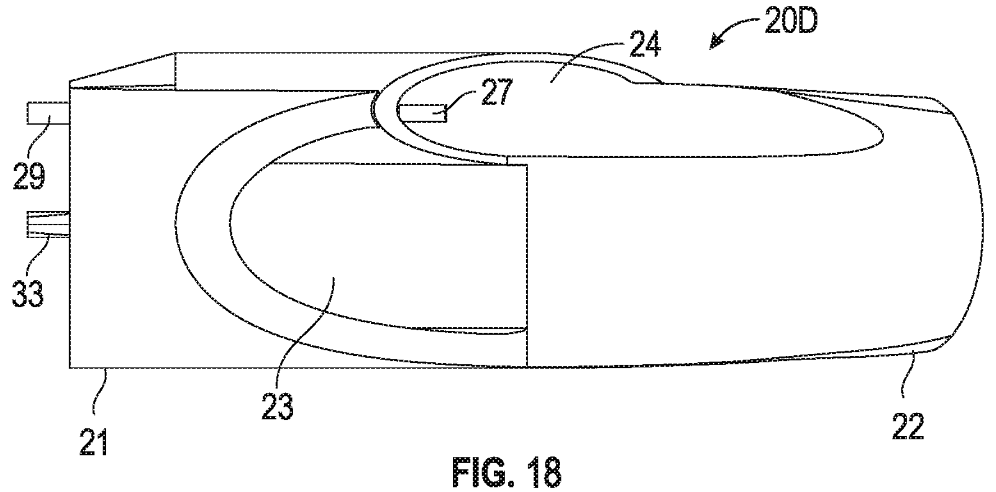
FIG. 18 is a side view of a tip housing of the double lumen endotracheal tube of FIG. 1.
Figure 19:
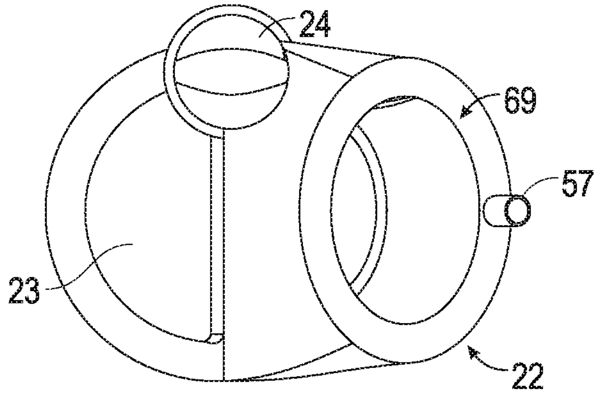
FIG. 19 is an end view of the tip housing of FIG. 18, seen from the right side of the figure.
Figure 20:
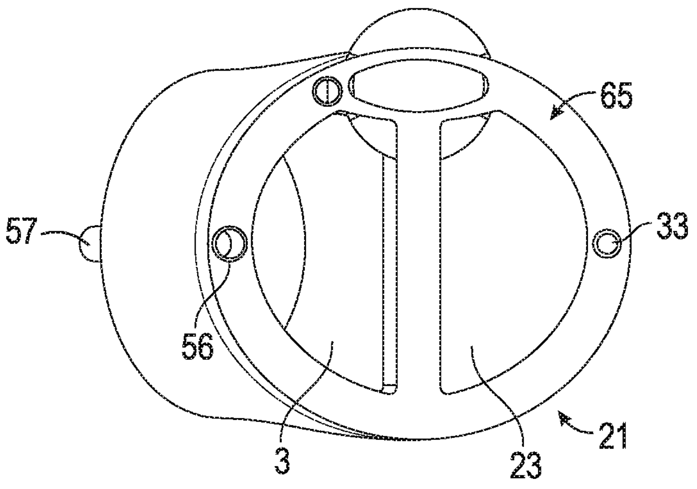
FIG. 20 is an end view of the tip housing of FIG. 18, seen from the left side of the figure.

FIG. 12 further illustrates the embodiment of the medical device 1 of FIG. 11. A distal portion XV is shown in FIG. 13. FIG. 13 shows a second cuff lumen pipe 56 and a schematic depiction of the camera housing 70. FIG. 14 shows an exploded view of the medical device 1 as shown in FIG. 1 and a plane XVII. FIG. 15 shows an exploded sectional view, along plane XVII, of the medical device 1 of FIG. 14. FIGS. 18-20 are side and end views of the tip housing of the double lumen endotracheal tube of FIG. 1. FIG. 19 is an end view seen from the right side of the figure. FIG. 20 is an end view of the tip housing seen from the left side of the figure.

Referring to FIG. 12, the outer wall 7 of the main tube 2 is generally ring-formed and surrounds the first lumen 3A and the second lumen 52A, and the camera lumen 4A is formed in the material of the outer wall 7 between an inner surface and an outer surface of the outer wall. As shown, the camera lumen 4A has a substantially smaller cross-section than the first lumen 3A and the second lumen 52A. For instance, when the camera housing 70 is inserted into the camera lumen 4A, the camera lumen 4A may at that position have a cross-sectional area being less than ½ or less than ⅓ of a cross-sectional area of the first lumen 3A or of the second lumen 52A. The first lumen 3A and the second lumen 52A are separated by means of a partition wall 55. As further seen, the camera lumen 4A is formed in the material of the outer wall 7 at a position where the partition wall 55 is connected to the outer wall 7. As also seen, the first lumen 3A and the second lumen 52A are generally symmetrically arranged about the partition wall 55 and in relation to the camera lumen 4A. The partition wall 55 is best seen in FIG. 15.

Referring to FIG. 15, the medical device 1 has a second cuff lumen 41 comprised by a main tube second cuff lumen 41A enclosed by the outer wall 7, a second cuff lumen extension 41B, and a distal tube second cuff lumen 41C enclosed by the outer wall 42 of the distal tube 40. The distal tube second cuff lumen 41C connects with the second inflatable cuff 60 in a not shown manner known per se, i.e. through an opening through the outer wall 42. An end opening 44 of the distal tube second cuff lumen 41C has been closed by means of a plug or the like. The second cuff lumen pipe 56 engages the main tube second cuff lumen 41A. A second cuff lumen pipe 57 is also provided at the distal end 22 of the tip housing 20D engaging the distal tube second cuff lumen 41C. Thereby, a continuous lumen without blockage in the junctions may be ensured. The protruding pipes 56, 57 may be manufactured as integrated parts of the tip housing 20D or may be separate pipe components inserted into the tip housing. The distal end 22 of the tip housing 20D has a distal junction interface 69 fitting an abutment surface 43 on the proximal end of the distal tube 40. The abutment surface 66 of the main tube 2 is also shown.

The tip housing 20, 20D can be joined to the main tube 2 and the distal tube 40 in a number of ways. FIGS. 21 to 24 illustrate grooves and protrusions that can be used to ensure a secure joint. Any of the embodiments and variations thereof described herein can be used to secure the tip housing 20, 20D to the main tube 2 and the distal tube 40. Because the tip housing 20, 20D is, preferably, injection molded, the protrusions or pipes for the joints will preferably extend from the tip housing 20, 20D toward the respective tube. The tube will, therefore, have widened openings configured to receive the protrusions/pipes. Some of the pipes for the various lumens were described above. Similar pipes can be used for any of the lumens.

Figure 21:
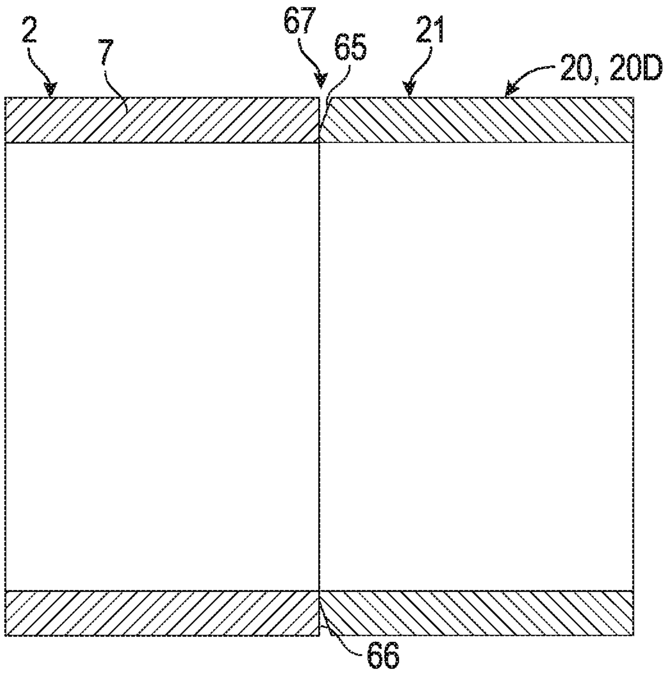
FIGS. 21 to 24 are schematic illustrations, seen in axial cross-section, of possible connections between the tip housing and a main tube of the endotracheal tubes of FIGS. 1 and 2.

FIGS. 21 to 24 illustrate embodiments of the junction interface between the proximal end 21 of the tip housing 20, 20D and an abutment surface 66 (shown in FIG. 15) of the main tube 2. FIG. 21 illustrates a proximal junction interface 65. The abutment surface 66 includes at least an end face of the outer wall 7 of the main tube 2. The proximal junction interface 65 comprises a groove 67 with said abutment surface 66 of the main tube 2. The groove 67 is adapted to take up glue or any applicable solvent in order to securely fuse together the housing 20 and the main tube 2.

Figure 22:
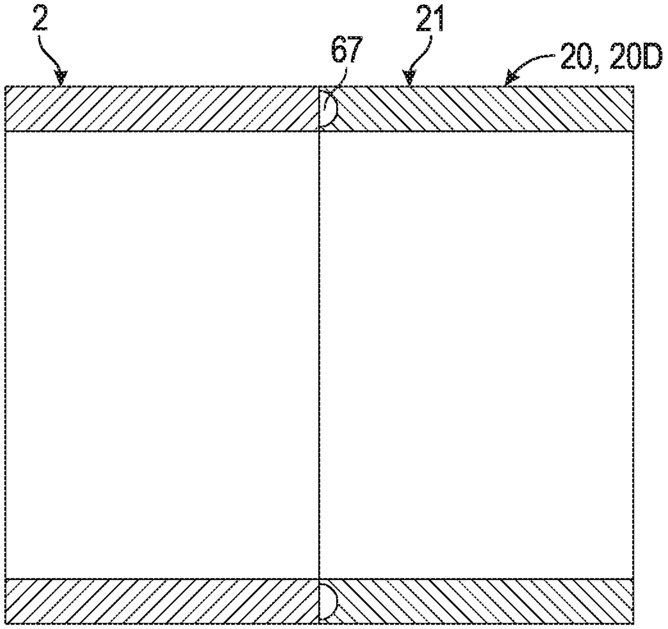

In the embodiment of FIG. 22, a groove is formed in the end face of the outer wall 7 (as shown) or the main tube 2. Adhesive is provided in the groove before joining the tip housing 20, 20D and the main tube 2.

Figure 23:
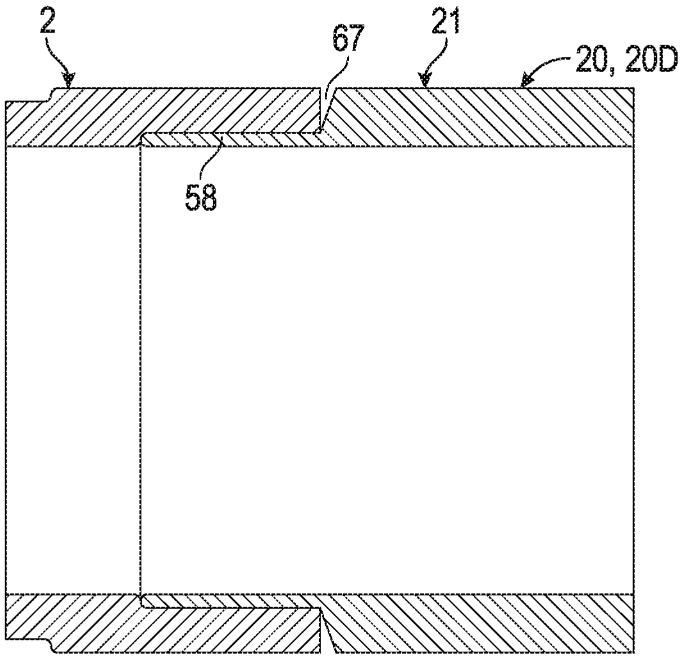

In the embodiment of FIG. 23, the proximal end 21 of the tip housing 20, 20D is provided with a protruding pipe 58 engaging the main tube first lumen 3A and/or the main tube second lumen 52A, as well as possibly the camera lumen 4A, of the main tube 2.

Figure 24:
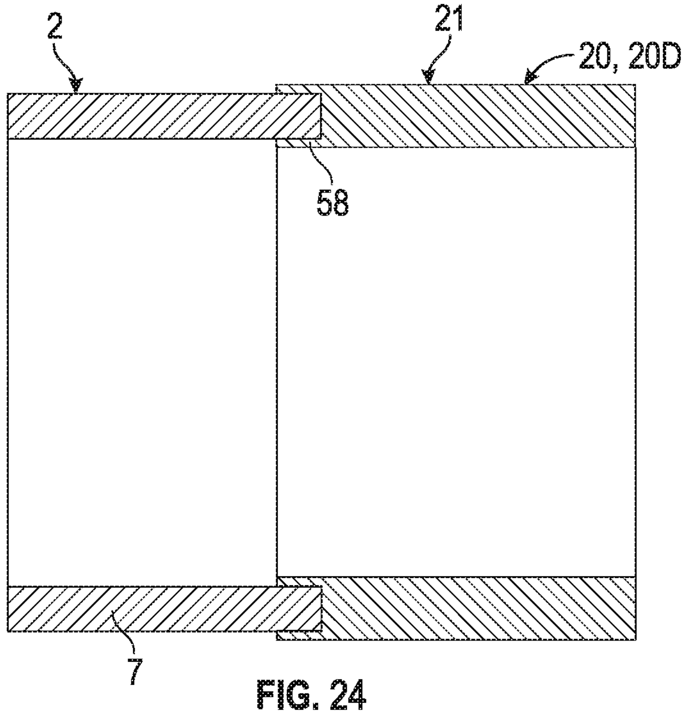

In the embodiment of FIG. 24, the proximal end 21 of the tip housing 20, 20D is provided with a groove 58 in which the outer wall 7 of the main tube 2 is inserted.

Referring again to FIG. 15, the distal end 22 of the tip housing 20D has a distal junction interface 69 fitting an abutment surface 43 on the proximal end 21 of the distal tube 40. Said abutment surface 43 includes an end face of the outer wall 42 of the distal tube 40. In a similar way as illustrated in FIGS. 21 to 24, the distal junction interface 69 may form a groove with said abutment surface 43 of the distal tube 40, wherein said groove may contain hardened glue. Furthermore in a similar way as illustrated in FIG. 23, the second lumen extension 52B may, at the distal end 22 of the tip housing 20D, be provided with a protruding pipe engaging the distal tube second lumen extension 52C.

The main tube 2 may be made extruded from rubbers, e.g. butyl rubber, natural rubber or nitrile rubber, latex, neoprene, isoprene, polymers and/or silicone materials. The endotracheal tube may be made of Poly vinyl chloride (PVC) (with plasticizer), Thermoplastic elastomer (TPE), e.g. Styrene ethylene butylene styrene (SEBS), Styrene butylene styrene (SBS), Thermoplastic Polyurethanes (TPU) or Thermoplastic vulcanizates (TPV). Most TPVs are binary blends of polyolefins and thermoplastic diene elastomers. Other elastomers sometimes used in TPVs include butyl rubber, natural rubber or nitrile rubber blended with iPP. Alternatively, blends of one or more of these materials may be used for producing the medical device, such as a catheter or endotracheal tube.

Figure 25:
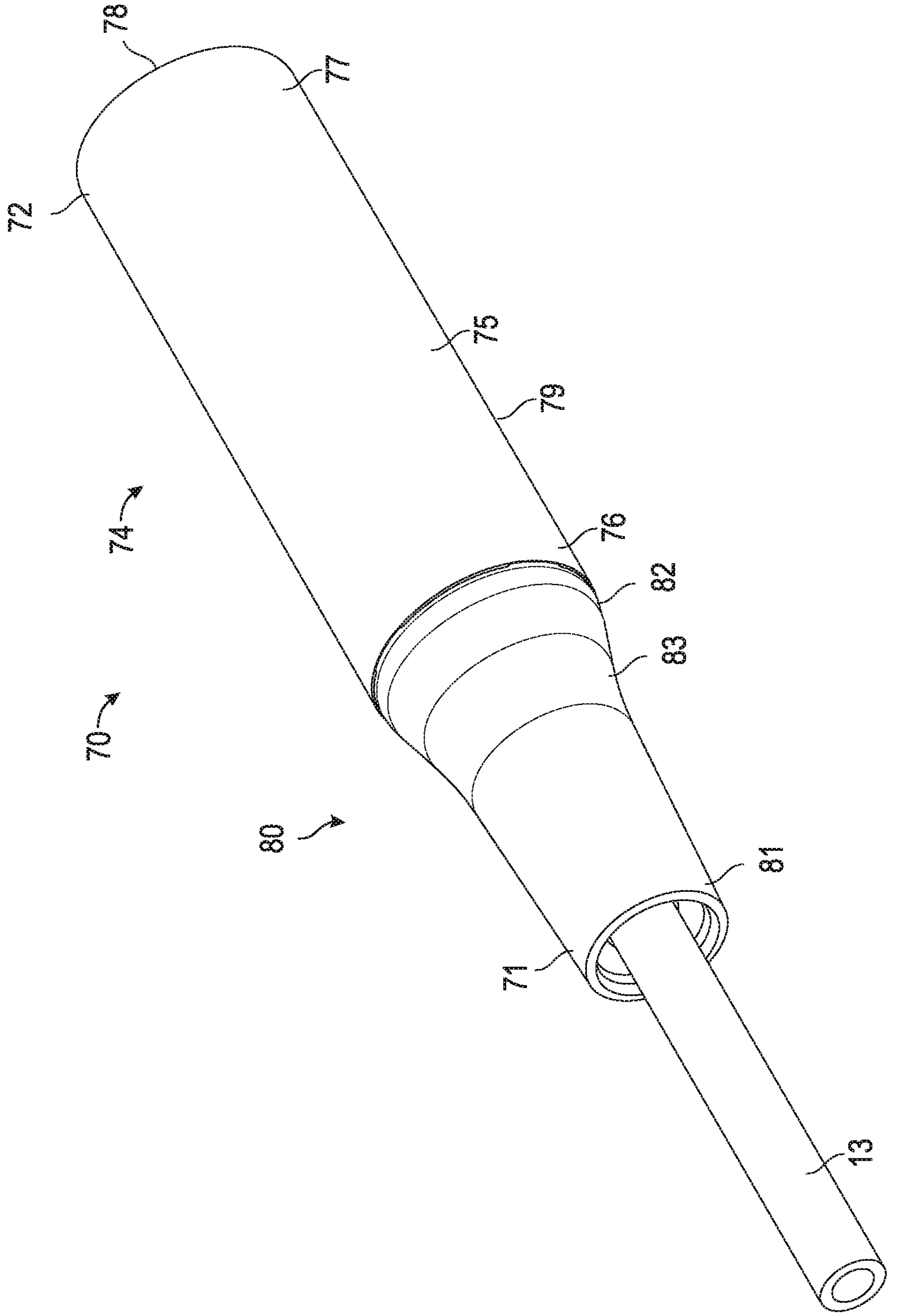
FIG. 25 is a perspective view of an embodiment of an assembled camera module and housing for the endotracheal tubes of FIGS. 1 to 24.

FIGS. 25 to 41 illustrate features of the camera module 10 and an embodiment of a camera housing, denoted by numeral 70. Referring to FIG. 25, the camera housing 70 extends in a longitudinal direction and has a proximal end 71 and a distal end 72. The camera housing 70 includes a housing element 74 and a proximal portion 80. The housing element 74 comprises a tubular housing part 75 integrally molded and forming one single part with a distal end wall 78. The tubular housing part 75 extends between a proximal end 76 and a distal end 77 of the housing element 74. The tubular housing part 75 comprises a circumferential wall 79 at least partly surrounding the camera module 10. The tubular housing part 75 fits tightly into the camera lumen extension 24 of the medical device 1. A tight fit between the tubular housing part 75 and the camera lumen extension 24 may ensure precise positioning of the camera module 10 in the medical device 1 without any adjustments being necessary. Thereby, production may be made easier and faster with less individual steps. In particular, dilatation of the camera lumen 4A in order to mount the camera module 10 in the camera lumen may not be necessary. Although it may be preferred that the tubular housing part 75 has a circular cross-section as illustrated in the figures, any tubular form is possible. For instance, the cross-section of the tubular housing part 75 may have any suitable rounded form, such as oval or elliptic. The cross-section of the tubular housing part 75 may also have other forms, such as polygonal form, in particular a triangular, square, rectangular, pentagonal, hexagonal, heptagonal, or octagonal form or any suitable form.

The proximal portion 80 is arranged at the proximal end 76 of the tubular housing part 75 and includes a proximal end 81 and a distal end 82 and a tapering part 83 arranged between the proximal end 81 and the distal end 82. The tapering part 83 may for instance be conical. In the illustrated embodiment, the tapering part 83 is composed of a number of sections having varying configuration. An outer diameter of the proximal end 81 is smaller than an outer diameter of the distal end 82. Furthermore, the outer diameter of the distal end 82 of the proximal portion 80 corresponds to an outer diameter of the tubular housing part 75. Thereby, a smooth transition between the proximal portion 80 and the tubular housing part 75 may be ensured. The tapered part of the proximal portion 83 may make it much easier to push the camera housing 70 into the camera lumen 4A of the tube which may be made of a soft/flexible polymer material. Thereby, dilatation of the camera lumen 4A of the tube in order to mount the camera module 10 in the camera lumen may be even less necessary. It is noted that the outer surface of the tubular housing part 75 itself may also taper or may be slightly conical in order to facilitate insertion of the camera housing 70 into the camera lumen extension 24 and the camera lumen 4A of the main tube 2. The proximal portion 80 is formed as a separate element attached to the tubular housing part 75, usually by means of glue.

Figure 26:
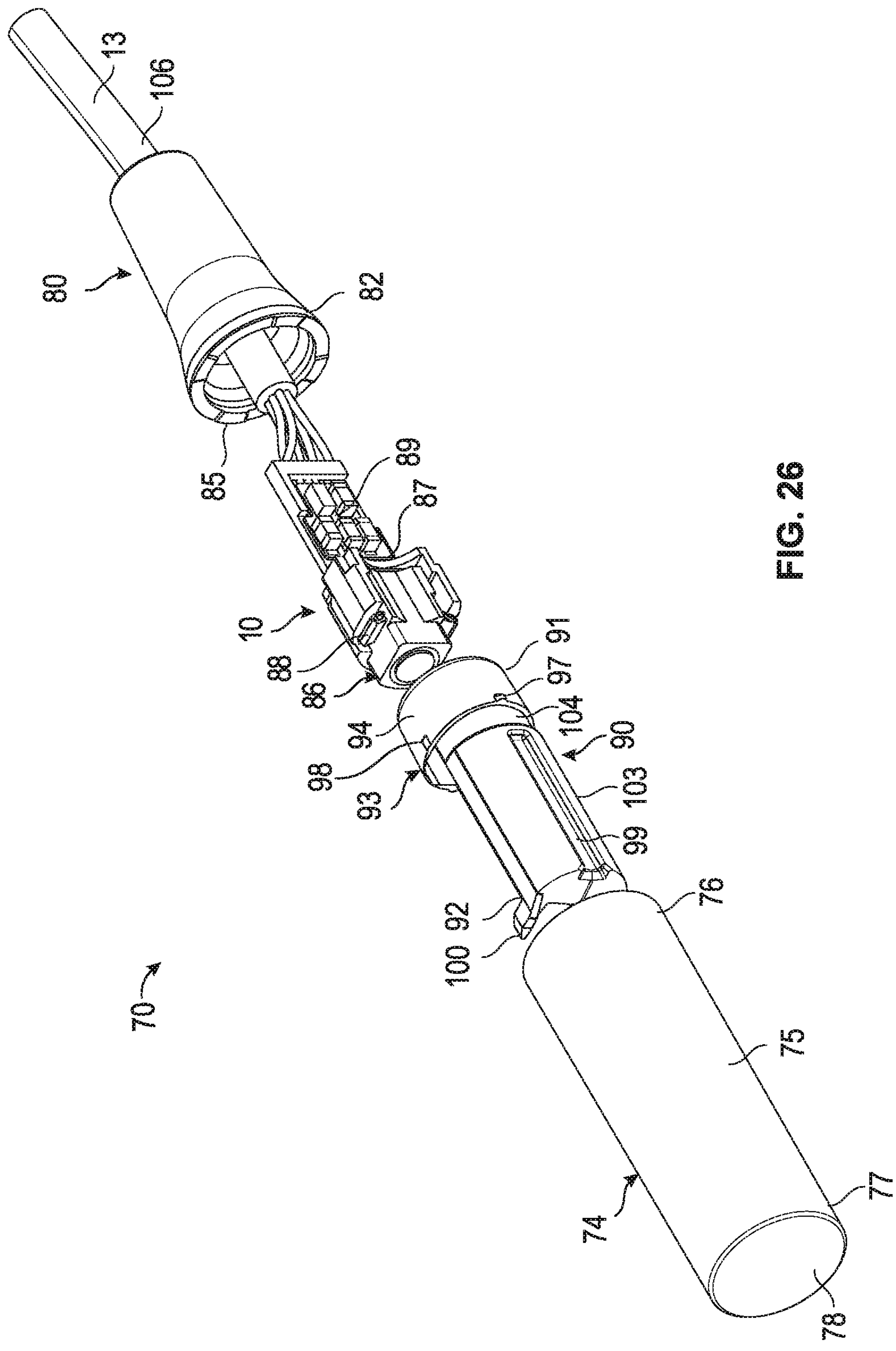
FIG. 26 is an exploded perspective view of the camera module and housing of FIG. 25.

FIGS. 26 to 33 show different views of the camera module 10 and the camera housing 70. Referring to FIG. 26, the distal end 82 of the proximal portion 80 may have a number of protrusions 85 distributed in its circumferential direction and adapted to abut the proximal end 84 of the tubular housing part 75. The camera module 10 includes a camera having lens barrel 86 and an image sensor 87 (also shown in FIG. 33), and one or more light sources 88 in the form of one or more LED's or incandescent bulbs. The lens barrel 86 includes one or more lenses, referred to as a lens stack. The image sensor 87 is positioned proximally of the lens barrel 86. Furthermore, the light sources may be provided in the form of one or more fiber optic cables transmitting light from outside the camera module 10 to the camera module 10. A circuit board 89 including electronic components extends proximally of the image sensor.

A support structure 90 for the camera module 10 (best seen in FIGS. 27 and 28) has a proximal end 91 and a distal end 92, and the proximal end 91 has a tubular end part 93 arranged inside the tubular housing part 75 of the camera housing 70. The image transmission cable 13 extends through the tubular end part 93, and the distal end 92 of the support structure is engaged with the camera module 10. The tubular end part 93 has an outer face 94 being glued to an inner face 95 (shown in FIG. 33) of the tubular housing part 75 of the housing element 74. The outer face 94 may be conical so that a gap 110 (shown in FIG. 33) for glue is formed which has a cross-section generally decreasing in the direction from the proximal end 91 to the distal end 92 of the support structure 90. Thereby, correct application of glue may be ensured. Capillary effects may ensure that glue enters the gap and the decreasing cross-section of the gap may serve to avoid that glue enters too far inside of the camera housing 70. Furthermore, the outer face 94 of the tubular end part 93 of the support structure 90 is provided with a number of ribs 97, 98 (best seen in FIGS. 27, 28, and 32) distributed in the circumferential direction of the outer face 94 in order to center the support structure inside the camera housing such that the two parts can be glued together by utilizing capillary effects. As seen, the ribs 97, 98 only extend at a distal end of the tubular end part 93 of the support structure 90 in order to facilitate entrance of glue into the gap. A longitudinal groove 99 is shown. A guide rib (described below) is adapted to slide in the groove 99 to ensure that the camera module 10 is guided to the correct rotational orientation inside the camera housing 70. Spaced tabs 100 are also shown, which are discussed below. The support structure 90 includes an elongated part 103 having generally semi-circular cross-section, and the elongated part 103 connects the proximal end 91 of the support structure 90 with the two spaced tabs 100. The elongated part 103 is provided with a peripherally extending recess 104 facing the inner face 95 of the tubular housing part 75 of the camera housing 70 next to the tubular end part 93 of the support structure 90 in order to stop the glue from moving further into the camera housing during application. The image transmission cable 13 has an outer face 106.

Figure 27:
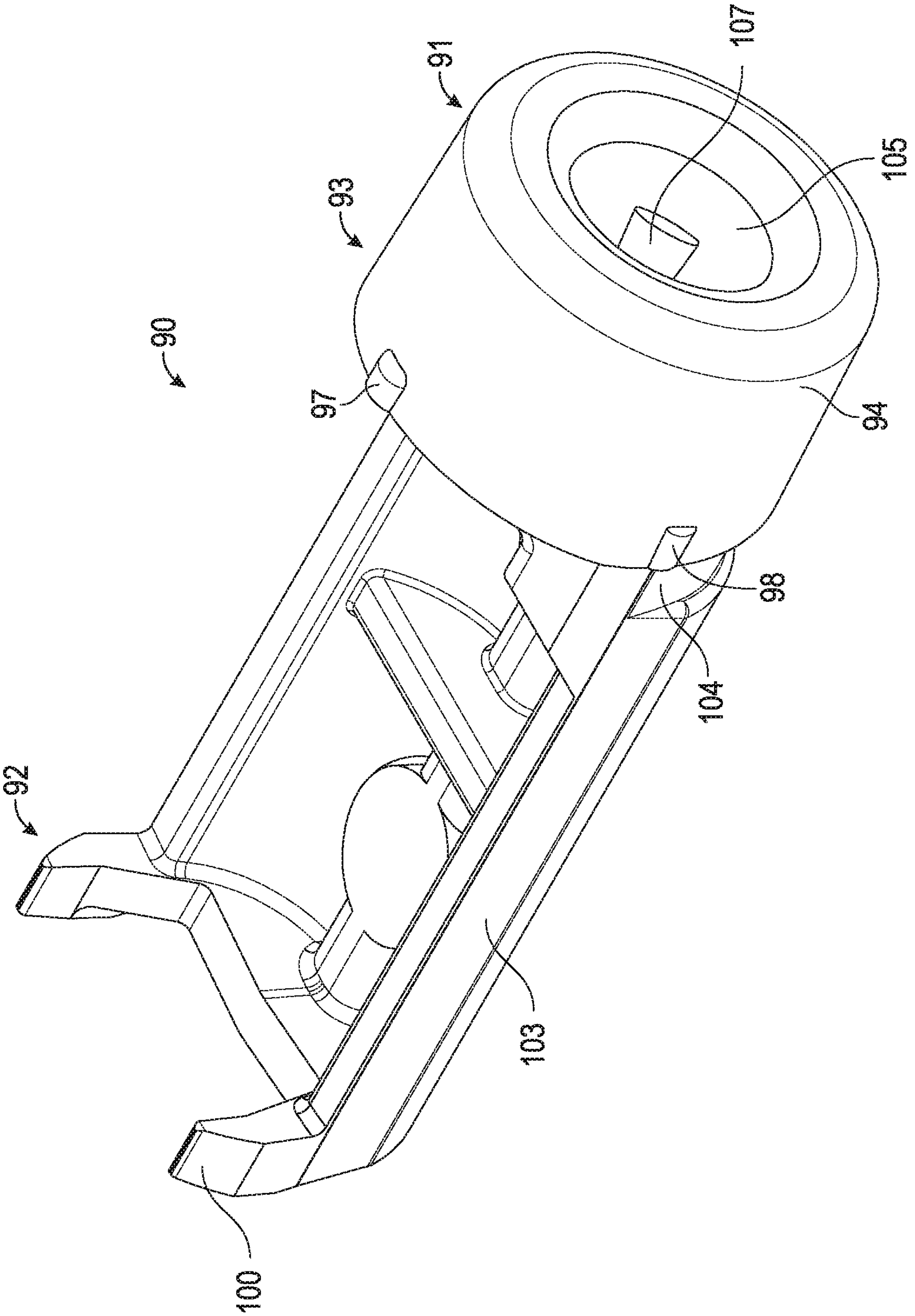
FIG. 27 is a perspective view of a support structure for the camera module.
Figure 28:
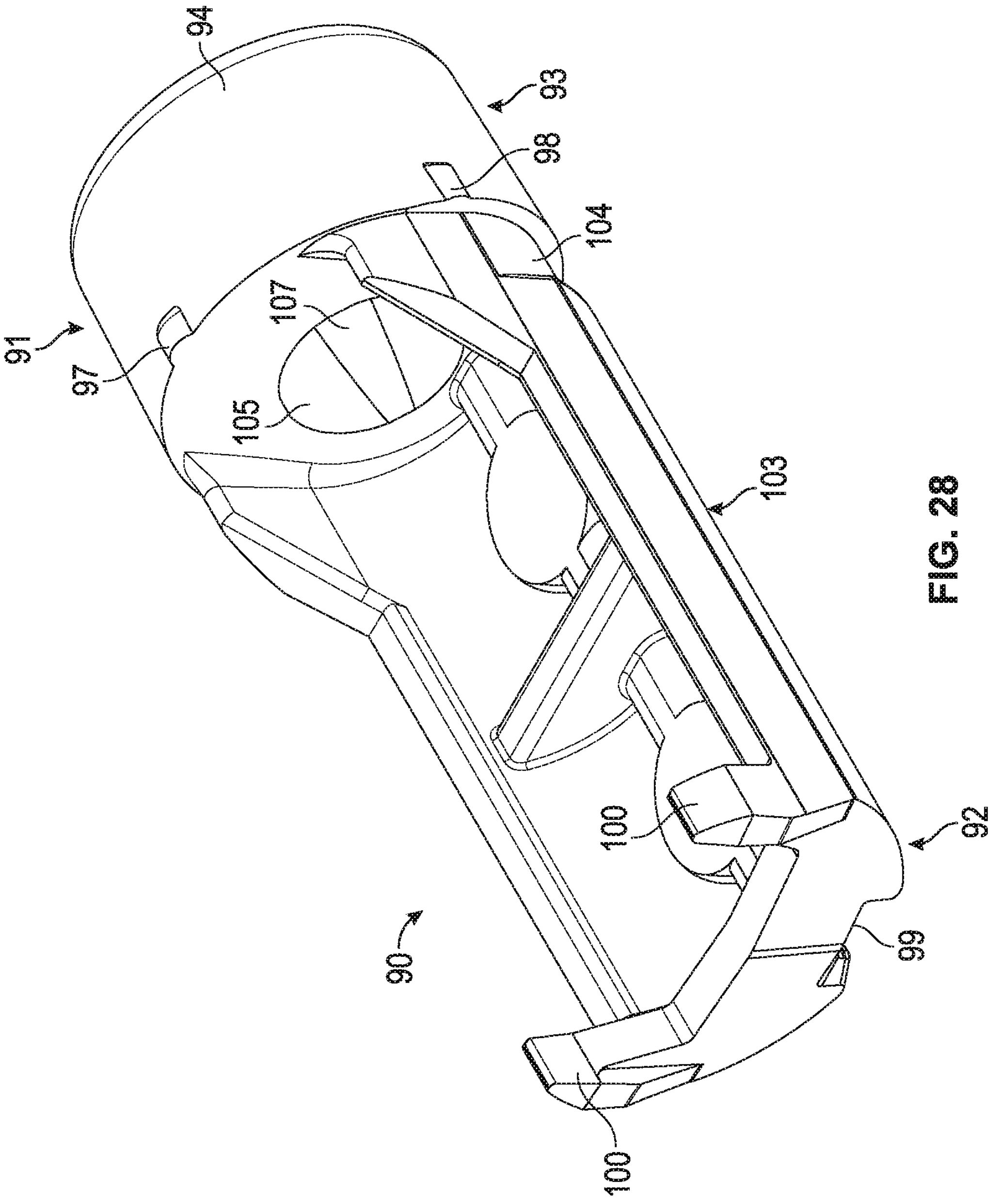
FIG. 28 is a perspective view of the support structure seen from another point of view.
Figure 29:
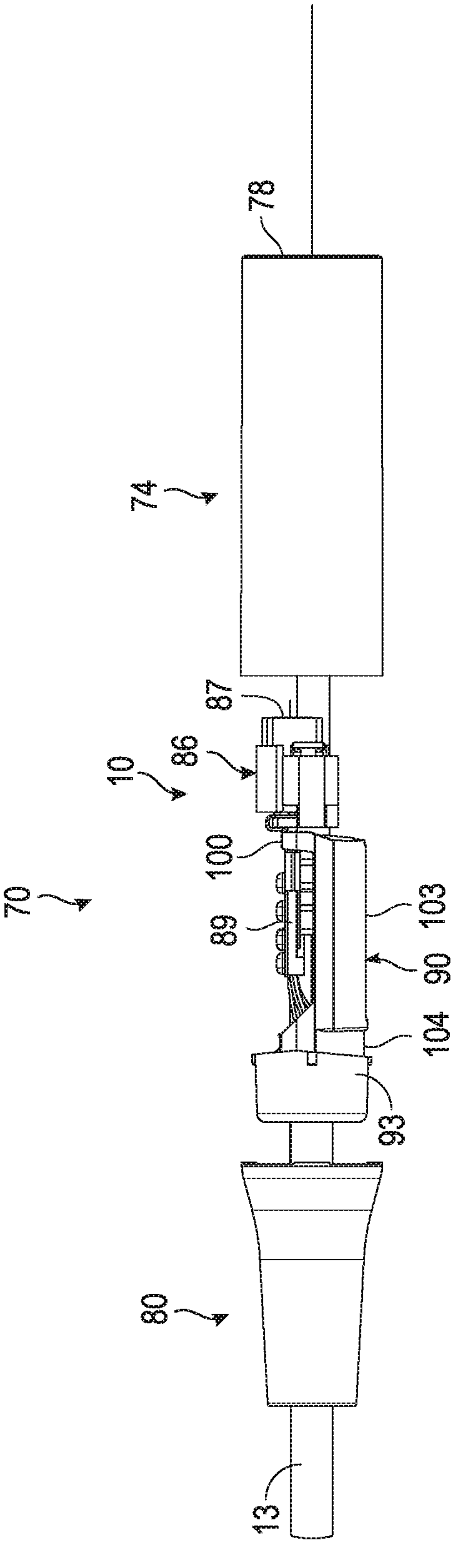
FIG. 29 is a side view of the camera housing of FIG. 26, before insertion of the camera module into the camera housing.
Figure 30:
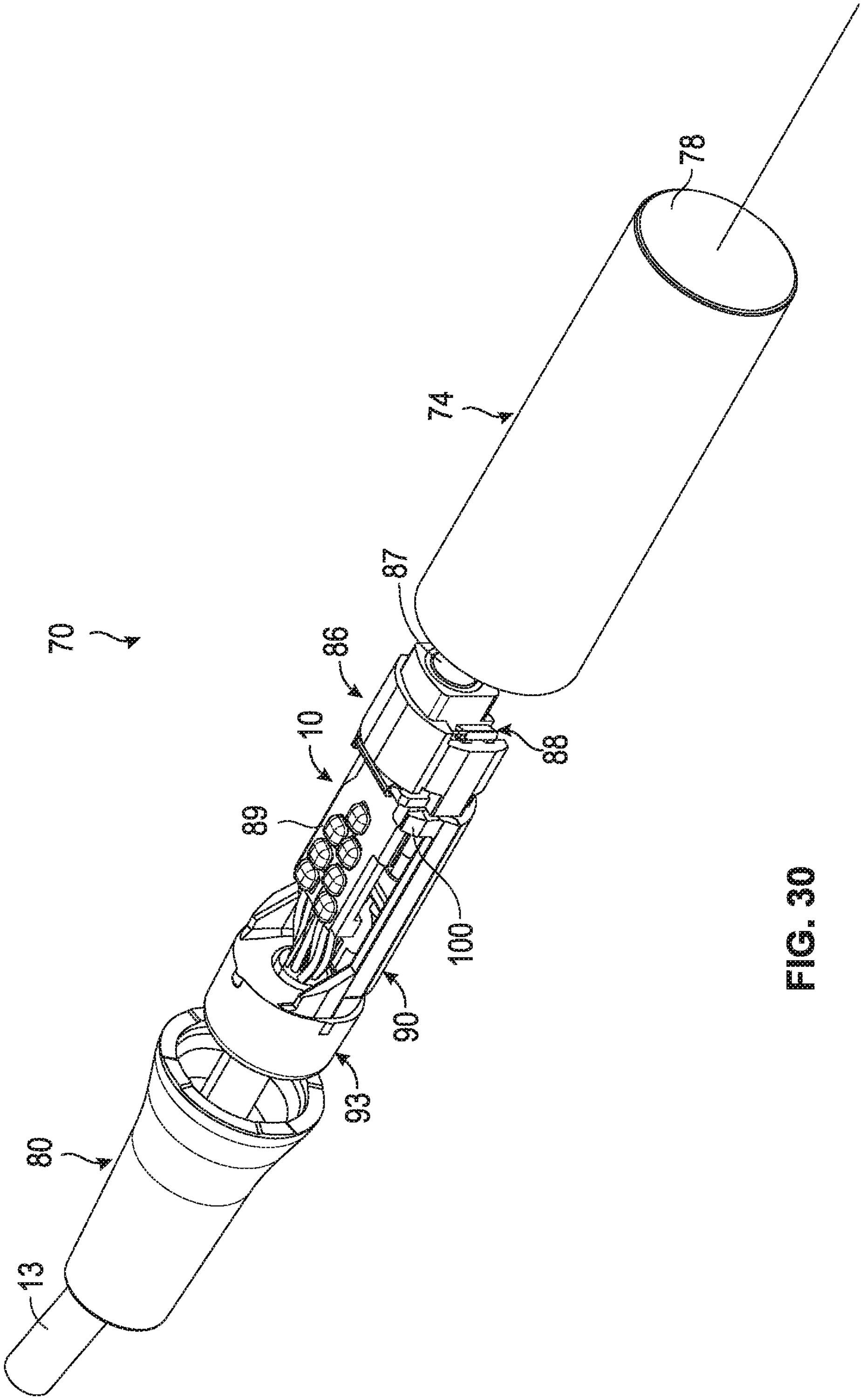
FIG. 30 is a perspective view corresponding to that of FIG. 29.
Figure 31:
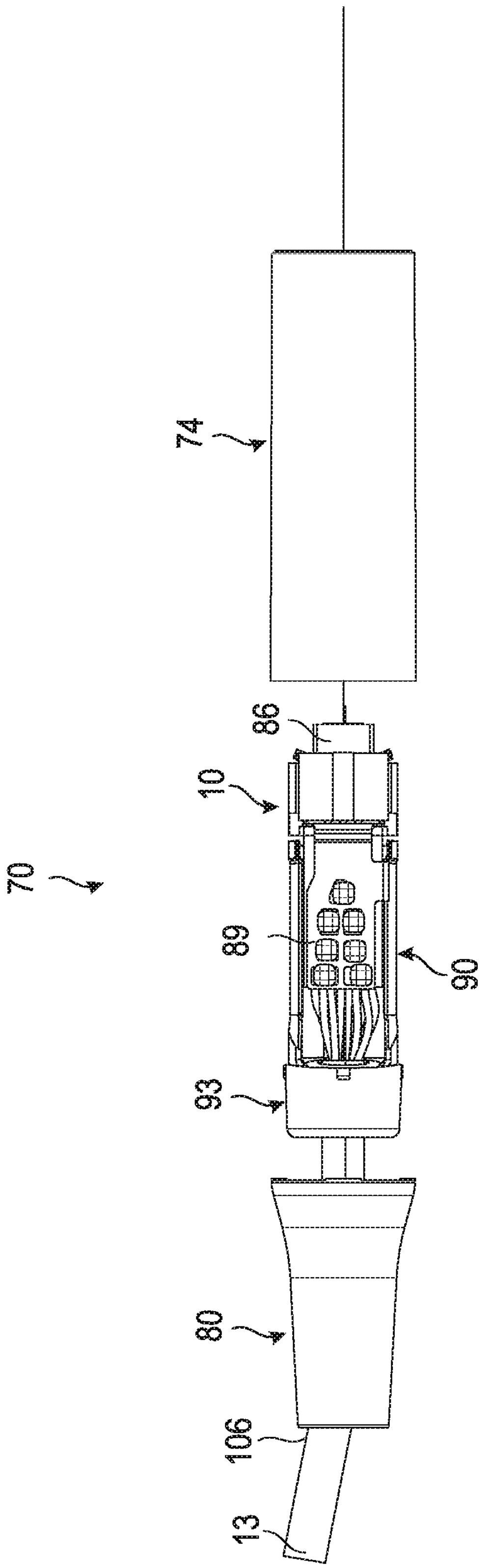
FIG. 31 is a view corresponding to that of FIG. 29, show as a top view.

FIGS. 27 and 28 are perspective views of the support structure 90 for the camera module 10. FIGS. 29, 30, and 31 are side, perspective, and top exploded views of the camera module 10 and the camera housing 70.

Figure 32:
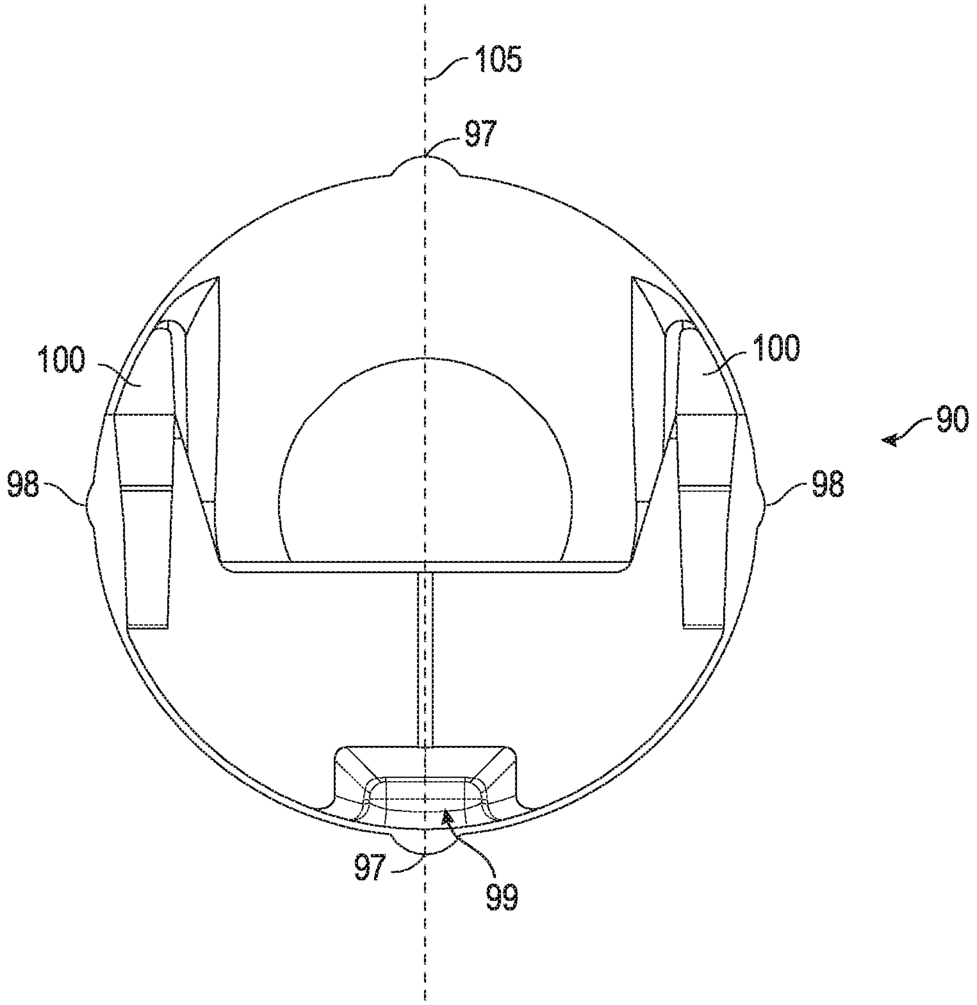
FIG. 32 is an end view of the support structure of a camera module from a distal end thereof.

FIG. 32 is a cross-section view of the support structure 90 showing the ribs 97, 98, the longitudinal groove 99, and the spaced tabs 100. The ribs 97, 98 include two pivot forming ribs 97 arranged diametrically opposite of the tubular end part 93 of the support structure 90. Together the two pivot forming ribs 97 provide a relatively tight fit with the corresponding inner face 95 (shown in FIG. 33) of the tubular housing part 75 of the camera housing 70. Furthermore, said ribs 97, 98 include a number of distance ribs 98 distributed peripherally about the tubular end part 93 of the support structure 90 and together they provide a relatively loose fit with the corresponding inner face 95. The two pivot forming ribs 97 protrude longer in the radial direction than the distance ribs 98. By this arrangement of the ribs 97, 98, it may be ensured that the support structure 90 may pivot about an axis generally extending through said pivot forming ribs 97 during the insertion of the support structure 90 into the tubular housing part 75 of the camera housing 70. Thereby, the distal end of the support structure 90 may better engage the camera module 10 in a flexible way so that the camera module may be guided into its correct position in the camera housing.

The two spaced tabs 100 are arranged generally symmetrically about a plane 105 extending through said two pivot forming ribs 97, and the two spaced tabs 100 are adapted to abut the camera module 10 as seen in FIG. 30. Thereby, both spaced tabs 100 may tend to engage the camera module 10 during its insertion into the camera housing, preventing lateral movement, thereby even better ensuring that the camera module may be guided into its correct position.

Figure 33:
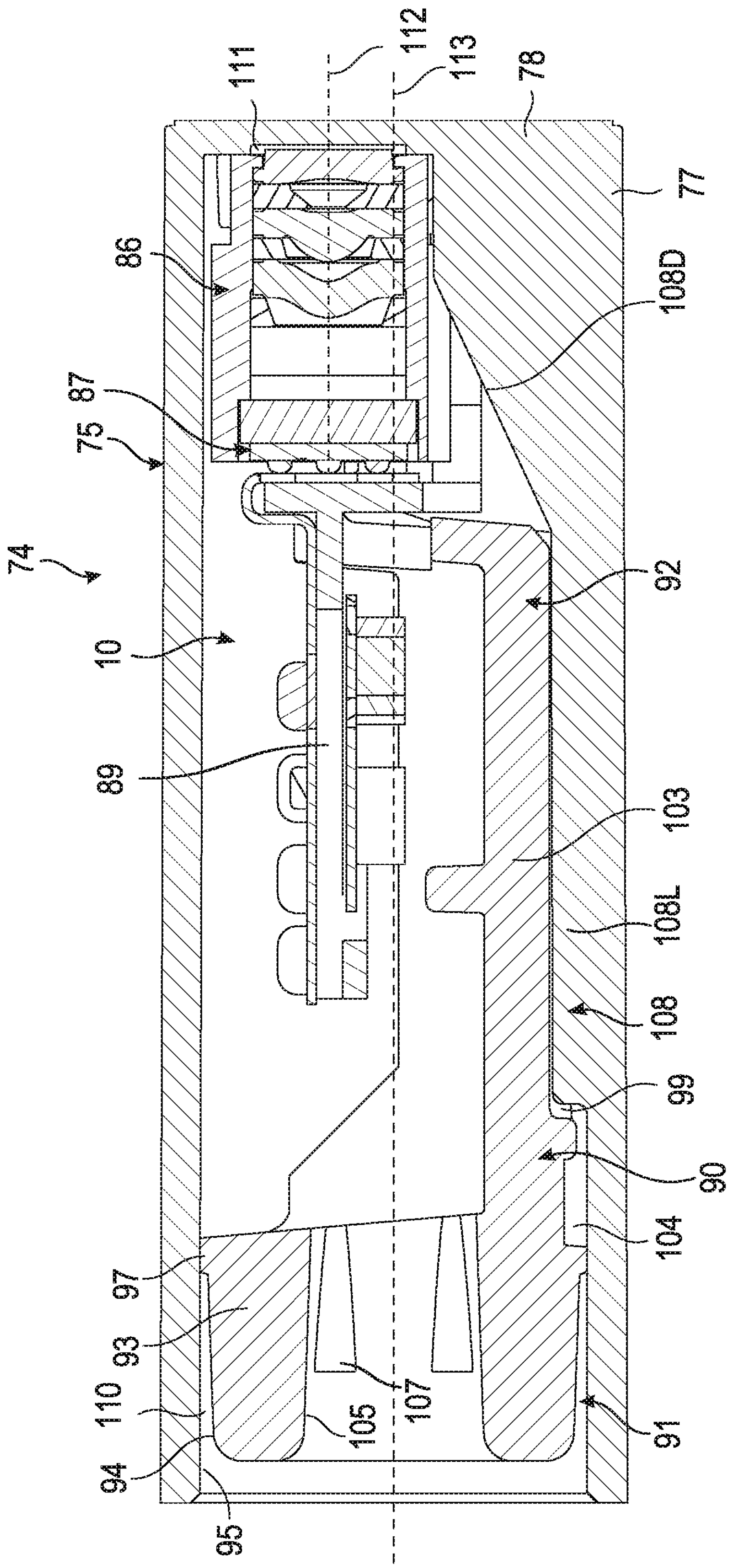
FIG. 33 is an axial section through the assembled camera housing of FIG. 25, however without the image transmission cable and the tapering proximal part.

FIG. 33 shows a sectioned view of the assembled camera housing 70 and camera module 10. The tubular end part 93 of the support structure 90 has an inner face 105 being glued to the outer face 106 of the image transmission cable 13. The inner face 105 of the tubular end part 93 of the support structure 90 is conical so that a gap for glue is formed which has a cross-section generally decreasing in the direction from the proximal end 91 to the distal end 92 of the support structure 90 in order to ensure correct application of glue. Capillary effects may ensure that glue enters the gap and the decreasing cross-section of the gap may serve to avoid that glue enters too far inside of the camera housing. In the illustrated embodiment, the inner face 105 of the tubular end part 93 of the support structure 90 is further provided with a number of ribs 107 distributed in the circumferential direction of the inner face 105 in order to ensure that image transmission cable is centered inside the tubular end part of the support structure.

The inner face 95 of the tubular housing part 75 of the camera housing 70 has a guide rib 108 extending in the longitudinal direction of the camera housing 70, and the support structure 90 has the longitudinal groove 99, wherein the guide rib 108 is adapted to slide in the groove 99 in order to ensure that the camera module 10 is guided to the correct rotational orientation inside the camera housing 70. The groove 99 is arranged symmetrically about the plane 105 extending through said two pivot forming ribs 97, and the guide rib 108 has a loose fit in the groove 99 in order to better ensure that the support structure 90 may pivot about an axis generally extending through said pivot forming ribs 97 during the insertion of the support structure into the tubular part of the camera housing. Thereby, the distal end of the support structure may better engage the camera module 10 in a flexible way so that the camera module may be guided into its correct position in the camera housing.

The camera module 10 is arranged extending from the distal end 92 of the support structure 90. The inner face 95 of the tubular housing part 75 of the camera housing 70 is provided with the guide rib 108, which has a longitudinal portion 108L and a wedge portion 108D. The wedge portion 108D wedge-formed at the distal end 77 of the camera housing 70 in order to guide the camera module 10 into its correct position during the last part of the insertion procedure. The distal end wall 78 of the camera housing 70 has a recess 111 in which at least a portion of a lens barrel 86, or a lens contained therein, of the camera module 10 is inserted. At least the part of the distal end wall 78 forming the recess 111 is formed in a material which is transparent. Possibly, the transparent part of the end wall 78 may be co-molded with material not being transparent which may form a remaining part of the end wall 78. The lens barrel 86 of the camera module 10 may for instance include a lens stack and a barrel housing carrying and/or enclosing the lens stack. The lens barrel 86 has a central axis 112. The tubular housing part 75 has a central axis 114.

The tubular housing part 75 of the camera housing 70 has a cylindrical circumferential wall 79 having a central axis 113 of symmetry, and a lens barrel 86 of the camera module 10 is eccentrically arranged in relation to the cylindrical outer surface of the tubular housing part. The central axis 112 of the lens barrel 86 of the camera module is displaced in relation to the central axis 113 of symmetry of the cylindrical circumferential wall 79 of the tubular housing part 75 of the camera housing 70 so that the lens barrel 86 is closer to the first lumen 3 than to the second lumen 52. Thereby, it may be ensured that the viewing angle of the camera module 10 covers relatively more of the surroundings of the main tube 2 than it covers of the part of the tube enclosing the second lumen 52 distally of the first lumen 3. Thereby, it may be ensured that the image captured by the camera module 10 shows more of the anatomy and less of the tubing of the second bronchial lumen 52 provided with the second inflatable cuff 60 which is inserted into the bronchus. The central axis 113 of symmetry may lay on a plane passing through the partition wall 55.

As an alternative to the recess 111, the distal end wall 78 may be provided with a through-hole wherein the lens barrel of the camera module is positioned. The camera module would then need to be glued and sealed towards the edge of the through-hole.

Figure 34:
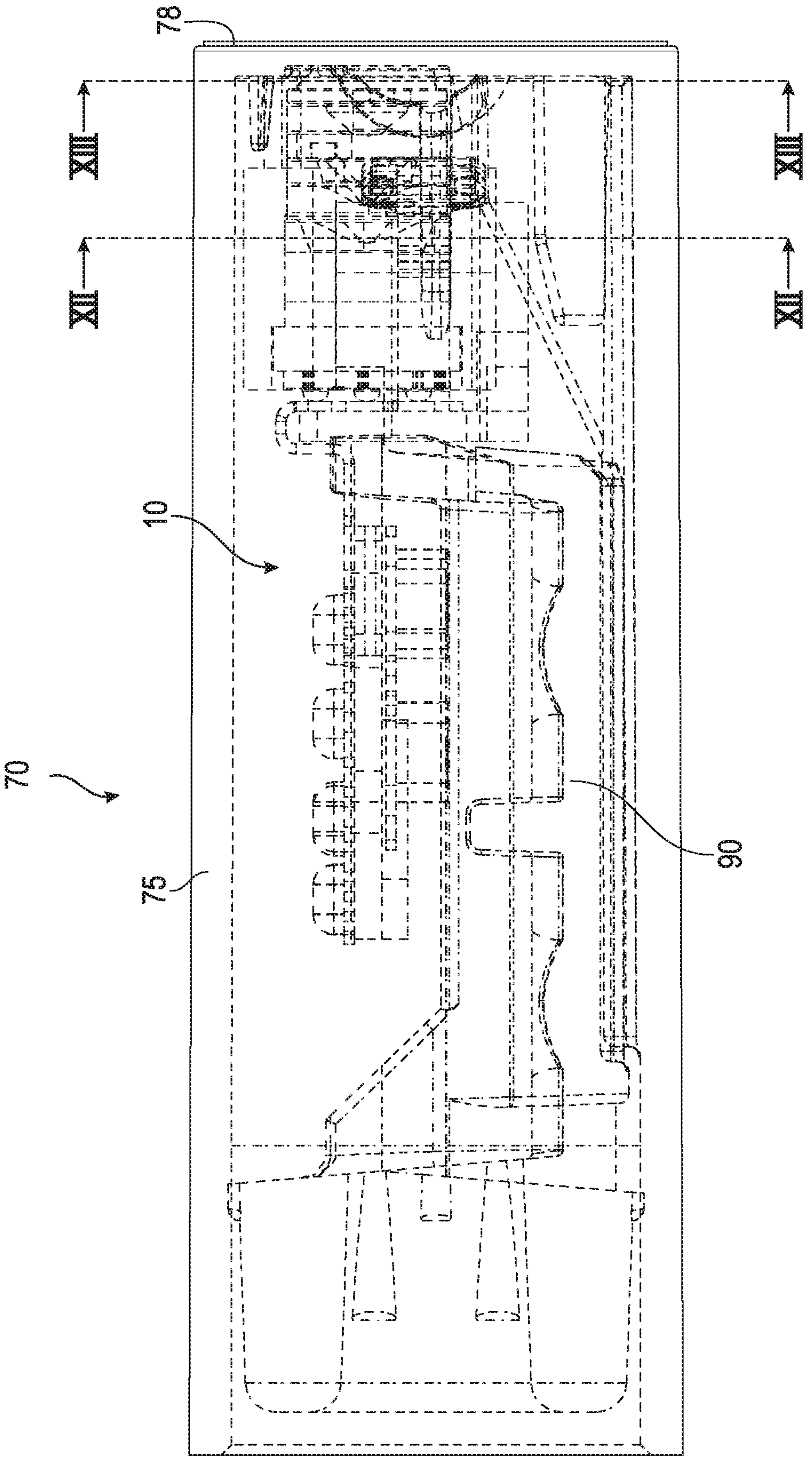
FIG. 34 is a side view of the assembled camera housing of FIG. 25, however without the image transmission cable and the tapering proximal part, with indications of sectional views.
Figure 35:
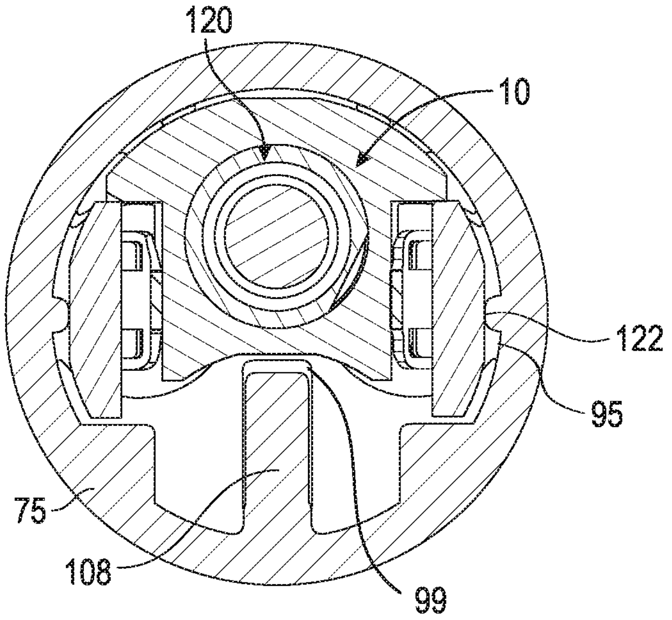
FIG. 35 is a cross-sectional view though the assembled camera housing along the line XII-XII of FIG. 34.
Figure 36:
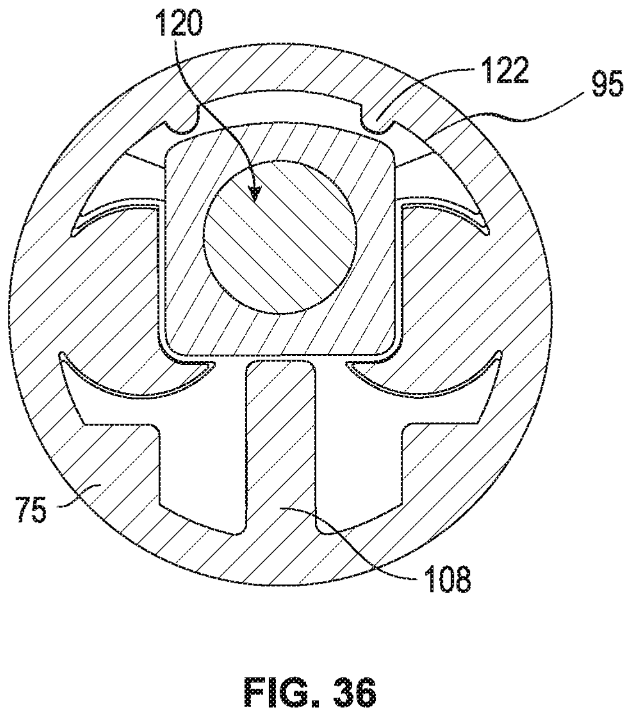
FIG. 36 is a cross-sectional view though the assembled camera housing along the line XIII-XIII of FIG. 34.
Figure 37:
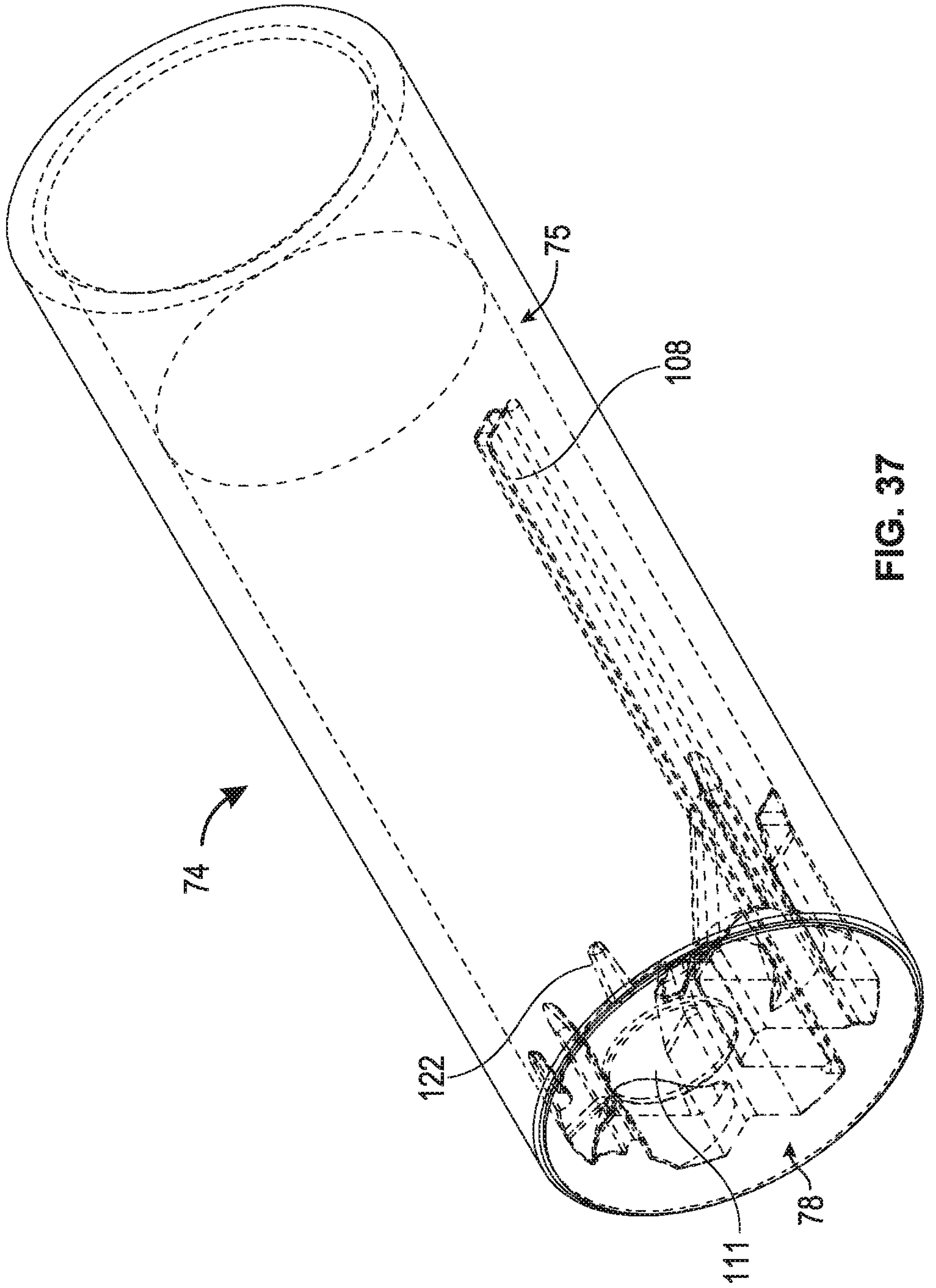
FIG. 37 is a perspective view of the camera housing of FIG. 25 without internal components inserted, but with internal features illustrated by means of broken lines.

FIG. 34 is a side view of the assembled camera housing of FIG. 25, however without the image transmission cable and the tapering proximal part, with indications of sectional views shown in FIGS. 35 and 36.

FIGS. 35 and 36 are cross-sectional views though the assembled camera housing. Shown therein are a number of guide tabs 122 are distributed in the circumferential direction of the inner face 95 of the tubular housing part 75 of the camera housing 70 at the distal end wall 78 of the camera housing 70. The guide tabs 122 are provided on the inner face 95 of the tubular part and on the distal end wall 78, and the guide tabs 122 are arranged to guide the camera module 10 during its insertion into the camera housing 70.

Preferably, the thickness of the distal end wall 78 in the bottom of the recess 111 is less than 0.4 mm, preferably around 0.25 mm. The thickness of the end wall 78 at the illustrated lens structures 66 is more than 1 mm. In a preferred embodiment the wall thickness of the wall of the tubular housing part 75 of camera housing is at least 0.4 mm.

Figure 38:
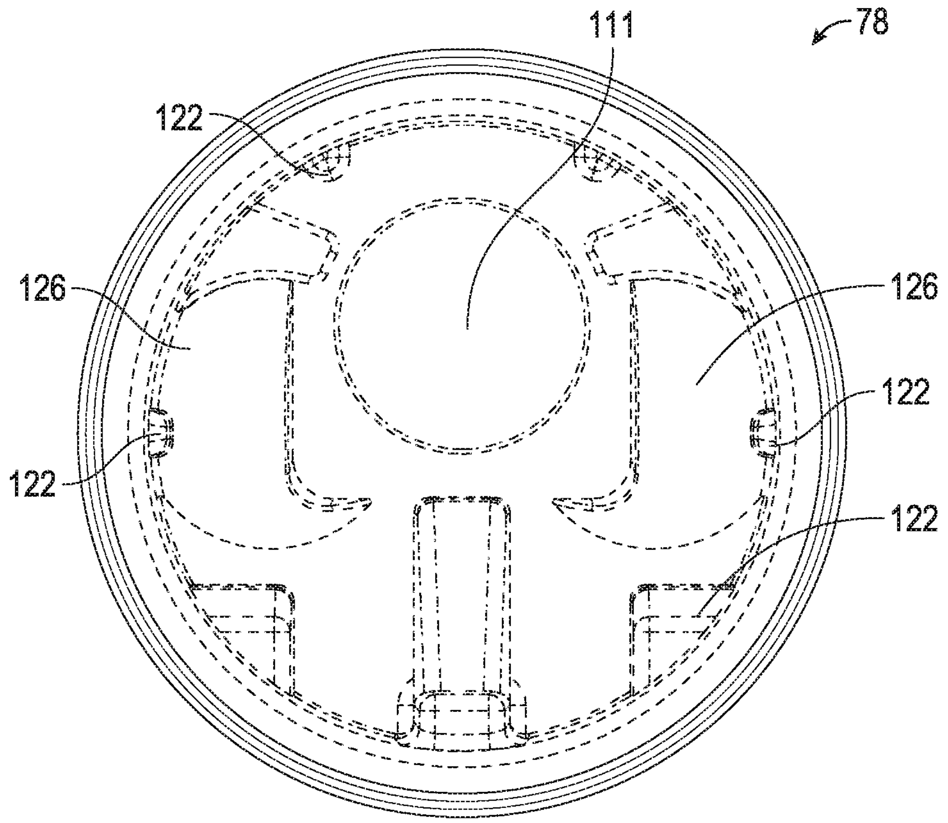
FIG. 38 is an end view of a distal end wall of the camera housing, seen from a distal end thereof, and with internal features illustrated by means of broken lines.
Figure 39:
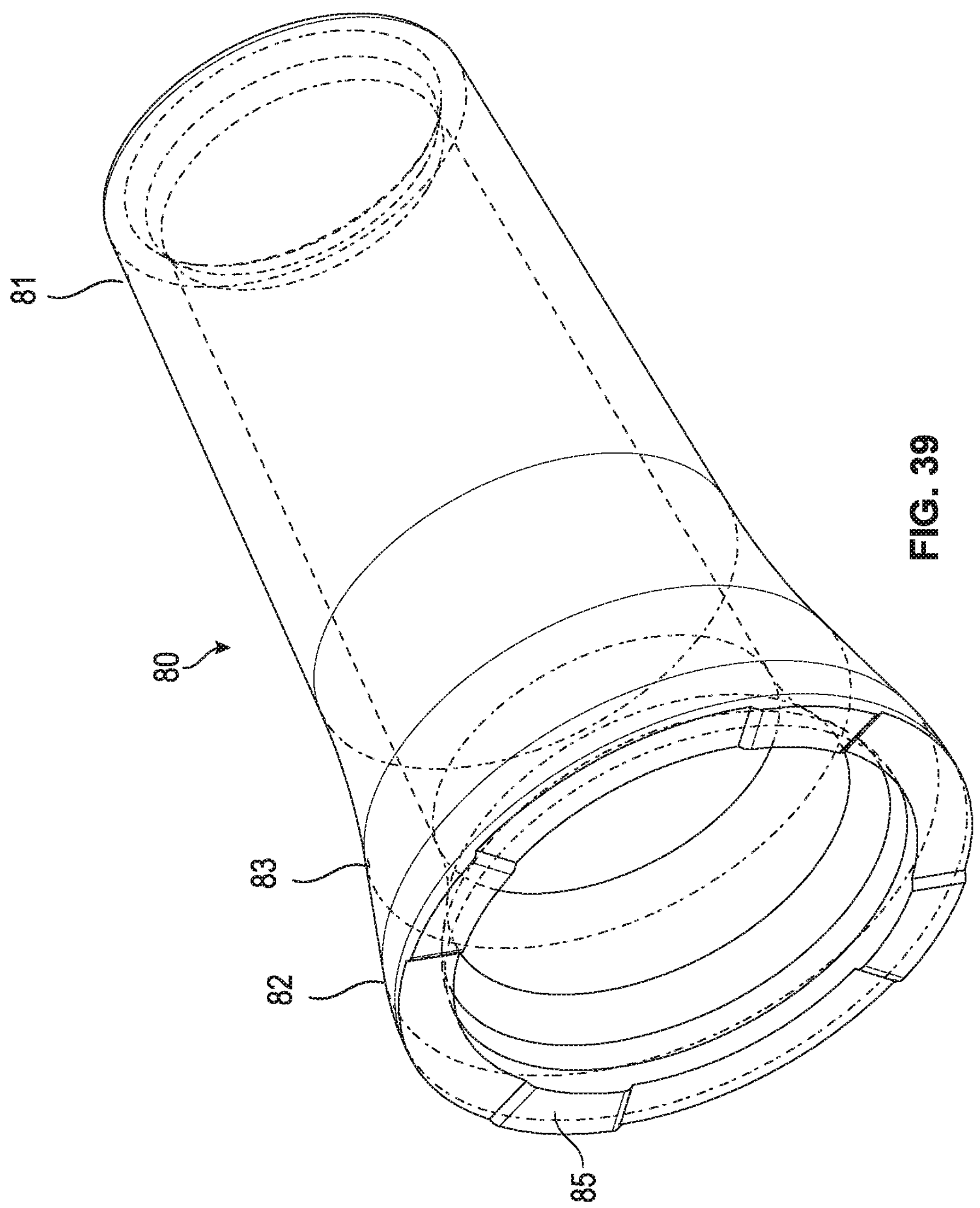
FIG. 39 illustrates a perspective view of a proximal portion of the camera housing illustrated in FIG. 25.

Furthermore, as seen in FIG. 38, the distal end wall 78 of the camera housing comprises two opposed lens structures 126 which in the assembled state of the camera housing are positioned in front of the light sources 88.

Figure 40:
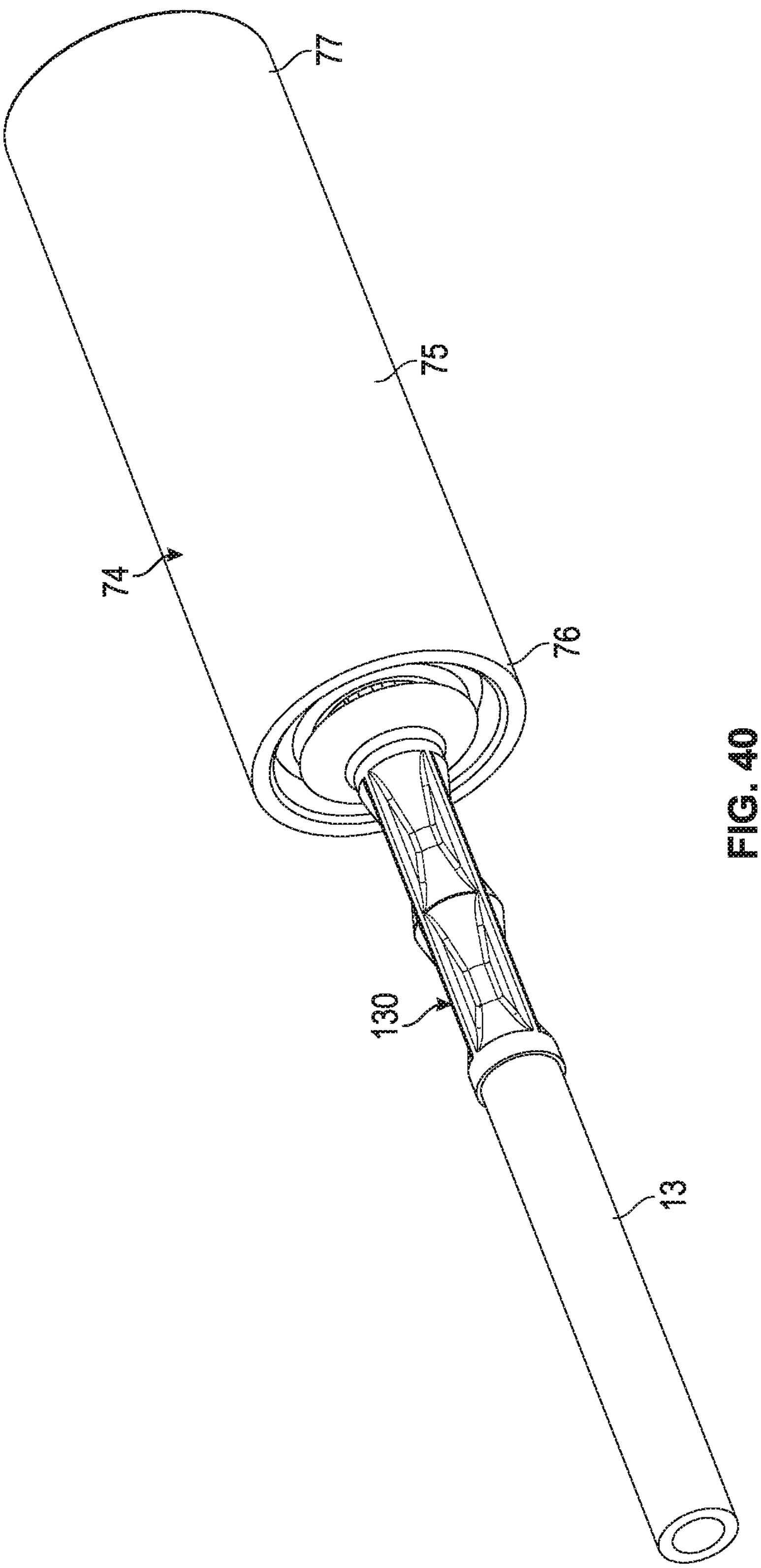
FIG. 40 is a perspective view of the camera housing corresponding to that of FIG. 25, but with the proximal portion thereof removed.
Figure 41:
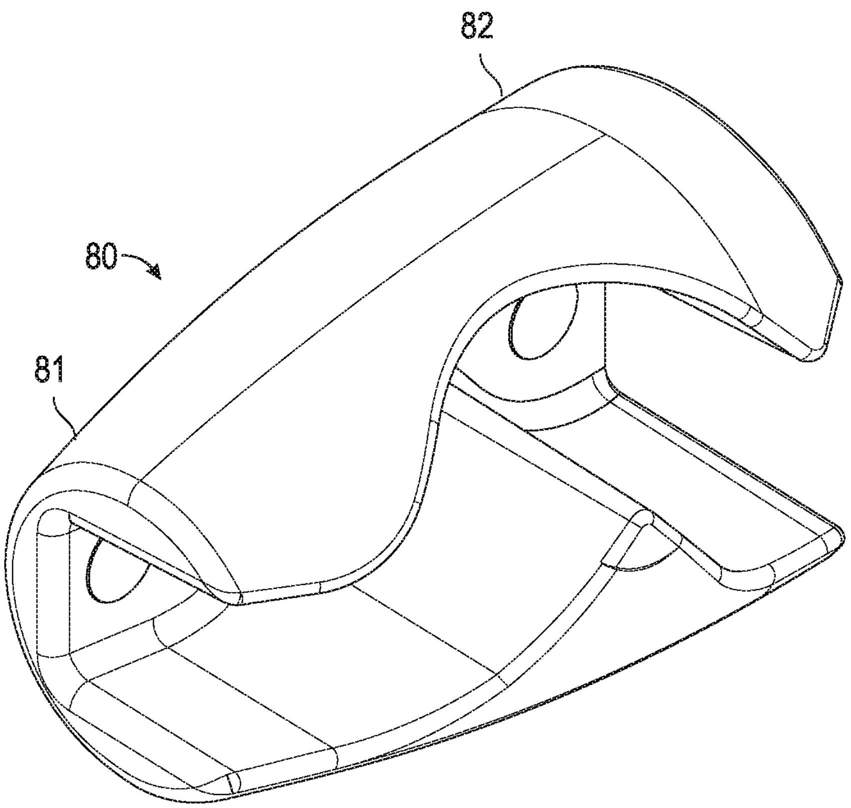
FIG. 41 illustrates a perspective view of an alternative proximal portion of the camera housing.

As illustrated in FIG. 40, the image transmission cable 13 is retained inside of the proximal portion 80 by means of a crimp 130 fixed on the image transmission cable 13 inside the proximal portion 80. Alternatively, a knot is tied on the image transmission cable 13, which is fixed inside the proximal portion 80. FIG. 41 illustrates an alternative embodiment, in which the image transmission cable 13 may be retained inside of the proximal portion 80 by means of a labyrinth in which the image transmission cable 13 may be trapped and/or glued. As shown, the labyrinth comprises a protrusion extending between two curved sections, on one side, and corresponding two protrusions with an intermediate depression, on the opposite side.

Figure 42:
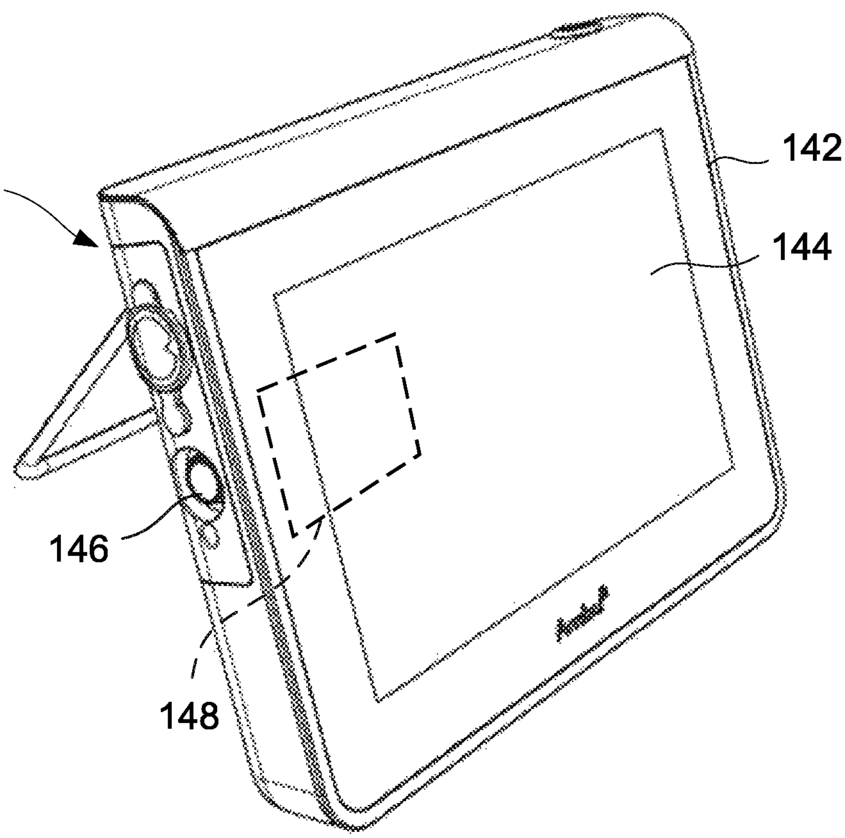
FIG. 42 shows an embodiment of a video processing apparatus.
Figure 43:
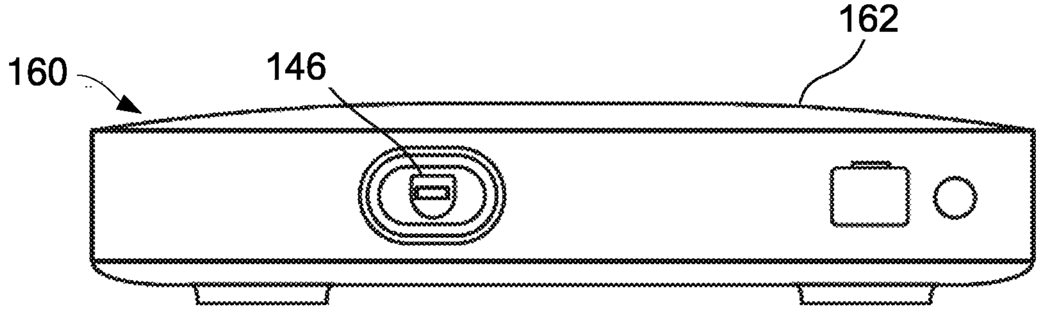
FIG. 43 shows another embodiment of a video processing apparatus.

FIGS. 42 and 43 illustrate examples of the VPA 68, denoted by numerals 140 and 160. The VPA may be referred to as a monitor or image display. In FIG. 42, the VPA 140 includes a housing 142 enclosing and supporting a display screen 144. a video processing circuit (not shown), and a medical device interface 148. The display screen 144 may be a touch-screen. A cable socket 146 receives a cable connector of the image transmission cable 13 to establish a signal communication between the image sensor and the VPA. The VPA allows an operator to view an image captured by the image sensor. The medical device interface 148 is tailored to a specific medical device technology, such as a type or model of image sensor, electronic circuits to encode other endoscope signals, configuration parameters of the image sensor, and the like. The medical device interface 148 is connected to the video processing circuit and can preprocess signals before conveying them to the video processing circuit. For example, the medical device interface 148 may deserialize a video signal or modify the size of the frames. Thus, the medical device interface 148 is technologically matched to a particular medical device, and inclusion of the medical device interface 148 in the VPA 86, 140, 160 matches the medical device 1 to the VPA. As shown in FIG. 42, the VPA 140, 160 may comprise multiple cable sockets 146 and, correspondingly, multiple medical device interfaces 148, which may be coded to indicate which endoscope matches which medical device interface. Coding may be via symbols, colors, or both. Example medical device interfaces and codings are described in commonly owned U.S. Pat. Nos. 11,166,622 and 11,166,624, both issued Nov. 9, 2021 and incorporated herein by reference.

It might not be desirable to provide a video display screen with a touch screen, or it might be desirable to omit a display screen altogether. Omission of the display screen might be beneficial to take advantage of evolving video display technologies which improve resolution and reduce cost. Provision of exchangeable medical device interfaces allows for adoption of evolving image sensor and endoscope technologies, thus use of existing or future-developed external video displays could allow presentation of higher resolution or otherwise improved video. Use of external video displays could also leverage existing capital investments. Accordingly, in FIG. 43 the VPA 160 comprises a housing 162 supporting a video processing circuit (not shown), a medical device interface, and cable socket 146, but excludes a display screen.

In an embodiment according to the third aspect of the invention, an assembly method is provided for mounting the camera module in the camera housing and the camera lumen. According to the method, the camera module 10 is positioned in the support structure 90 with a distal end thereof between the spaced tabs 100 and the image transmission cable 13 passing though the proximal portion 80 of the tip housing 70. Thereafter, the camera module 10 and the support structure 90 are inserted into the tubular housing part 75 with the guide rib 108 riding in the longitudinal groove 99. The distal end wall 78 of the camera housing 70 has a recess 111 and the camera module 10 is moved until at least a portion of a lens barrel 86, or a lens contained therein, of the camera module 10 is inserted in the recess 111. A transparent portion, or window, of the distal end wall 78 may be positioned distally of the camera module 10. Alternatively, the window is omitted, in which case the distal end of the camera module 10, e.g. the barrel, is adhesively sealed to the recess 111.

Once the camera module 10 and the support structure 90 are in position in the tubular housing part 75, the proximal portion 80 of the tip housing 70 is adhesively bonded to the housing element 74 and the secured to the image transmission cable 13. The proximal portion 80 may be adhesively bonded to the outer face 106 of the image transmission cable 13.

The image transmission cable 13 is passed through the camera lumen 4A of the main tube 2 and pulled proximally as the camera housing 70 is positioned in the camera lumen extension 24 of the tip housing 20, 20D. The camera housing 70 may protrude proximally into the camera lumen 4A. Due to tight tolerances, the camera housing 70 may be press-fit into the camera lumen extension 24. A lubricant may be applied to the external surface to facilitate insertion. The cable can be inserted from the proximal end and then electrically connected to the circuit board 89.

The following items are further variations and examples of the embodiments described with reference to FIGS. 1 to 43.

1. A medical device in the form of an airway device including a main tube having at least a first lumen and a dedicated camera lumen, the first lumen having a proximal end and a distal end, the distal end being adapted to be placed inside a body cavity during use of the medical device, the tube having an outer wall enclosing at least the first lumen and the camera lumen, the camera lumen having a proximal end and a distal end, a camera module including at least an image sensor and one or more light sources being arranged at the distal end of the first lumen, and an image transmission cable attached to the camera module extending through at least part of the camera lumen in order to connect to an image display device, wherein a separately manufactured tip housing has a proximal end and a distal end, wherein the proximal end of the tip housing is mounted on the main tube at the distal end of the first lumen, wherein the tip housing forms a tip extension of the first lumen and a tip extension of the camera lumen, wherein the tip extension of the first lumen has an open end, and wherein the camera module is arranged at least partly in the tip extension of the camera lumen.

2. A medical device according to item 1, wherein the main tube has a flush lumen enclosed by the outer wall, wherein the flush lumen has a proximal end and a distal end, wherein the tip housing forms a tip extension of the flush lumen, and wherein the tip extension of the flush lumen communicates with at least one flush outlet directed at a lens end of the camera module.
3. A medical device according to item 2, wherein the camera module is fixed in the tip extension of the camera lumen by means of a camera housing, and wherein the at least one flush outlet forms part of the camera housing.
4. A medical device according to item 2 or 3, wherein the tip extension of the flush lumen is provided with a proximally protruding pipe engaging the flush lumen of the main tube.
5. A medical device according to any one of the preceding items, wherein the main tube is provided with a first inflatable cuff, wherein the main tube has a first cuff lumen enclosed by the outer wall and communicating with the first inflatable cuff, wherein the first cuff lumen has a proximal end and a distal end, and wherein the distal end of the first cuff lumen is closed by means of a sealing plug arranged on the proximal end of the tip housing.
6. A medical device according to any one of the preceding items, wherein the main tube has an anesthetic lumen enclosed by the outer wall, wherein the anesthetic lumen has a proximal end and a distal end, wherein the tip housing forms a tip extension of the anesthetic lumen, and wherein the tip extension of the anesthetic lumen communicates with at least one anesthetic outlet port.
7. A medical device according to item 6, wherein the tip extension of the anesthetic lumen is provided with a proximally protruding pipe distally engaging the anesthetic lumen of the main tube.
8. A medical device according to any one of the preceding items, wherein the main tube has a second lumen having a proximal end and a distal end, wherein the second lumen is enclosed by the outer wall, wherein the tip housing forms a tip extension of the second lumen.
9. A medical device according to item 8, wherein a distal tube is mounted on the distal end of the tip housing, thereby forming a further extension of the second lumen.
10. A medical device according to item 9, wherein the distal tube is provided with a second inflatable cuff, wherein the main tube has a second cuff lumen enclosed by the outer wall, wherein the tip housing forms a tip extension of the second cuff lumen, wherein the distal tube forms a distal second cuff lumen enclosed by an outer wall of the distal tube, and wherein the distal second cuff lumen of the distal tube connects the tip extension of the second cuff lumen and the second inflatable cuff.
11. A medical device according to item 10, wherein the tip extension of the second cuff lumen is provided with a first protruding pipe arranged at the proximal end of the tip housing and engaging the second cuff lumen of the main tube, and wherein the tip extension of the second cuff lumen is provided with a second protruding pipe arranged at the distal end of the tip housing and engaging proximal end of the distal second cuff lumen of the distal tube.
12. A medical device according to any one of the preceding items, wherein the camera module is fixed in the tip extension of the camera lumen by means of a camera housing extending in a longitudinal direction and having a proximal end and a distal end, wherein the camera housing includes a tubular housing part at least partly surrounding the camera module and a distal end wall, wherein the tubular housing part and the distal end wall are integrally molded and form one single housing element, and wherein the tubular housing part fits tightly into the tip extension of the camera lumen of the tube.
13. A medical device according to any one of the preceding items, wherein the tip housing is made by molding, such as injection molding, or 3D printing.
14. A medical device according to any one of the preceding items, wherein the proximal end of the tip housing has a proximal junction interface fitting an abutment surface of the main tube, wherein said abutment surface includes at least an end face of the outer wall of the main tube, wherein the proximal junction interface forms a groove with said abutment surface of the main tube, and wherein said groove contains hardened glue.
15. A medical device according to any one of the preceding items, wherein the tip extension of the at least first lumen, at the proximal end of the tip housing, is provided with a proximally protruding pipe engaging the distal end of the at least first lumen of the main tube.
16. A medical device according to any one of the items 9 to 11, wherein the distal end of the tip housing has a distal junction interface fitting an abutment surface of the distal tube, wherein said abutment surface includes at least an end face of the outer wall of the distal tube, wherein the distal junction interface forms a groove with said abutment surface of the distal tube, and wherein said groove contains hardened glue.
17. A medical device according to any one of the items 9 to 11 or 16, wherein the tip extension of the second lumen, at the distal end of the tip housing, is provided with a protruding pipe engaging the proximal end of the further extension of the second lumen formed in the distal tube.
18. A medical device according to any one of the preceding items, wherein the medical device is a catheter.
19. A medical device according to any one of the preceding items, wherein the camera module is fixed in the tip extension of the camera lumen.
20. A medical device according to any one of the preceding items, wherein the medical device is an endotracheal tube.
21. A medical device including a tube having at least a first lumen and a dedicated camera lumen, the first lumen having a proximal end and an open distal end, the distal end being adapted to be placed inside a body cavity during use of the medical device, the tube having an outer wall enclosing at least the first lumen and the camera lumen, the camera lumen having a proximal end and a distal end, a camera module including at least an image sensor and one or more light sources being arranged in the camera lumen at the distal end thereof so that the camera module is positioned adjacent the distal end of the first lumen, and an image transmission cable attached to the camera module extending through at least part of the camera lumen in order to connect to an image display device, wherein the camera module is fixed in the camera lumen by means of a camera housing extending in a longitudinal direction and having a proximal end and a distal end, wherein the camera housing includes a tubular housing part at least partly surrounding the camera module and a distal end wall, wherein the tubular housing part and the distal end wall are integrally molded and form one single housing element, and wherein the tubular housing part fits tightly into the camera lumen of the tube.

22. A medical device according to item 21, wherein the camera housing includes a support structure for the camera module, wherein the support structure has a proximal end and a distal end, wherein the proximal end of the support structure has a tubular end part arranged inside the tubular housing part of the camera housing, wherein the image transmission cable extends through the tubular end part of the support structure, and wherein the distal end of the support structure is engaged with the camera module.

23. A medical device according to item 22, wherein the tubular end part of the support structure has an outer face being glued to an inner face of the tubular part of the camera housing.

24. A medical device according to item 23, wherein the outer face of the tubular end part of the support structure and/or the inner face of the tubular housing part of the camera housing are/is tapered or conical so that a gap for glue is formed, a cross-section of said gap generally decreasing in the direction from the proximal end to the distal end of the support structure.

25. A medical device according to item 23 or 24, wherein the outer face of the tubular end part of the support structure and/or the inner face of the tubular housing part of the camera housing are/is provided with a number of ribs distributed in the circumferential direction of the outer face and/or the inner face.

26. A medical device according to item 25, wherein the ribs only extend at a distal end of the tubular end part of the support structure.

27. A medical device according to item 25 or 26, wherein said ribs include two pivot forming ribs arranged diametrically opposite of the tubular end part of the support structure and/or of the tubular part of the camera housing and together providing a relatively tight fit with the corresponding outer face or inner face, wherein said ribs further include at least two distance ribs distributed peripherally about the tubular end part of the support structure and/or of the tubular part of the camera housing and together providing a relatively loose fit with the corresponding outer face or inner face, and wherein, preferably, the two pivot forming ribs protrude longer in the radial direction of the tubular end part than the distance ribs protrude.

28. A medical device according to item 27, wherein the distal end of the support structure is provided with two spaced tabs arranged generally symmetrically about a plane extending through said two pivot forming ribs, and wherein the two spaced tabs are adapted to abut the camera module.

29. A medical device according to item 28, wherein the support structure includes an elongated part having generally semi-circular cross-section, and wherein the elongated part connects the proximal end of the support structure with the two spaced tabs.

30. A medical device according to item 29, wherein the elongated part is provided with a peripherally extending recess facing the inner face of the tubular part of the camera housing next to the tubular end part of the support structure.

31. A medical device according to any one of the items 22 to 30, wherein the tubular end part of the support structure has an inner face being glued to an outer face of the image transmission cable.

32. A medical device according to item 31, wherein the inner face of the tubular end part of the support structure is tapered or conical so that a gap for glue is formed, a cross-section of said gap generally decreasing in the direction from the proximal end to the distal end of the support structure.

33. A medical device according to item 31 or 32, wherein the inner face of the tubular end part of the support structure is provided with a number of ribs distributed in the circumferential direction of the inner face.

34. A medical device according to any one of the items 2 to 13, wherein the support structure or the inner face of the tubular part of the camera housing has a guide rib extending in the longitudinal direction of the camera housing, wherein the corresponding one of the support structure and the inner face of the tubular part of the camera housing has a groove extending in the longitudinal direction of the camera housing, and wherein the guide rib is adapted to slide in the groove.

35. A medical device according to item 34, wherein the camera module is arranged extending from the distal end of the support structure, wherein the inner face of the tubular part of the camera housing is provided with the guide rib, and wherein the guide rib is wedge-formed at the distal end of the camera housing in order to guide the camera module.

36. A medical device according to items 29 and 34, wherein the inner face of the tubular part of the camera housing is provided with the guide rib, wherein the elongated part is provided with the groove extending in the longitudinal direction of the camera housing, wherein the groove is arranged symmetrically about the plane extending through said two pivot forming ribs, and wherein, preferably, the guide rib has a loose fit in the groove.

37. A medical device according to any one of the preceding items, wherein a number of guide tabs are distributed in the circumferential direction of the inner face of the tubular part of the camera housing at the distal end wall of the camera housing, wherein the guide tabs are provided on the inner face of the tubular part and/or on the distal end wall, and wherein the guide tabs are arranged to guide the camera module during its insertion into the camera housing.

38. A medical device according to any one of the preceding items, wherein the distal end wall of the camera housing has a recess in which at least a portion of a lens barrel of the camera module is inserted.

39. A medical device according to any one of the preceding items, wherein the camera housing includes a proximal portion arranged at a proximal end of the tubular housing part, wherein the proximal portion has a proximal end and a distal end and a tapering part arranged between the proximal end and the distal end, and wherein an outer diameter of the proximal end is smaller than an outer diameter of the distal end.

40. A medical device according to item 39, wherein the tubular housing part has an outer cylindrical surface, and wherein the outer diameter of the distal end of the proximal portion corresponds to an outer diameter of the outer cylindrical surface.

41. A medical device according to item 39 or 40, wherein the proximal portion is a separate element attached to the tubular housing part.

42. A medical device according to item 41, wherein the distal end of the proximal portion has a number of protrusions distributed in its circumferential direction and abutting the proximal end of the tubular part, and wherein the tubular part and the proximal portion are connected by means of glue.
43. A medical device according to item 41, wherein the proximal end of the tubular part has a number of protrusions distributed in its circumferential direction and abutting the distal end of the proximal portion, and wherein the tubular part and the proximal portion are connected by means of glue.
44. A medical device according to any one of the items 39 to 43, wherein the image transmission cable is retained inside of the proximal portion.
45. A medical device according to item 44, wherein a crimp is fixed on the image transmission cable inside the proximal portion.
46. A medical device according to any one of the preceding items, wherein the first lumen and the camera lumen, and an optional second lumen, are coextruded to form the tube.
47. A medical device according to any one of the preceding items, wherein the outer wall of the tube is generally ring-formed and surrounds at least the first lumen, and wherein the camera lumen is formed in the material of the outer wall between an inner surface and an outer surface of the outer wall.
48. A medical device according to item 47, wherein the outer wall of the tube further surrounds at least part of a second lumen having a proximal end and an open distal end, and wherein the first lumen and the second lumen are separated by means of a partition wall.
49. A medical device according to item 48, wherein the camera lumen is formed in the material of the outer wall at a position where the partition wall is connected to the outer wall.
50. A medical device according to any one of the preceding items, wherein the outer wall of the tube surrounds the first lumen and a second lumen, wherein the first lumen and the second lumen are separated by means of a partition wall, and wherein the camera lumen is formed at the outer wall at a position where the partition wall is connected to the outer wall.
51. A medical device according to item 50, wherein the first lumen and the second lumen are symmetrically arranged about the partition wall and in relation to the camera lumen.
52. A medical device according to item 50 or 51, wherein the tubular housing part of the camera housing has a cylindrical outer surface having a central axis of symmetry, and wherein a lens barrel of the camera module is eccentrically arranged in relation to the cylindrical outer surface of the tubular housing part.
53. A medical device according to item 52, wherein a central axis of the lens barrel of the camera module is displaced in relation to the central axis of symmetry of the cylindrical outer surface of the tubular housing part of the camera housing in a direction so that the lens barrel is closer to the first lumen than to the second lumen.
54. A medical device according to any one of the preceding items, wherein the medical device is a catheter.
55. A medical device according to any one of the preceding items, wherein the medical device is an airway device.
56. A medical device according to any one of the preceding items, wherein the medical device is a double lumen endotracheal tube having a first lumen in the form of a tracheal lumen and a second lumen in the form of a bronchial lumen, wherein the first lumen and the second lumen extend together from the proximal end of the first lumen to the distal end of the first lumen, and wherein the second lumen extends further from the distal end of the first lumen to a distal end of the second lumen.
57. A medical device according to item 56, wherein the double lumen endotracheal tube has a first inflatable cuff arranged proximally the open distal end of the first lumen and a second inflatable cuff arranged proximally the open distal end of the second lumen.
58. A medical device according to any one of the items 21 to 55, wherein the medical device is a single lumen endotracheal tube.
59. A medical device according to item 58, wherein the single lumen endotracheal tube has a first inflatable cuff arranged proximally the open distal end of the first lumen.
60. A system including a medical device according to any one of the preceding items, wherein the system includes a monitor or image display device connected to the image transmission cable directly or by means of a wireless connection.
61. A medical device including: a tube having an outer wall, a first lumen and a camera lumen, the first lumen having a proximal end and a distal end, the camera lumen having a proximal end and a distal end, and the outer wall enclosing the first lumen and the camera lumen; a camera housing including a proximal portion and a singular housing element affixed to the proximal portion, the singular housing element comprising a tubular housing part integrally molded in one-piece with a distal end wall, the tubular housing part sized to fit tightly into the camera lumen of the tube, the tubular housing part having an inner face, a proximal end and a distal end; a support structure positioned in the camera housing and comprising a proximal end, a distal end, and a tubular end part at the proximal end of the support structure, the tubular end part having an outer face forming a gap with the inner face of the tubular housing part; an adhesive in the gap affixing the support structure to the singular housing element; and a camera module supported by the support structure inside the camera housing, the camera module including an image sensor and a light source positioned at the distal end of the camera lumen adjacent the distal end of the first lumen.
62. The medical device of item 61, wherein the outer face of the tubular end part of the support structure and/or the inner face of the tubular housing part of the camera housing are/is tapered or conical so that the gap has a cross-section that decreases in the direction from the proximal end to the distal end of the support structure.
63. The medical device of item 61, wherein the outer face of the tubular end part of the support structure and/or the inner face of the tubular housing part of the camera housing are/is provided with ribs.
64. The medical device of item 63, wherein the ribs only extend at a distal end of the tubular end part of the support structure.
65. The medical device of item 63, wherein the ribs include two pivot forming ribs arranged diametrically opposite of the tubular end part of the support structure and/or of the tubular part of the camera housing and together providing a relatively tight fit with the corresponding outer face or inner face, wherein the ribs further include two distance ribs distributed peripherally about the tubular end part of the support structure and/or of the tubular part of the camera housing and together providing a relatively loose fit with the corresponding outer face or inner face, and wherein the two pivot forming ribs extending further radially than the distance ribs.

66. The medical device of item 63, wherein the ribs include two pivot forming ribs arranged diametrically opposite of the tubular end part of the support structure and/or of the tubular part of the camera housing and together providing a relatively tight fit with the corresponding outer face or inner face, wherein the ribs further include two distance ribs distributed peripherally about the tubular end part of the support structure and/or of the tubular part of the camera housing and together providing a relatively loose fit with the corresponding outer face or inner face.

67. The medical device of item 66, wherein the distal end of the support structure is provided with two spaced tabs arranged generally symmetrically about a plane extending through the two pivot forming ribs, and wherein the two spaced tabs are adapted to abut the camera module.

68. The medical device of item 67, wherein the support structure includes an elongated part having generally semi-circular cross-section, and wherein the elongated part connects the proximal end of the support structure with the two spaced tabs.

69. The medical device of item 68, wherein the elongated part is provided with a peripherally extending recess facing the inner face of the tubular part of the camera housing next to the tubular end part of the support structure.

70. The medical device of item 68, wherein the inner face of the tubular part of the camera housing is provided with a guide rib, wherein the elongated part is provided with the groove extending in the longitudinal direction of the camera housing, wherein the groove is arranged symmetrically about the plane extending through the two pivot forming ribs.

71. The medical device of item 61, further comprising an image transmission cable having an outer face, wherein the inner face of the tubular end part of the support structure is adhesively bonded to the outer face of the image transmission cable.

72. The medical device of item 61, wherein the support structure or the inner face of the tubular part of the camera housing has a guide rib extending in a longitudinal direction of the camera housing, wherein the corresponding support structure or inner face of the tubular part of the camera housing has a groove extending in the longitudinal direction of the camera housing, and wherein the guide rib is adapted to slide in the groove.

73. The medical device of item 72, wherein the inner face of the tubular part of the camera housing is provided with the guide rib, and wherein the guide rib is wedge-formed at the distal end of the camera housing to guide the camera module during assembly.

74. The medical device of item 61, further comprising guide tabs provided on the inner face of the tubular part and/or on the distal end wall, and wherein the guide tabs are arranged to guide the camera module during its insertion into the camera housing.

75. The medical device of item 61, wherein the proximal portion of the camera housing comprises a proximal end, a distal end and a tapering part between the proximal end and the distal end, and wherein an outer diameter of the proximal end is smaller than an outer diameter of the distal end.

76. The medical device of item 61, wherein the outer wall comprises an inner surface and an outer surface, wherein the camera lumen is formed in the outer wall between the inner surface and the outer surface of the outer wall.

77. A visualization system comprising a medical device according to item 61 and a monitor or image display device, the medical device further comprising an image transmission cable, the monitor or image display device connected to the image transmission cable directly or via a wireless connection.

78. The visualization system of item 77, wherein the outer wall further comprises an inner surface and an outer surface, the camera lumen formed in the outer wall between the inner surface and the outer surface.

79. The visualization system of item 78, wherein the tube comprises a second lumen and a partition wall separating the first lumen and the second lumen, and wherein the camera lumen is formed an intersection of the outer wall and the partition wall.

80. The visualization system of item 79, wherein the camera assembly includes a lens barrel having a central axis, and wherein the central axis is closer to the first lumen than to the second lumen.

81. A medical device including: a tube having an outer wall, a first lumen and a camera lumen, the first lumen having a proximal end and a distal end, the camera lumen having a proximal end and a distal end, and the outer wall enclosing the first lumen and the camera lumen; a camera housing including a proximal portion and a singular housing element affixed to the proximal portion, the singular housing element comprising a tubular housing part integrally molded in one-piece with a distal end wall, the tubular housing part sized to fit tightly into the camera lumen of the tube, the tubular housing part having an inner face, a proximal end and a distal end; a support structure positioned in the camera housing and comprising a proximal end, a distal end, and a tubular end part at the proximal end of the support structure, the tubular end part having an outer face forming a gap with the inner face of the tubular housing part; an adhesive in the gap affixing the support structure to the singular housing element; and a camera module supported by the support structure inside the camera housing, the camera module including an image sensor and a light source positioned at the distal end of the camera lumen adjacent the distal end of the first lumen, wherein the outer wall further comprises an inner surface and an outer surface, the camera lumen formed in the outer wall between the inner surface and the outer surface, wherein the outer face of the tubular end part of the support structure and/or the inner face of the tubular housing part of the camera housing are/is tapered or conical so that the gap has a cross-section that decreases in the direction from the proximal end to the distal end of the support structure, and wherein the outer face of the tubular end part of the support structure and/or the inner face of the tubular housing part of the camera housing are/is provided with ribs including two pivot forming ribs and two distance ribs, the two pivot forming ribs arranged diametrically opposite of the tubular end part of the support structure and/or of the tubular part of the camera housing, the two distance ribs distributed peripherally about the tubular end part of the support structure and/or of the tubular part of the camera housing, the two pivot forming ribs extending radially further than the distance ribs.

82. A medical device including: a main tube having an outer wall, a distal end, a first lumen, a flush lumen and a camera lumen, the first lumen having a proximal end and a distal end, the camera lumen having a proximal end and a distal end, the outer wall enclosing the first lumen, the camera lumen extending within the outer wall, and the flush lumen extending within the outer wall; a tip housing separately manufactured from the main tube, the tip housing comprising a proximal end, a distal end, a tubular housing part extending from the proximal end to the distal end, a first lumen extension having an open end, a camera lumen extension, a flush lumen extension and a flush outlet configured to discharge fluid received from the flush lumen through the flush lumen extension, the first lumen extension extending distally from the first lumen, the camera lumen extension extending distally from the camera lumen, the flush lumen extension axially aligned with and extending distally from the flush lumen, the tubular housing part enclosing the first lumen extension and the camera lumen extension, the flush lumen extension extending between an outer surface and an inner surface of the tubular housing part with the flush outlet extending between the flush lumen extension and the inner surface, and the proximal end of the tip housing mounted at the distal end of the main tube; a camera module arranged at least partly in the camera lumen extension of the tip housing, the flush outlet located distally of the camera module; and a camera housing affixing the camera module in the camera lumen extension.

83. The medical device of item 82, wherein the tubular housing part comprises a proximal end and a distal end, wherein the tip housing comprises a flush pipe aligned with the flush lumen extension and extending proximally of the proximal end of the tubular housing part, the flush pipe configured to engage the flush lumen of the main tube.

84. The medical device of item 82, wherein the main tube has a second lumen having a proximal end and a distal end, wherein the second lumen is enclosed by the outer wall, and wherein the tip housing comprises a second lumen extension axially aligned and extending distally from the second lumen.

85. The medical device of item 84, further comprising a distal tube mounted onto the distal end of the tip housing, wherein the distal tube and the tip housing comprise different materials.

86. A medical device including: a main tube having an outer wall, a distal end, a first lumen and a camera lumen, the first lumen having a proximal end and a distal end, the camera lumen having a proximal end and a distal end, the outer wall enclosing the first lumen, and the camera lumen extending within the outer wall; a tip housing separately manufactured from the main tube, the tip housing comprising a proximal end, a distal end, a tubular housing part extending from the proximal end to the distal end, a first lumen extension having an open end, and a camera lumen extension, the first lumen extension extending distally from the first lumen, the camera lumen extension extending distally from the camera lumen, the tubular housing part enclosing the first lumen extension and the camera lumen extension, and the proximal end of the tip housing mounted at the distal end of the main tube; and a camera module arranged at least partly in the camera lumen extension of the tip housing.

87. The medical device of item 86, further comprising a camera housing affixing the camera module in the camera lumen extension.

88. The medical device of item 87, wherein the camera housing extends in a longitudinal direction and comprises a proximal end and a distal end, wherein the camera housing includes a tubular housing part at least partly surrounding the camera module and a distal end wall, wherein the tubular housing part and the distal end wall are integrally molded and form one single housing element, and wherein the tubular housing part fits tightly into the camera lumen extension.

89. The medical device of item 86, wherein the main tube comprises a flush lumen enclosed by the outer wall, wherein the tip housing comprises a flush lumen extension aligned with and extending distally from the flush lumen, the tubular housing part enclosing the flush lumen extension and comprising a flush outlet configured to discharge fluid received from the flush lumen through the flush lumen extension.

90. The medical device of item 89, wherein the flush lumen is intermediate the proximal end and the distal end of the tip housing and configured to discharge flushing fluid distally of a distal end of the camera housing.

91. 4. The medical device of item 89, wherein the tubular housing part comprises a proximal end and a distal end, wherein the tip housing comprises a flush pipe aligned with the flush lumen extension and extending proximally of the proximal end of the tubular housing part, the flush pipe configured to engage the flush lumen of the main tube.

96. The medical device of item 86, wherein the main tube comprises an anesthetic lumen enclosed by the outer wall, wherein the tip housing comprises an anesthetic lumen extension aligned with and extending distally from the anesthetic lumen, wherein the tip housing comprises an anesthetic outlet port, and wherein the anesthetic lumen extension is in fluid communication with the anesthetic outlet port to discharge an anesthetic received from the anesthetic lumen through the anesthetic lumen extension.

97. The medical device of item 96, wherein the tip housing comprises an anesthetic pipe aligned with the anesthetic lumen extension and extending proximally of the proximal end of the tubular housing part, the anesthetic pipe configured to engage the anesthetic lumen of the main tube.

98. The medical device of item 86, wherein the main tube comprises a second lumen having a proximal end and a distal end, wherein the second lumen is enclosed by the outer wall, and wherein the tip housing comprises a second lumen extension axially aligned and extending distally from the second lumen.

99. The medical device of item 98, further comprising a distal tube mounted onto the distal end of the tip housing.

100. The medical device of item 99, wherein the distal tube is provided with a second inflatable cuff, wherein the main tube has a second cuff lumen enclosed by the outer wall, wherein the tip housing forms a tip extension of the second cuff lumen, wherein the distal tube forms a distal second cuff lumen enclosed by an outer wall of the distal tube, and wherein the distal second cuff lumen of the distal tube connects the tip extension of the second cuff lumen and the second inflatable cuff.

101. The medical device of item 86, wherein the tip extension of the second cuff lumen is provided with a first protruding pipe arranged at the proximal end of the tip housing and engaging the second cuff lumen of the main tube, and wherein the tip extension of the second cuff lumen is provided with a second protruding pipe arranged at the distal end of the tip housing and engaging proximal end of the distal second cuff lumen of the distal tube.

102. The medical device of item 101, wherein the distal end of the tip housing has a distal junction interface fitting an abutment surface of the distal tube, wherein said abutment surface includes at least an end face of the outer wall of the distal tube, wherein the distal junction interface forms a groove with said abutment surface of the distal tube, and wherein said groove contains hardened glue.

103. The medical device of item 102, wherein the second lumen extension, at the distal end of the tip housing, is provided with a protruding pipe engaging the proximal end of the further extension of the second lumen formed in the distal tube.

104. The medical device of item 86, wherein the proximal end of the tip housing has a proximal junction interface fitting an abutment surface of the main tube, wherein said abutment surface includes at least an end face of the outer wall of the main tube, wherein the proximal junction interface forms a groove with said abutment surface of the main tube, and wherein said groove contains hardened glue.

105. The medical device of item 86, wherein the first lumen extension, at the proximal end of the tip housing, is provided with a proximally protruding pipe engaging the distal end of the first lumen.

106. A system including a medical device according to any one of items 81 to 105 and a monitor or image display device or video processing apparatus communicatively connectable to the medical device.

We claim:

1. A medical device including:

a main tube having an outer wall, a distal end, a first lumen, a second lumen, a second cuff lumen, and a camera lumen, the first lumen having a proximal end and a distal end, the camera lumen having a proximal end and a distal end, the outer wall enclosing the first lumen and the second lumen, the second cuff lumen and the camera lumen extending within the outer wall;

a tip housing separately manufactured from the main tube, the tip housing comprising:

a proximal end mounted at the distal end of the main tube, a distal end, a first lumen extension having an open end and extending distally from the first lumen, a second lumen extension extending distally from the second lumen, a tip extension of the second cuff lumen, a camera lumen extension extending distally from the camera lumen, and a tubular housing part extending from the proximal end to the distal end of the tip housing, the tubular housing part enclosing the first lumen extension, the second lumen extension, the tip extension of the second cuff lumen, and the camera lumen extension;

a first inflatable cuff on the main tube;

a second inflatable cuff;

a distal tube mounted onto the distal end of the tip housing and comprising an outer wall, the distal tube forming a distal second cuff lumen extending within the outer wall of the distal tube, the distal second cuff lumen of the distal tube connecting the tip extension of the second cuff lumen and the second inflatable cuff, and the distal tube and the tip housing comprising different materials, the second inflatable cuff being affixed on the distal tube;

a camera module; and a camera housing positioned in the camera lumen extension, the camera housing comprising:

a tubular camera housing part having an inner face; and a support structure including a tubular end part having an outer face adhesively bonded to the inner face of the tubular camera housing part to secure the camera module to the camera housing.

2. The medical device of claim 1, wherein the tubular end part comprises a plurality of ribs extending from the outer face.

3. The medical device of claim 2, wherein the plurality of ribs include ribs lying on a first plane and ribs lying on a second plane orthogonal to the first plane, wherein the ribs lying on the first plane extend radially outwardly more than the ribs lying on the second plane.

4. The medical device of claim 1, wherein the main tube comprises a flush lumen and the tip housing comprises a flush lumen extension and a flush outlet.

5. The medical device of claim 4, wherein the tubular housing part of the tip housing comprises a proximal end and a distal end, wherein the tip housing comprises a flush pipe aligned with the flush lumen extension and extending proximally of the proximal end of the tubular housing part, the flush pipe configured to engage the flush lumen of the main tube.

6. The medical device of claim 1, wherein the camera housing extends in a longitudinal direction and comprises a distal end wall, wherein the tubular housing part and the distal end wall are integrally moulded and form one single housing element, and wherein the tubular housing part fits tightly into the camera lumen extension.

7. The medical device of claim 6, wherein the main tube comprises a flush lumen and the tip housing comprises a flush lumen extension and a flush outlet, wherein the tubular housing part comprises a proximal end and a distal end, wherein the tip housing comprises a flush pipe aligned with the flush lumen extension and extending proximally of the proximal end of the tubular housing part, the flush pipe configured to engage the flush lumen of the main tube.

8. The medical device of claim 6, wherein the main tube comprises an anesthetic lumen enclosed by the outer wall, wherein the tip housing comprises an anesthetic lumen extension aligned with and extending distally from the anesthetic lumen, wherein the tip housing comprises an anesthetic outlet port, and wherein the anesthetic lumen extension is in fluid communication with the anesthetic outlet port to discharge an anesthetic received from the anesthetic lumen through the anesthetic lumen extension.

9. The medical device of claim 8, wherein the tip housing comprises an anesthetic pipe aligned with the anesthetic lumen extension and extending proximally of the proximal end of the tubular housing part, the anesthetic pipe configured to engage the anesthetic lumen of the main tube.

10. The medical device of claim 1, wherein the tip housing further comprises a first protruding pipe arranged at the proximal end of the tip housing and engaging the second cuff lumen of the main tube and a second protruding pipe arranged at the distal end of the tip housing and engaging a proximal end of the distal second cuff lumen of the distal tube.

11. The medical device of claim 1, wherein the distal end of the tip housing has a distal junction interface fitting an abutment surface of the distal tube, wherein said abutment surface includes at least an end face of the outer wall of the distal tube, wherein the distal junction interface forms a groove with said abutment surface of the distal tube, and wherein said groove contains hardened glue.

12. The medical device of claim 10, wherein the second lumen extension of the tubular housing part, at the distal end of the tip housing, is provided with a protruding pipe engaging a proximal end of a second extension of the second lumen formed in the distal tube.

13. The medical device of claim 1, wherein the proximal end of the tip housing has a proximal junction interface fitting an abutment surface of the main tube, wherein said abutment surface includes at least an end face of the outer wall of the main tube, wherein the proximal junction interface forms a groove with said abutment surface of the main tube, and wherein said groove contains hardened glue.

14. The medical device of claim 1, wherein the tip housing further comprises a proximally protruding pipe engaging the distal end of the first lumen and the first lumen extension.

15. A system comprising:
- the medical device of claim 1; and
- a video processing apparatus communicatively connectable to the medical device, the medical device interface tailored technologically to interface with the video processing apparatus.

16. The medical device of claim 1, wherein the proximal end of the tip housing comprises a protruding pipe and a proximal surface facing an abutment surface of the main tube, the protruding pipe extending proximally from the proximal surface of the tip housing and being received in the first lumen or the second lumen of the main tube.

17. The medical device of claim 1, wherein the camera housing further comprises a proximal portion affixed to the tubular housing part, the proximal portion comprising a proximal end, a distal end and a tapering part between the proximal end and the distal end, and wherein an outer diameter of the proximal end is smaller than an outer diameter of the distal end.

18. The medical device of claim 17, further comprising an image transmission cable, wherein the proximal portion of the camera housing comprises a strain relief comprising a protrusion extending between two curved sections, on one side, and an opposite side opposite the one side, corresponding two protrusions with an intermediate depression, the image transmission cable secured between the one side and the opposite side.

19. A medical device including:
- a main tube having an outer wall, a distal end, a first lumen, a second lumen, a second cuff lumen, and a camera lumen, the first lumen having a proximal end and a distal end, the camera lumen having a proximal end and a distal end, the outer wall enclosing the first lumen and the second lumen, and the second cuff lumen and the camera lumen extending within the outer wall;
- a first inflatable cuff on the main tube;
- a tip housing separately manufactured from the main tube, the tip housing comprising:
  - a proximal end mounted at the distal end of the main tube,
  - a distal end,
  - a tubular housing part including an outer surface extending from the proximal end to the distal end of the tip housing,
  - a first lumen extension including an open end and extending distally from the first lumen,
  - a second lumen extension including an open end and extending distally from the second lumen,
  - a second cuff lumen extension extending distally from the second cuff lumen,
  - a camera lumen extension extending distally from the camera lumen, and
  - the tubular housing part enclosing the first lumen extension, the second lumen extension, the second cuff lumen extension, and the camera lumen extension;
- a second inflatable cuff;
- a distal tube mounted onto the distal end of the tip housing and comprising an outer wall enclosing a distal second lumen extension, the distal second lumen extension extending distally from the second lumen extension, the distal tube forming a distal second cuff lumen extension fluidly coupling the second cuff lumen extension and the second inflatable cuff;
- a camera module; and
- a camera housing positioned in the camera lumen extension and enclosing the camera module, the camera housing comprising:
  - a tubular camera housing part including an inner face and a guide rib extending longitudinally and radially inwardly from the inner face, the inner face defining an inner spacing of the camera housing; and
  - a support structure received in the inner spacing and securing the camera module to the camera housing, the support structure comprising:
    - a proximal end including a tubular end part comprising an outer face adhesively bonded to the inner face of the tubular camera housing part, the tubular end part also comprising ribs extending radially outwardly from the outer face to form a gap for an adhesive and to center the support structure inside the camera tubular housing part;
    - a distal end; and
    - an elongated part connecting the distal end to the proximal end and comprising a longitudinal groove, the guide rib being configured to slide in the longitudinal groove to guide insertion of the support structure into the tubular camera housing part.

20. A medical device including:
- a main tube having an outer wall, a distal end, a first lumen, a second lumen, a second cuff lumen, a flush lumen and a camera lumen, the first lumen having a proximal end and a distal end, the camera lumen having a proximal end and a distal end, the outer wall enclosing the first lumen and the second lumen, and the second cuff lumen, the flush lumen and the camera lumen extending within the outer wall;
- a first inflatable cuff on the main tube;

a tip housing separately manufactured from the main tube, the tip housing comprising:

a proximal end mounted at the distal end of the main tube, a distal end, a tubular housing part including an outer surface extending from the proximal end to the distal end of the tip housing, a first lumen extension including an open end and extending distally from the first lumen, a second lumen extension including an open end and extending distally from the second lumen, a second cuff lumen extension extending distally from the second cuff lumen, a flush lumen extension extending distally from the flush lumen to a flush outlet, the flush lumen extension being formed in a wall of the tubular housing part between the outer surface and a camera lumen surface that circumferentially closed, and the flush outlet comprising a flush opening in the camera lumen surface;

a camera lumen extension extending distally from the camera lumen, the camera lumen extension including a proximal end adjacent the main tube, a distal end having an opening, the camera lumen surface extending from the proximal end to the distal end of the camera lumen, and the flush opening in the camera lumen surface intermediate the proximal end and the distal end of the camera lumen, the flush outlet fluidly coupling the flush lumen extension and the flush opening to discharge a fluid received from the flush lumen through the flush opening into the distal end of the camera lumen extension;

the tubular housing part enclosing the first lumen extension, the second lumen extension, the second cuff lumen extension, and the camera lumen extension;

a second inflatable cuff;

a distal tube mounted onto the distal end of the tip housing and comprising an outer wall enclosing a distal second lumen extension, the distal second lumen extension extending distally from the second lumen extension, the distal tube forming a distal second cuff lumen extension fluidly coupling the second cuff lumen extension and the second inflatable cuff;

a camera module; and a camera housing positioned in the camera lumen extension and enclosing the camera module, the camera housing comprising:

a tubular camera housing part including an inner face, the inner face defining an inner spacing of the camera housing; and a support structure securing the camera module in the camera housing.

* * * * *